United States Patent [19]
Dijkhuizen et al.

[11] Patent Number: 6,004,790
[45] Date of Patent: Dec. 21, 1999

[54] CYCLOMALTODEXTRIN GLUCANOTRANSFERASE VARIANTS

[75] Inventors: Lubbert Dijkhuizen; Bauke W. Dijkstra, both of Groningen, Netherlands; Carsten Andersen; Claus von der Osten, both of Bagsvaerd, Denmark

[73] Assignee: Novo Nordisk A/S, Bagsværd, Denmark

[21] Appl. No.: 08/947,965

[22] Filed: Oct. 9, 1997

Related U.S. Application Data

[63] Continuation of application No. PCT/DK96/00179, Apr. 22, 1996.

[30] Foreign Application Priority Data

Apr. 21, 1995 [DK] Denmark ................................ 0477/95
Oct. 17, 1995 [DK] Denmark ................................ 1173/95
Nov. 16, 1995 [DK] Denmark ................................ 1281/95

[51] Int. Cl.$^6$ .............................. C12N 9/10; C12N 15/00; C07H 21/04
[52] U.S. Cl. ........................ 435/193; 435/320.1; 536/23.2
[58] Field of Search .................................. 435/440, 193, 435/320.1; 536/23.2; 935/22

[56] References Cited

U.S. PATENT DOCUMENTS

| | | | |
|---|---|---|---|
| 5,162,210 | 11/1992 | Sierks et al. ............................. | 435/96 |
| 5,278,059 | 1/1994 | Sugimoto et al. ..................... | 435/193 |
| 5,474,917 | 12/1995 | Schulz et al. ........................... | 435/97 |
| 5,538,882 | 7/1996 | Matsui et al. ......................... | 435/193 |
| 5,635,378 | 6/1997 | Matsui et al. ........................... | 435/97 |

FOREIGN PATENT DOCUMENTS

| | | |
|---|---|---|
| 0 614 971 | 9/1994 | European Pat. Off. . |
| 0 630 967 | 12/1994 | European Pat. Off. . |
| 5-41985 | 2/1993 | Japan . |
| 5-219948 | 8/1993 | Japan . |
| 5-244945 | 9/1993 | Japan . |
| 7-23781 | 1/1995 | Japan . |
| WO 89/03421 | 4/1989 | WIPO . |
| WO 91/14770 | 10/1991 | WIPO . |

OTHER PUBLICATIONS

Rudinger (Jun. 1976) Characteristics of the amino acids as components of a peptide hormone sequence. In: Peptide Hormones. Ed. J. A. Parsons. University Park Press, Baltimore, MD. pp. 1–7.

Ngo et al. (Jan. 1994) Computational complexity, protein structure prediction, and the ILevinthal paradox. In: The Protein Folding Problem and Tertiary Structure Prediction. Eds. Merz et al. Birkhauser et al. Boston, MA. pp. 491–495.

Thornton et al. (Aug. 1995) Protein Engineering: Editorial Overview. Current Opinion in Biotechnology 6(4): 367–369.

Wallace (Apr. 1993) Understanding cytochrome c function: engineering protein structure by semisynthesis. The FASEB Journal 7: 505–515.

Mattsson et al. (Feb. 1995) The role of histidine residues in the catalytic act of cyclomaltodextrin glucanotransferase from Bacillus circulans var. alkalophilus. Biochimica et. Biophysica Acta 1247(1): 97–103.

Kimura et al. (Jun. 1989) Functions of the COOH–terminal region of cyclodextrin glucanotransferase of alkalophilic Bacillus sp. #1011: Relation to catalyzing activity and pH stability. Biochem. Biophys. Res. Commun. 161(3): 1273–1279.

Knegtel et al. (Dec. 1995) Crystallographic studies of the interaction of cyclodextrin glycosyltransferase from Bacillus circulans Strain 251 with natural substrates and products. J. Biol. Chem. 270(49): 29256–29264.

Nakamura et al., Biochemistry, vol. 33, pp.9929–9936 (1994).

Penninga et al., Biochemistry, vol. 34, pp. 3368–3376 (1995).

Fujiwara, et al., Journal of Bacteriology, vol. 174, No. 22, pp. 7478–7481 (Nov. 1992).

B. Strokopytov, Biochemistry, vol. 34 (7), pp. 2234–2240 (Feb. 21, 1995).

Sin et al., Journal of Biotechnology, vol. 32, pp. 283–288 (1994).

Nakamura et al., FEBS Lett, vol. 296 (1), pp. 37–40 (Jan. 13, 1992).

Klein et al., J. Mol. Biol., vol. 217, pp. 737–750 (1991).

Nakamura et al., Biochemistry, vol. 32, pp. 6624–6631 (1993).

*Primary Examiner*—Bradley Sisson
*Assistant Examiner*—Einar Stole
*Attorney, Agent, or Firm*—Steve T. Zelson, Esq.; Elias J. Lambiris, Esq.

[57] ABSTRACT

The present invention relates to variants of cyclomaltodextrin glucanotransferase. More specifically the invention relates to a method of modifying the substrate binding and/or product selectivity of a precursor CGTase enzyme, and CGTase variants derived from a precursor CGTase enzyme by substitution, insertion and/or deletion of one or more amino acid residue(s), which amino acid residue(s) holds a position close to the substrate. Moreover, the invention relates to DNA constructs encoding the CGTase variants, expression vectors, host cells and methods of producing the CGTase variants of the invention.

62 Claims, 10 Drawing Sheets

HOURS OF INCUBATION

% RAW STARCH

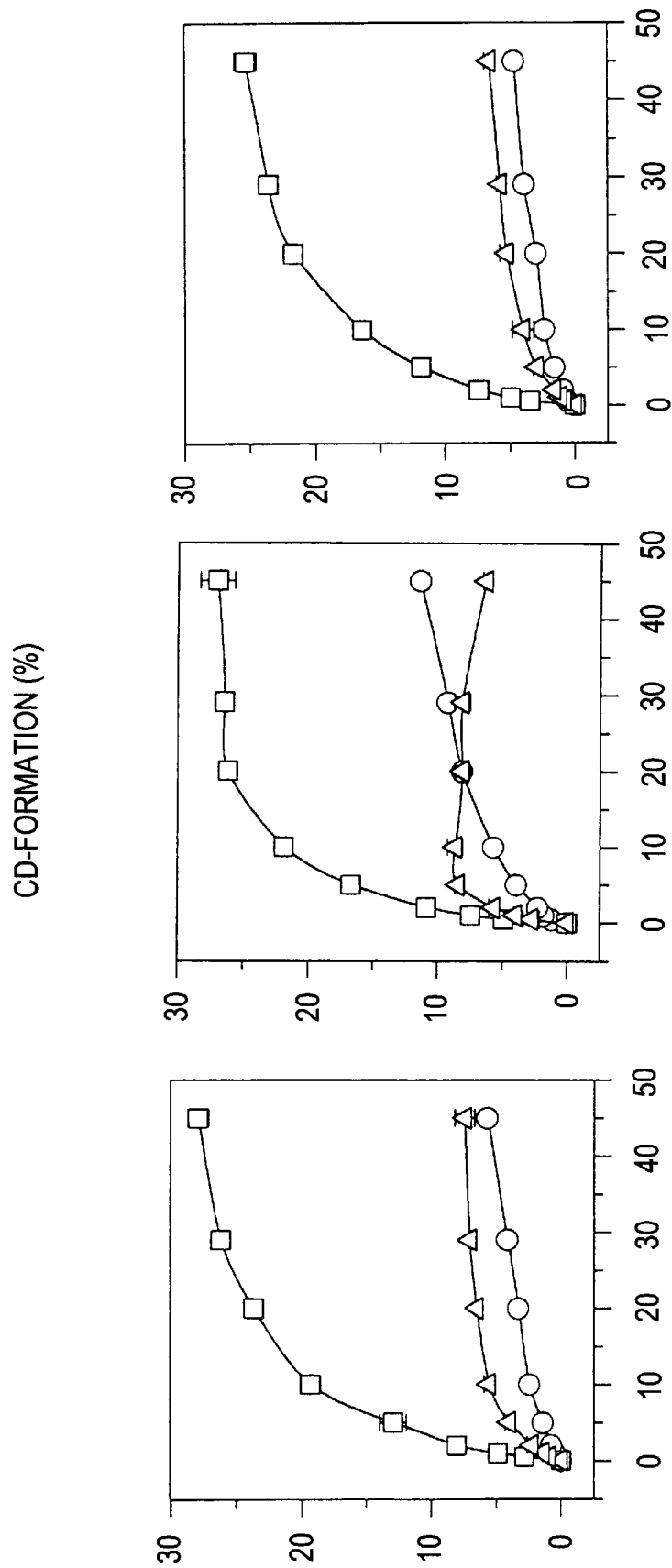

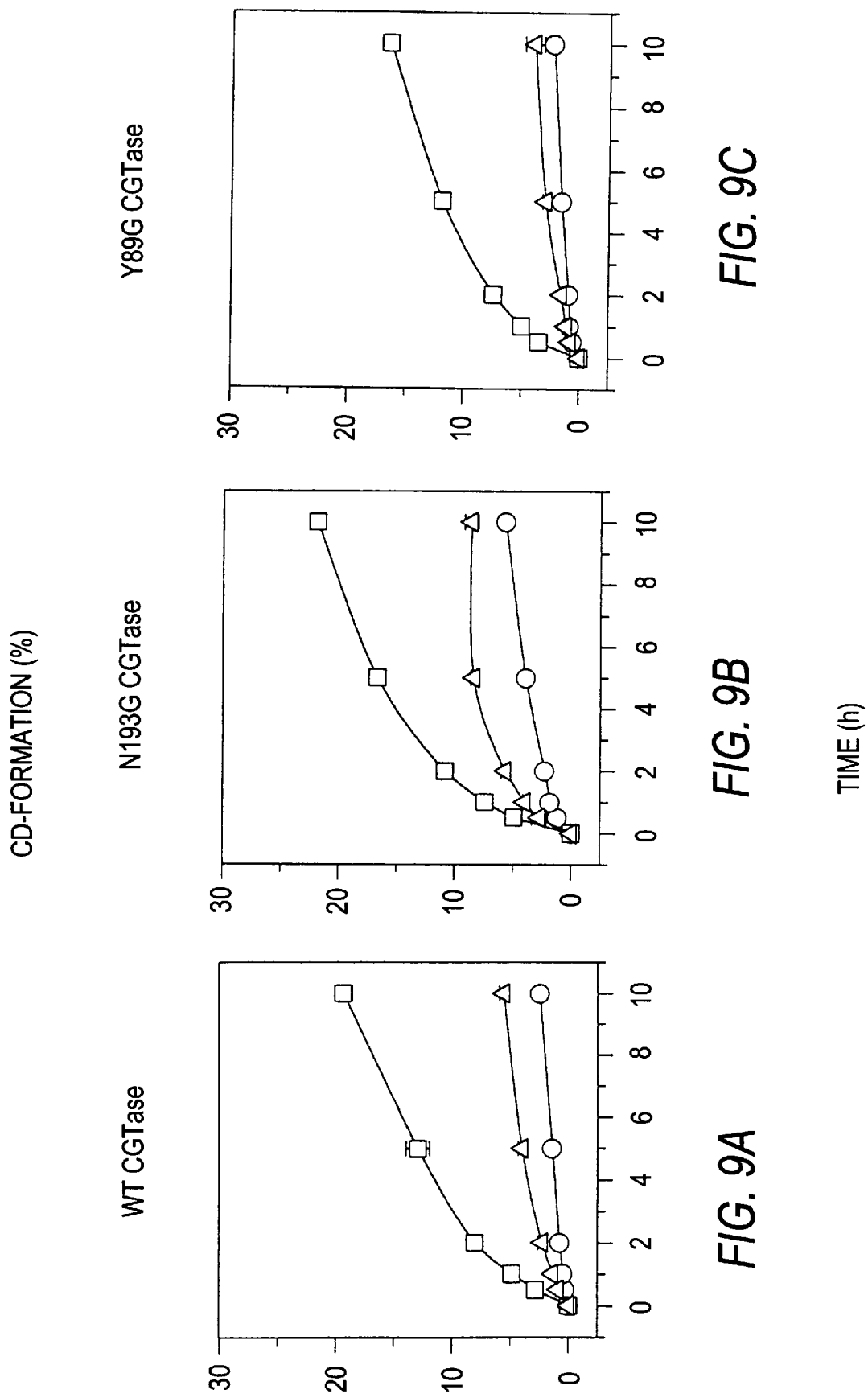

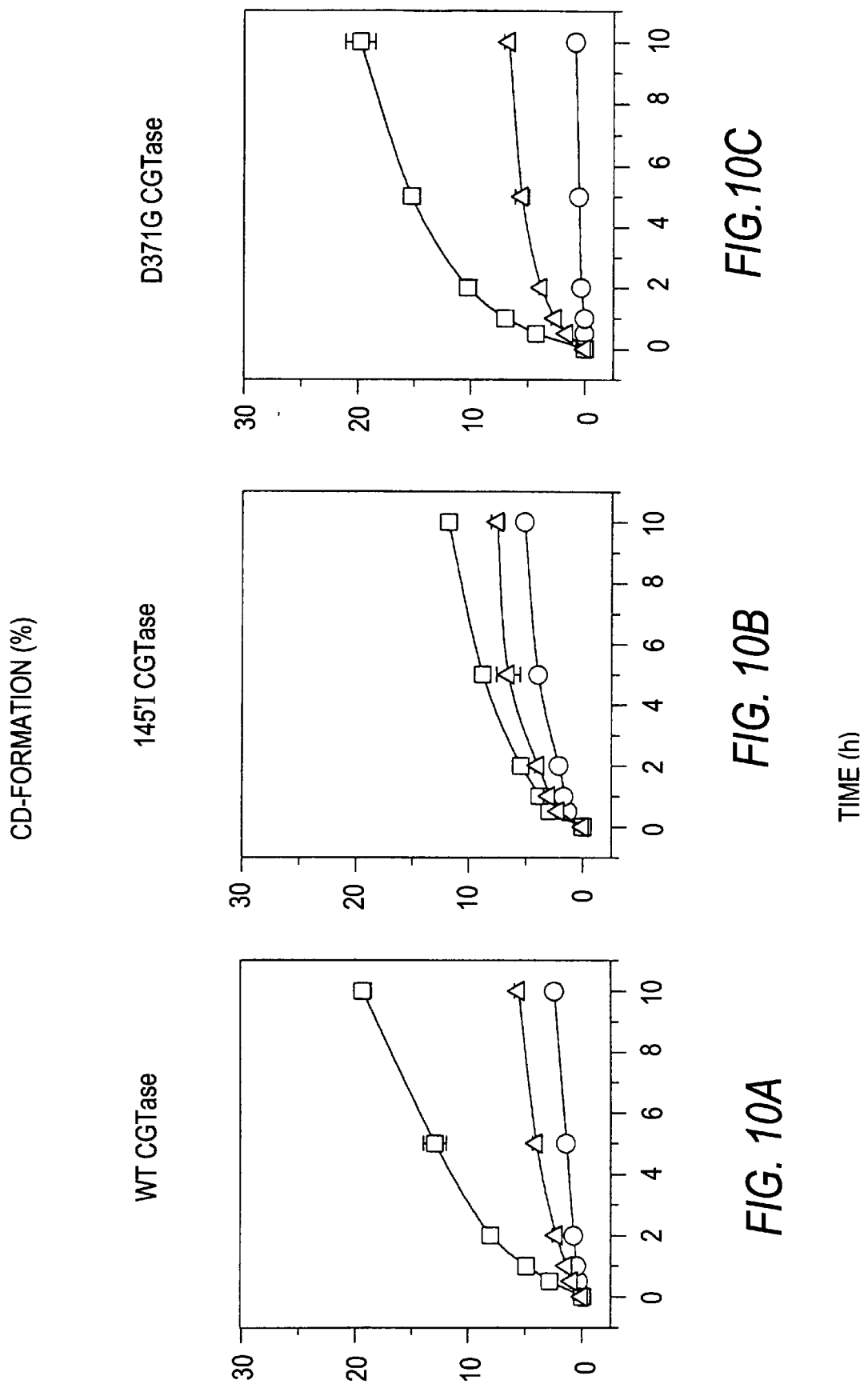

SEQUENCE LISTING

<160> NUMBER OF SEQ ID NOS: 78

<210> SEQ ID NO 1
<211> LENGTH: 2133
<212> TYPE: DNA
<213> ORGANISM: Thermoanaerobacter sp.
<220> FEATURE:
<221> NAME/KEY: CDS
<222> LOCATION: (82)...(2130)

<400> SEQUENCE: 1

```
atgaagaaaa cgcttaaact tctgtcgatt ctgttgataa ccattgctct tcttttcagc        60
tcaattccat ccgtaccggc a gca ccg gat act tca gtt tcc aat gtt gtc       111
               Ala Pro Asp Thr Ser Val Ser Asn Val Val
                 1               5                  10 aat tat tca aca gat gta atc tac cag ata gtc aca gac cgt ttt tta       159
Asn Tyr Ser Thr Asp Val Ile Tyr Gln Ile Val Thr Asp Arg Phe Leu
             15                  20                  25 gat ggg aat ccc agt aat aat cca aca ggc gac tta tat gac cct acc       207
Asp Gly Asn Pro Ser Asn Asn Pro Thr Gly Asp Leu Tyr Asp Pro Thr
         30                  35                  40 cat act agt tta aag aaa tat ttt ggt ggc gat tgg cag ggt att att       255
His Thr Ser Leu Lys Lys Tyr Phe Gly Gly Asp Trp Gln Gly Ile Ile
     45                  50                  55 aac aaa att aat gat ggt tat ctt act ggt atg gga att aca gct ata       303
Asn Lys Ile Asn Asp Gly Tyr Leu Thr Gly Met Gly Ile Thr Ala Ile
 60                  65                  70 tgg att tcg caa cct gta gaa aac att tac gca gtt ttg cca gat tcc       351
Trp Ile Ser Gln Pro Val Glu Asn Ile Tyr Ala Val Leu Pro Asp Ser
 75                  80                  85                  90 act ttt ggc gga agc aca tcc tat cat ggt tac tgg gca cga gac ttc       399
Thr Phe Gly Gly Ser Thr Ser Tyr His Gly Tyr Trp Ala Arg Asp Phe
                 95                 100                 105 aaa aag aca aat ccc ttt ttt gga agc ttt aca gat ttt caa aat ctc       447
Lys Lys Thr Asn Pro Phe Phe Gly Ser Phe Thr Asp Phe Gln Asn Leu
            110                 115                 120
```

-continued

| | |
|---|---|
| ata gca aca gct cat gct cac aat ata aaa gtt ata ata gac ttt gca<br>Ile Ala Thr Ala His Ala His Asn Ile Lys Val Ile Ile Asp Phe Ala<br>              125                      130                      135 | 495 |
| cca aat cat aca tct cct gca tca gag aca gac cct acc tat ggg gaa<br>Pro Asn His Thr Ser Pro Ala Ser Glu Thr Asp Pro Thr Tyr Gly Glu<br>    140                      145                      150 | 543 |
| aat ggt aga tta tat gac aat gga gta tta ctt ggt ggt tat acc aat<br>Asn Gly Arg Leu Tyr Asp Asn Gly Val Leu Leu Gly Gly Tyr Thr Asn<br>155                      160                      165                      170 | 591 |
| gat aca aat gga tat ttc cat cat tat gga gga act aat ttt tca tca<br>Asp Thr Asn Gly Tyr Phe His His Tyr Gly Gly Thr Asn Phe Ser Ser<br>                  175                      180                      185 | 639 |
| tat gaa gat gga att tac cgt aat tta ttt gac tta gca gat tta gat<br>Tyr Glu Asp Gly Ile Tyr Arg Asn Leu Phe Asp Leu Ala Asp Leu Asp<br>              190                      195                      200 | 687 |
| cag cag aat agc act att gat tca tat tta aaa gcg gca att aaa cta<br>Gln Gln Asn Ser Thr Ile Asp Ser Tyr Leu Lys Ala Ala Ile Lys Leu<br>            205                      210                      215 | 735 |
| tgg tta gac atg ggg att gat ggt ata cgc atg gat gca gtc aaa cac<br>Trp Leu Asp Met Gly Ile Asp Gly Ile Arg Met Asp Ala Val Lys His<br>220                      225                      230 | 783 |
| atg gca ttt gga tgg caa aag aac ttt atg gat tct att tta agt tat<br>Met Ala Phe Gly Trp Gln Lys Asn Phe Met Asp Ser Ile Leu Ser Tyr<br>235                      240                      245                      250 | 831 |
| aga cca gtt ttt aca ttt ggc gag tgg tac ctt gga acc aat gaa gta<br>Arg Pro Val Phe Thr Phe Gly Glu Trp Tyr Leu Gly Thr Asn Glu Val<br>                  255                      260                      265 | 879 |
| gat cct aat aat acg tat ttt gca aat gaa agt ggt atg agc ctt ctt<br>Asp Pro Asn Asn Thr Tyr Phe Ala Asn Glu Ser Gly Met Ser Leu Leu<br>              270                      275                      280 | 927 |
| gat ttt aga ttt gct caa aaa gtt cgt caa gta ttc aga gac aat aca<br>Asp Phe Arg Phe Ala Gln Lys Val Arg Gln Val Phe Arg Asp Asn Thr<br>            285                      290                      295 | 975 |
| gac act atg tat gga ctt gat tcg atg att cag tct act gca gca gat<br>Asp Thr Met Tyr Gly Leu Asp Ser Met Ile Gln Ser Thr Ala Ala Asp<br>300                      305                      310 | 1023 |
| tat aat ttc ata aat gat atg gtt aca ttt ata gat aat cat gac atg<br>Tyr Asn Phe Ile Asn Asp Met Val Thr Phe Ile Asp Asn His Asp Met<br>315                      320                      325                      330 | 1071 |
| gac aga ttt tat aca gga ggc agt aca cgg cct gtt gag caa gcg tta<br>Asp Arg Phe Tyr Thr Gly Gly Ser Thr Arg Pro Val Glu Gln Ala Leu<br>                  335                      340                      345 | 1119 |
| gca ttt act tta act tct cgc ggt gta cct gct ata tat tac ggt aca<br>Ala Phe Thr Leu Thr Ser Arg Gly Val Pro Ala Ile Tyr Tyr Gly Thr<br>            350                      355                      360 | 1167 |
| gag caa tat atg aca ggt aat gga gac cct tat aat aga gct atg atg<br>Glu Gln Tyr Met Thr Gly Asn Gly Asp Pro Tyr Asn Arg Ala Met Met<br>            365                      370                      375 | 1215 |
| acg tca ttt gac acc aca acg gca tat aat gtg ata aaa aag ctt<br>Thr Ser Phe Asp Thr Thr Thr Ala Tyr Asn Val Ile Lys Lys Leu<br>380                      385                      390 | 1263 |
| gct cca ctg cgt aaa tct aac cct gca att gct tac ggt aca caa aaa<br>Ala Pro Leu Arg Lys Ser Asn Pro Ala Ile Ala Tyr Gly Thr Gln Lys<br>395                      400                      405                      410 | 1311 |
| cag cga tgg ata aat aat gat gtt tac att tat gaa aga caa ttt ggt<br>Gln Arg Trp Ile Asn Asn Asp Val Tyr Ile Tyr Glu Arg Gln Phe Gly<br>                  415                      420                      425 | 1359 |
| aat aac gtt gct ctt gtt gct att aat cgt aat ctt tca acg agc tat<br>Asn Asn Val Ala Leu Val Ala Ile Asn Arg Asn Leu Ser Thr Ser Tyr<br>              430                      435                      440 | 1407 |

| | | | | | | | | | | | | | | | | |
|---|---|---|---|---|---|---|---|---|---|---|---|---|---|---|---|---|
| tac | att | acc | ggc | ttg | tac | acc | gca | ttg | cct | gcg | gga | aca | tat | tct | gac | 1455 |
| Tyr | Ile | Thr | Gly | Leu | Tyr | Thr | Ala | Leu | Pro | Ala | Gly | Thr | Tyr | Ser | Asp | |
| | | 445 | | | | | 450 | | | | | 455 | | | | |
| atg | ctt | ggc | gga | tta | tta | aat | ggc | agt | agt | att | aca | gta | tct | agt | aat | 1503 |
| Met | Leu | Gly | Gly | Leu | Leu | Asn | Gly | Ser | Ser | Ile | Thr | Val | Ser | Ser | Asn | |
| 460 | | | | | 465 | | | | | 470 | | | | | | |
| ggt | tct | gta | aca | ccg | ttt | acc | ctt | gcg | cct | ggt | gaa | gtt | gca | gta | tgg | 1551 |
| Gly | Ser | Val | Thr | Pro | Phe | Thr | Leu | Ala | Pro | Gly | Glu | Val | Ala | Val | Trp | |
| 475 | | | | 480 | | | | | 485 | | | | | 490 | | |
| cag | tat | gtc | agt | aca | act | aat | cct | cca | ttg | ata | gga | cat | gta | gga | ccg | 1599 |
| Gln | Tyr | Val | Ser | Thr | Thr | Asn | Pro | Pro | Leu | Ile | Gly | His | Val | Gly | Pro | |
| | | | 495 | | | | | 500 | | | | | 505 | | | |
| aca | atg | aca | aag | gca | ggg | cag | act | ata | acc | ata | gat | gga | agg | gga | ttt | 1647 |
| Thr | Met | Thr | Lys | Ala | Gly | Gln | Thr | Ile | Thr | Ile | Asp | Gly | Arg | Gly | Phe | |
| | | | 510 | | | | | 515 | | | | | 520 | | | |
| ggc | aca | aca | gca | ggt | caa | gta | tta | ttt | ggg | aca | act | cct | gca | act | att | 1695 |
| Gly | Thr | Thr | Ala | Gly | Gln | Val | Leu | Phe | Gly | Thr | Thr | Pro | Ala | Thr | Ile | |
| | | 525 | | | | | 530 | | | | | 535 | | | | |
| gtg | tca | tgg | gaa | gat | act | gaa | gta | aaa | gta | aaa | gtt | cct | gct | tta | act | 1743 |
| Val | Ser | Trp | Glu | Asp | Thr | Glu | Val | Lys | Val | Lys | Val | Pro | Ala | Leu | Thr | |
| 540 | | | | | 545 | | | | | 550 | | | | | | |
| cct | gga | aaa | tat | aac | att | aca | tta | aaa | aca | gca | tca | gga | gtt | aca | agc | 1791 |
| Pro | Gly | Lys | Tyr | Asn | Ile | Thr | Leu | Lys | Thr | Ala | Ser | Gly | Val | Thr | Ser | |
| 555 | | | | 560 | | | | | 565 | | | | | 570 | | |
| aat | agc | tat | aac | aat | atc | aat | gtt | tta | acg | gga | aat | cag | gta | tgt | gtt | 1839 |
| Asn | Ser | Tyr | Asn | Asn | Ile | Asn | Val | Leu | Thr | Gly | Asn | Gln | Val | Cys | Val | |
| | | | 575 | | | | | 580 | | | | | 585 | | | |
| aga | ttt | gta | gta | aat | aat | gct | aca | acc | gtg | tgg | gga | gaa | aat | gta | tat | 1887 |
| Arg | Phe | Val | Val | Asn | Asn | Ala | Thr | Thr | Val | Trp | Gly | Glu | Asn | Val | Tyr | |
| | | | 590 | | | | | 595 | | | | | 600 | | | |
| ctt | acg | ggc | aat | gta | gct | gaa | ctt | ggc | aac | tgg | gat | aca | tcg | aag | gca | 1935 |
| Leu | Thr | Gly | Asn | Val | Ala | Glu | Leu | Gly | Asn | Trp | Asp | Thr | Ser | Lys | Ala | |
| | | 605 | | | | | 610 | | | | | 615 | | | | |
| ata | gga | cca | atg | ttt | aac | cag | gtt | gtg | tat | caa | tat | cct | acg | tgg | tat | 1983 |
| Ile | Gly | Pro | Met | Phe | Asn | Gln | Val | Val | Tyr | Gln | Tyr | Pro | Thr | Trp | Tyr | |
| | | 620 | | | | | 625 | | | | | 630 | | | | |
| tac | gat | gta | agt | gtg | cct | gct | ggt | act | act | ata | gag | ttt | aag | ttt | ata | 2031 |
| Tyr | Asp | Val | Ser | Val | Pro | Ala | Gly | Thr | Thr | Ile | Glu | Phe | Lys | Phe | Ile | |
| 635 | | | | | 640 | | | | | 645 | | | | | 650 | |
| aag | aaa | aat | ggt | agt | act | gta | acc | tgg | gaa | ggt | gga | tac | aac | cac | gta | 2079 |
| Lys | Lys | Asn | Gly | Ser | Thr | Val | Thr | Trp | Glu | Gly | Gly | Tyr | Asn | His | Val | |
| | | | 655 | | | | | 660 | | | | | 665 | | | |
| tat | act | aca | ccc | act | tct | ggt | aca | gct | act | gta | att | gta | gac | tgg | caa | 2127 |
| Tyr | Thr | Thr | Pro | Thr | Ser | Gly | Thr | Ala | Thr | Val | Ile | Val | Asp | Trp | Gln | |
| | | 670 | | | | | 675 | | | | | 680 | | | | |
| ccg | tga | | | | | | | | | | | | | | | 2133 |
| Pro | | | | | | | | | | | | | | | | |

<210> SEQ ID NO 2
<211> LENGTH: 683
<212> TYPE: PRT
<213> ORGANISM: Thermoanaerobacter sp.

<400> SEQUENCE: 2

| | | | | | | | | | | | | | | | |
|---|---|---|---|---|---|---|---|---|---|---|---|---|---|---|---|
| Ala | Pro | Asp | Thr | Ser | Val | Ser | Asn | Val | Val | Asn | Tyr | Ser | Thr | Asp | Val |
| 1 | | | | 5 | | | | | 10 | | | | | 15 | |
| Ile | Tyr | Gln | Ile | Val | Thr | Asp | Arg | Phe | Leu | Asp | Gly | Asn | Pro | Ser | Asn |
| | | | 20 | | | | | 25 | | | | | 30 | | |
| Asn | Pro | Thr | Gly | Asp | Leu | Tyr | Asp | Pro | Thr | His | Thr | Ser | Leu | Lys | Lys |
| | | 35 | | | | | 40 | | | | | 45 | | | |

-continued

```
Tyr Phe Gly Gly Asp Trp Gln Gly Ile Ile Asn Lys Ile Asn Asp Gly
     50                  55                  60

Tyr Leu Thr Gly Met Gly Ile Thr Ala Ile Trp Ile Ser Gln Pro Val
 65                  70                  75                  80

Glu Asn Ile Tyr Ala Val Leu Pro Asp Ser Thr Phe Gly Gly Ser Thr
                 85                  90                  95

Ser Tyr His Gly Tyr Trp Ala Arg Asp Phe Lys Lys Thr Asn Pro Phe
            100                 105                 110

Phe Gly Ser Phe Thr Asp Phe Gln Asn Leu Ile Ala Thr Ala His Ala
        115                 120                 125

His Asn Ile Lys Val Ile Ile Asp Phe Ala Pro Asn His Thr Ser Pro
130                 135                 140

Ala Ser Glu Thr Asp Pro Thr Tyr Gly Glu Asn Gly Arg Leu Tyr Asp
145                 150                 155                 160

Asn Gly Val Leu Leu Gly Gly Tyr Thr Asn Asp Thr Asn Gly Tyr Phe
                165                 170                 175

His His Tyr Gly Gly Thr Asn Phe Ser Ser Tyr Glu Asp Gly Ile Tyr
            180                 185                 190

Arg Asn Leu Phe Asp Leu Ala Asp Leu Asp Gln Gln Asn Ser Thr Ile
        195                 200                 205

Asp Ser Tyr Leu Lys Ala Ala Ile Lys Leu Trp Leu Asp Met Gly Ile
210                 215                 220

Asp Gly Ile Arg Met Asp Ala Val Lys His Met Ala Phe Gly Trp Gln
225                 230                 235                 240

Lys Asn Phe Met Asp Ser Ile Leu Ser Tyr Arg Pro Val Phe Thr Phe
                245                 250                 255

Gly Glu Trp Tyr Leu Gly Thr Asn Glu Val Asp Pro Asn Asn Thr Tyr
            260                 265                 270

Phe Ala Asn Glu Ser Gly Met Ser Leu Leu Asp Phe Arg Phe Ala Gln
        275                 280                 285

Lys Val Arg Gln Val Phe Arg Asp Asn Thr Asp Thr Met Tyr Gly Leu
290                 295                 300

Asp Ser Met Ile Gln Ser Thr Ala Ala Asp Tyr Asn Phe Ile Asn Asp
305                 310                 315                 320

Met Val Thr Phe Ile Asp Asn His Asp Met Asp Arg Phe Tyr Thr Gly
                325                 330                 335

Gly Ser Thr Arg Pro Val Glu Gln Ala Leu Ala Phe Thr Leu Thr Ser
            340                 345                 350

Arg Gly Val Pro Ala Ile Tyr Tyr Gly Thr Glu Gln Tyr Met Thr Gly
        355                 360                 365

Asn Gly Asp Pro Tyr Asn Arg Ala Met Met Thr Ser Phe Asp Thr Thr
370                 375                 380

Thr Thr Ala Tyr Asn Val Ile Lys Lys Leu Ala Pro Leu Arg Lys Ser
385                 390                 395                 400

Asn Pro Ala Ile Ala Tyr Gly Thr Gln Lys Gln Arg Trp Ile Asn Asn
                405                 410                 415

Asp Val Tyr Ile Tyr Glu Arg Gln Phe Gly Asn Asn Val Ala Leu Val
            420                 425                 430

Ala Ile Asn Arg Asn Leu Ser Thr Ser Tyr Tyr Ile Thr Gly Leu Tyr
        435                 440                 445

Thr Ala Leu Pro Ala Gly Thr Tyr Ser Asp Met Leu Gly Gly Leu Leu
450                 455                 460

Asn Gly Ser Ser Ile Thr Val Ser Ser Asn Gly Ser Val Thr Pro Phe
465                 470                 475                 480
```

-continued

```
Thr Leu Ala Pro Gly Glu Val Ala Val Trp Gln Tyr Val Ser Thr Thr
                485                 490                 495

Asn Pro Pro Leu Ile Gly His Val Gly Pro Thr Met Thr Lys Ala Gly
            500                 505                 510

Gln Thr Ile Thr Ile Asp Gly Arg Gly Phe Gly Thr Thr Ala Gly Gln
        515                 520                 525

Val Leu Phe Gly Thr Thr Pro Ala Thr Ile Val Ser Trp Glu Asp Thr
    530                 535                 540

Glu Val Lys Val Lys Val Pro Ala Leu Thr Pro Gly Lys Tyr Asn Ile
545                 550                 555                 560

Thr Leu Lys Thr Ala Ser Gly Val Thr Ser Asn Ser Tyr Asn Asn Ile
                565                 570                 575

Asn Val Leu Thr Gly Asn Gln Val Cys Val Arg Phe Val Val Asn Asn
            580                 585                 590

Ala Thr Thr Val Trp Gly Glu Asn Val Tyr Leu Thr Gly Asn Val Ala
        595                 600                 605

Glu Leu Gly Asn Trp Asp Thr Ser Lys Ala Ile Gly Pro Met Phe Asn
    610                 615                 620

Gln Val Val Tyr Gln Tyr Pro Thr Trp Tyr Tyr Asp Val Ser Val Pro
625                 630                 635                 640

Ala Gly Thr Thr Ile Glu Phe Lys Phe Ile Lys Lys Asn Gly Ser Thr
                645                 650                 655

Val Thr Trp Glu Gly Gly Tyr Asn His Val Tyr Thr Thr Pro Thr Ser
            660                 665                 670

Gly Thr Ala Thr Val Ile Val Asp Trp Gln Pro
        675                 680

<210> SEQ ID NO 3
<211> LENGTH: 5
<212> TYPE: PRT
<213> ORGANISM: Unknown
<220> FEATURE:
<221> NAME/KEY: VARIANT
<222> LOCATION: (87)...(94)

<400> SEQUENCE: 3

His Pro Ser Gly Tyr
1               5

<210> SEQ ID NO 4
<211> LENGTH: 9
<212> TYPE: PRT
<213> ORGANISM: Unknown
<220> FEATURE:
<221> NAME/KEY: VARIANT
<222> LOCATION: (143)...(151)

<400> SEQUENCE: 4

Pro Ala Leu Glu Thr Asn Pro Asn Phe
1               5

<210> SEQ ID NO 5
<211> LENGTH: 9
<212> TYPE: PRT
<213> ORGANISM: Unknown
<220> FEATURE:
<221> NAME/KEY: VARIANT
<222> LOCATION: (143)...(151)

<400> SEQUENCE: 5

Pro Ala Ala Glu Thr Trp Pro Ala Phe
```

```
             1               5

<210> SEQ ID NO 6
<211> LENGTH: 9
<212> TYPE: PRT
<213> ORGANISM: Unknown
<220> FEATURE:
<221> NAME/KEY: VARIANT
<222> LOCATION: (143)...(151)

<400> SEQUENCE: 6

Pro Ala Ala Glu Ala Asp Pro Asn Phe
 1               5

<210> SEQ ID NO 7
<211> LENGTH: 4
<212> TYPE: PRT
<213> ORGANISM: Unknown
<220> FEATURE:
<221> NAME/KEY: VARIANT
<222> LOCATION: (143)...(148)

<400> SEQUENCE: 7

Gly Arg Ala Ala
 1

<210> SEQ ID NO 8
<211> LENGTH: 6
<212> TYPE: PRT
<213> ORGANISM: Unknown
<220> FEATURE:
<221> NAME/KEY: VARIANT
<222> LOCATION: (143)...(148)

<400> SEQUENCE: 8

Gly Arg Ala Ala Ala Ala
 1               5

<210> SEQ ID NO 9
<211> LENGTH: 6
<212> TYPE: PRT
<213> ORGANISM: Unknown
<220> FEATURE:
<221> NAME/KEY: VARIANT
<222> LOCATION: (143)...(148)

<400> SEQUENCE: 9

Gly Arg Ala Pro Ala Ala
 1               5

<210> SEQ ID NO 10
<211> LENGTH: 6
<212> TYPE: PRT
<213> ORGANISM: Unknown
<220> FEATURE:
<221> NAME/KEY: VARIANT
<222> LOCATION: (143)...(148)
```

```
<400> SEQUENCE: 10

Gly Arg Gly Pro Ala Ala
 1               5

<210> SEQ ID NO 11
<211> LENGTH: 8
<212> TYPE: PRT
<213> ORGANISM: Unknown
<220> FEATURE:
<221> NAME/KEY: VARIANT
<222> LOCATION: (87)...(94)

<400> SEQUENCE: 11

Ile Lys Tyr Ser Gly Val Asn Asn
 1               5

<210> SEQ ID NO 12
<211> LENGTH: 9
<212> TYPE: PRT
<213> ORGANISM: Unknown
<220> FEATURE:
<221> NAME/KEY: VARIANT
<222> LOCATION: (143)...(151)

<400> SEQUENCE: 12

Gly Arg Ala Gly Thr Asn Pro Gly Phe
 1               5

<210> SEQ ID NO 13
<211> LENGTH: 25
<212> TYPE: DNA
<213> ORGANISM: Artificial Sequence
<220> FEATURE:
<223> OTHER INFORMATION: nucleotide

<400> SEQUENCE: 13
ggtcgtttac caggcgccga actgg                                           25

<210> SEQ ID NO 14
<211> LENGTH: 23
<212> TYPE: DNA
<213> ORGANISM: Artificial Sequence
<220> FEATURE:
<223> OTHER INFORMATION: nucleotide

<400> SEQUENCE: 14
gcgagctcgg gaacgcggac ccg                                             23

<210> SEQ ID NO 15
<211> LENGTH: 20
<212> TYPE: DNA
<213> ORGANISM: Artificial Sequence
<220> FEATURE:
<223> OTHER INFORMATION: Nucleotide

<400> SEQUENCE: 15
ccgtcaccgc ggaaggcggc                                                 20

<210> SEQ ID NO 16
<211> LENGTH: 27
<212> TYPE: DNA
<213> ORGANISM: Artificial Sequence
<220> FEATURE:
<223> OTHER INFORMATION: nucleotide

<400> SEQUENCE: 16
gcatctacaa gggcctgtac gatctcg                                         27
```

<210> SEQ ID NO 17
<211> LENGTH: 26
<212> TYPE: DNA
<213> ORGANISM: Artificial Sequence
<220> FEATURE:
<223> OTHER INFORMATION: nucleotide

<400> SEQUENCE: 17
gcatcatcaa tggatccggc gtaaac                                        26

<210> SEQ ID NO 18
<211> LENGTH: 36
<212> TYPE: DNA
<213> ORGANISM: Artificial Sequence
<220> FEATURE:
<223> OTHER INFORMATION: nucleotide

<400> SEQUENCE: 18
catacgtcgc ccgctagcat ttccgaccag ccttcc                             36

<210> SEQ ID NO 19
<211> LENGTH: 25
<212> TYPE: DNA
<213> ORGANISM: Artificial Sequence
<220> FEATURE:
<223> OTHER INFORMATION: nucleotide

<400> SEQUENCE: 19
cgggcgggac cggtccggac aaccg                                         25

<210> SEQ ID NO 20
<211> LENGTH: 26
<212> TYPE: DNA
<213> ORGANISM: Artificial Sequence
<220> FEATURE:
<223> OTHER INFORMATION: nucleotide

<400> SEQUENCE: 20
gtcgggcggt accaatccgg acaacc                                        26

<210> SEQ ID NO 21
<211> LENGTH: 24
<212> TYPE: DNA
<213> ORGANISM: Artificial Sequence
<220> FEATURE:
<223> OTHER INFORMATION: nucleotide

<400> SEQUENCE: 21
cgttcatcga tcagcatgac atgg                                          24

<210> SEQ ID NO 22
<211> LENGTH: 24
<212> TYPE: DNA
<213> ORGANISM: Artificial Sequence
<220> FEATURE:
<223> OTHER INFORMATION: nucleotide

<400> SEQUENCE: 22
gcccgcctct ccggaccagc cttc                                          24

<210> SEQ ID NO 23
<211> LENGTH: 52
<212> TYPE: DNA
<213> ORGANISM: Artificial Sequence
<220> FEATURE:
<223> OTHER INFORMATION: nucleotide

<400> SEQUENCE: 23
aatcatacat ctggacgagc aggtaccaac ccgactttgg ggaaaatggt ac          52

<210> SEQ ID NO 24
<211> LENGTH: 35
<212> TYPE: DNA
<213> ORGANISM: Artificial Sequence
<220> FEATURE:
<223> OTHER INFORMATION: nucleotide

<400> SEQUENCE: 24
atcatacatc cggacgatgg gagacagacc ctacc                             35

<210> SEQ ID NO 25
<211> LENGTH: 51
<212> TYPE: DNA
<213> ORGANISM: Artificial Sequence
<220> FEATURE:
<223> OTHER INFORMATION: nucleotide

<400> SEQUENCE: 25
catttacgca gttatcaatg attccggagt taacaataca tcctatcatg g           51

<210> SEQ ID NO 26
<211> LENGTH: 45
<212> TYPE: DNA
<213> ORGANISM: Artificial sequence
<220> FEATURE:
<223> OTHER INFORMATION: nucleotide

<400> SEQUENCE: 26
caaatcatac atctggacga ggaccggccg cacctaccta tgggg                  45

<210> SEQ ID NO 27
<211> LENGTH: 45
<212> TYPE: DNA
<213> ORGANISM: Artificial sequence
<220> FEATURE:
<223> OTHER INFORMATION: nucleotide

<400> SEQUENCE: 27
caaatcatac atctggacga gcaccggccg cacctaccta tgggg                  45

<210> SEQ ID NO 28
<211> LENGTH: 39
<212> TYPE: DNA
<213> ORGANISM: Artificial sequence
<220> FEATURE:
<223> OTHER INFORMATION: nucleotide

<400> SEQUENCE: 28
caaatcatac atctggacga gcagcaccta cctatgggg                         39

<210> SEQ ID NO 29
<211> LENGTH: 45
<212> TYPE: DNA
<213> ORGANISM: Artificial sequence
<220> FEATURE:
<223> OTHER INFORMATION: nucleotide

<400> SEQUENCE: 29
caaatcatac atctggacga cctgcagcag ctcctaccta tgggg                  45

<210> SEQ ID NO 30
<211> LENGTH: 30

```
<212> TYPE: DNA
<213> ORGANISM: Artificial sequence
<220> FEATURE:
<223> OTHER INFORMATION: nucleotide

<400> SEQUENCE: 30
ccatcattac ggatccacta atttttcatc                                            30

<210> SEQ ID NO 31
<211> LENGTH: 29
<212> TYPE: DNA
<213> ORGANISM: Artificial sequence
<220> FEATURE:
<223> OTHER INFORMATION: nucleotide

<400> SEQUENCE: 31
catacatctc ctcgatcgga gacagaccc                                             29

<210> SEQ ID NO 32
<211> LENGTH: 29
<212> TYPE: DNA
<213> ORGANISM: Artificial sequence
<220> FEATURE:
<223> OTHER INFORMATION: nucleotide

<400> SEQUENCE: 32
catacatctg ctcgatcgga gacagaccc                                             29

<210> SEQ ID NO 33
<211> LENGTH: 30
<212> TYPE: DNA
<213> ORGANISM: Artificial sequence
<220> FEATURE:
<223> OTHER INFORMATION: nucleotide

<400> SEQUENCE: 33
ccatcattac ggaaacacta atttttcatc                                            30

<210> SEQ ID NO 34
<211> LENGTH: 30
<212> TYPE: DNA
<213> ORGANISM: Artificial sequence
<220> FEATURE:
<223> OTHER INFORMATION: nucleotide

<400> SEQUENCE: 34
ccatcattac ggagacacta atttttcatc                                            30

<210> SEQ ID NO 35
<211> LENGTH: 30
<212> TYPE: DNA
<213> ORGANISM: Artificial sequence
<220> FEATURE:
<223> OTHER INFORMATION: nucleotide

<400> SEQUENCE: 35
ccatcattat aatggaacta atttttcatc                                            30

<210> SEQ ID NO 36
<211> LENGTH: 30
<212> TYPE: DNA
<213> ORGANISM: Artificial sequence
<220> FEATURE:
<223> OTHER INFORMATION: nucleotide

<400> SEQUENCE: 36
ccatcattat agtggaacta atttttcatc                                            30
```

```
<210> SEQ ID NO 37
<211> LENGTH: 30
<212> TYPE: DNA
<213> ORGANISM: Artificial sequence
<220> FEATURE:
<223> OTHER INFORMATION: nucleotide

<400> SEQUENCE: 37
ccatcattat gatggaacta atttttcatc                                         30

<210> SEQ ID NO 38
<211> LENGTH: 22
<212> TYPE: DNA
<213> ORGANISM: Artificial sequence
<220> FEATURE:
<223> OTHER INFORMATION: nucleotide

<400> SEQUENCE: 38
ctcctgcagc tgagacagac cc                                                 22

<210> SEQ ID NO 39
<211> LENGTH: 22
<212> TYPE: DNA
<213> ORGANISM: Artificial sequence
<220> FEATURE:
<223> OTHER INFORMATION: nucleotide

<400> SEQUENCE: 39
ctcctgcatc gtcgacagac cc                                                 22

<210> SEQ ID NO 40
<211> LENGTH: 23
<212> TYPE: DNA
<213> ORGANISM: Artificial sequence
<220> FEATURE:
<223> OTHER INFORMATION: nucleotide

<400> SEQUENCE: 40
tcagaggcgg atcctaccta tgg                                                23

<210> SEQ ID NO 41
<211> LENGTH: 23
<212> TYPE: DNA
<213> ORGANISM: Artificial sequence
<220> FEATURE:
<223> OTHER INFORMATION: nucleotide

<400> SEQUENCE: 41
tcagagctcg accctaccta tgg                                                23

<210> SEQ ID NO 42
<211> LENGTH: 24
<212> TYPE: DNA
<213> ORGANISM: Artificial sequence
<220> FEATURE:
<223> OTHER INFORMATION: nucleotide

<400> SEQUENCE: 42
cagagacggc gcctacctat gggg                                               24

<210> SEQ ID NO 43
<211> LENGTH: 21
<212> TYPE: DNA
<213> ORGANISM: Artificial sequence
<220> FEATURE:
<223> OTHER INFORMATION: nucleotide
```

<400> SEQUENCE: 43
cgcagttttg ccggcttcca c                                          21

<210> SEQ ID NO 44
<211> LENGTH: 20
<212> TYPE: DNA
<213> ORGANISM: Artificial sequence
<220> FEATURE:
<223> OTHER INFORMATION: nucleotide

<400> SEQUENCE: 44
tccactgccg gcggaagcac                                            20

<210> SEQ ID NO 45
<211> LENGTH: 21
<212> TYPE: DNA
<213> ORGANISM: Artificial sequence
<220> FEATURE:
<223> OTHER INFORMATION: nucleotide

<400> SEQUENCE: 45
agattctacc ggtggaagca c                                          21

<210> SEQ ID NO 46
<211> LENGTH: 49
<212> TYPE: DNA
<213> ORGANISM: Artificial sequence
<220> FEATURE:
<223> OTHER INFORMATION: nucleotide

<400> SEQUENCE: 46
tttacgcagt tattaaatat tccggcgtta acaacacatc ctatcatgg            49

<210> SEQ ID NO 47
<211> LENGTH: 28
<212> TYPE: DNA
<213> ORGANISM: Artificial sequence
<220> FEATURE:
<223> OTHER INFORMATION: nucleotide

<400> SEQUENCE: 47
cgtaatttat tcgcgctagc agatttag                                   28

<210> SEQ ID NO 48
<211> LENGTH: 28
<212> TYPE: DNA
<213> ORGANISM: Artificial sequence
<220> FEATURE:
<223> OTHER INFORMATION: nucleotide

<400> SEQUENCE: 48
caggtaatgg taacccttat aatagagc                                   28

<210> SEQ ID NO 49
<211> LENGTH: 28
<212> TYPE: DNA
<213> ORGANISM: Artificial sequence
<220> FEATURE:
<223> OTHER INFORMATION: nucleotide

<400> SEQUENCE: 49
caggtaatgg agggccttat aatagagc                                   28

<210> SEQ ID NO 50
<211> LENGTH: 28

<212> TYPE: DNA
<213> ORGANISM: Artificial sequence
<220> FEATURE:
<223> OTHER INFORMATION: nucleotide

<400> SEQUENCE: 50
caggtaatgg agcgccttat aatagagc                                          28

<210> SEQ ID NO 51
<211> LENGTH: 24
<212> TYPE: DNA
<213> ORGANISM: Artificial sequence
<220> FEATURE:
<223> OTHER INFORMATION: nucleotide

<400> SEQUENCE: 51
ttaccgtgca ctatttgact tagc                                              24

<210> SEQ ID NO 52
<211> LENGTH: 40
<212> TYPE: DNA
<213> ORGANISM: Artificial sequence
<220> FEATURE:
<223> OTHER INFORMATION: nucleotide

<400> SEQUENCE: 52
ctcctgcatc atctgatcaa ccgtcctttg gggaaaatgg                              40

<210> SEQ ID NO 53
<211> LENGTH: 35
<212> TYPE: DNA
<213> ORGANISM: Artificial sequence
<220> FEATURE:
<223> OTHER INFORMATION: nucleotide

<400> SEQUENCE: 53
catctcctgc agcagagctc gcacctacct atggg                                  35

<210> SEQ ID NO 54
<211> LENGTH: 35
<212> TYPE: DNA
<213> ORGANISM: Artificial sequence
<220> FEATURE:
<223> OTHER INFORMATION: nucleotide

<400> SEQUENCE: 54
catctcctgc agcagagtgg gcacctacct atggg                                  35

<210> SEQ ID NO 55
<211> LENGTH: 51
<212> TYPE: DNA
<213> ORGANISM: Artificial sequence
<220> FEATURE:
<223> OTHER INFORMATION: nucleotide

<400> SEQUENCE: 55
catttacgca gttatcaatt attccggagt taacaataca tcctatcatg g                51

<210> SEQ ID NO 56
<211> LENGTH: 42
<212> TYPE: DNA
<213> ORGANISM: Artificial sequence
<220> FEATURE:
<223> OTHER INFORMATION: nucleotide

<400> SEQUENCE: 56
catttacgca gttcatcctt ccgggtatac atcctatcat gg                          42

-continued

```
<210> SEQ ID NO 57
<211> LENGTH: 36
<212> TYPE: DNA
<213> ORGANISM: Artificial sequence
<220> FEATURE:
<223> OTHER INFORMATION: nucleotide

<400> SEQUENCE: 57
tacatctcct gcactcgaga caaatcctac ctatgg                              36

<210> SEQ ID NO 58
<211> LENGTH: 8
<212> TYPE: PRT
<213> ORGANISM: Unknown
<220> FEATURE:
<221> NAME/KEY: VARIANT
<222> LOCATION: (87)...(94)

<400> SEQUENCE: 58

Ile Asn Asp Ser Gly Val Asn Asn
 1               5

<210> SEQ ID NO 59
<211> LENGTH: 5
<212> TYPE: PRT
<213> ORGANISM: Unknown
<220> FEATURE:
<221> NAME/KEY: VARIANT
<222> LOCATION: (146)...(150)

<400> SEQUENCE: 59

Ser Asp Gln Pro Ser
 1               5

<210> SEQ ID NO 60
<211> LENGTH: 4
<212> TYPE: PRT
<213> ORGANISM: Unknown
<220> FEATURE:
<221> NAME/KEY: VARIANT
<222> LOCATION: (145)...(148)

<400> SEQUENCE: 60

Ala Glu Leu Ala
 1

<210> SEQ ID NO 61
<211> LENGTH: 4
<212> TYPE: PRT
<213> ORGANISM: Unknown
<220> FEATURE:
<221> NAME/KEY: VARIANT
<222> LOCATION: (145)...(148)

<400> SEQUENCE: 61

Ala Glu Trp Ala
 1

<210> SEQ ID NO 62
<211> LENGTH: 8
<212> TYPE: PRT
<213> ORGANISM: Unknown
<220> FEATURE:
<221> NAME/KEY: VARIANT
<222> LOCATION: (87)...(94)

<400> SEQUENCE: 62
```

```
Ile Asn Tyr Ser Gly Val Asn Asn
1               5
```

<210> SEQ ID NO 63
<211> LENGTH: 4
<212> TYPE: PRT
<213> ORGANISM: Unknown
<220> FEATURE:
<221> NAME/KEY: VARIANT
<222> LOCATION: (145)...(148)

<400> SEQUENCE: 63

```
Leu Glu Thr Asn
1
```

<210> SEQ ID NO 64
<211> LENGTH: 6
<212> TYPE: PRT
<213> ORGANISM: Unknown
<220> FEATURE:
<221> NAME/KEY: VARIANT
<222> LOCATION: (143)...(148)

<400> SEQUENCE: 64

```
Gly Arg Pro Ala Ala Ala
1               5
```

<210> SEQ ID NO 65
<211> LENGTH: 34
<212> TYPE: DNA
<213> ORGANISM: Artificial sequence
<220> FEATURE:
<223> OTHER INFORMATION: nucleotide

<400> SEQUENCE: 65
gcatcatcaa tgattccgga gtaaacaaca cggc                          34

<210> SEQ ID NO 66
<211> LENGTH: 8
<212> TYPE: PRT
<213> ORGANISM: Unknown
<220> FEATURE:
<221> NAME/KEY: VARIANT
<222> LOCATION: (87)...(94)

<400> SEQUENCE: 66

```
Ile Lys Asp Ser Gly Val Asn Asn
1               5
```

<210> SEQ ID NO 67
<211> LENGTH: 26
<212> TYPE: DNA
<213> ORGANISM: Artificial sequence
<220> FEATURE:
<223> OTHER INFORMATION: nucleotide

<400> SEQUENCE: 67
ttaccgtaat ttatatgact tagcag                                   26

<210> SEQ ID NO 68
<211> LENGTH: 28
<212> TYPE: DNA
<213> ORGANISM: Artificial sequence
<220> FEATURE:
<223> OTHER INFORMATION: nucleotide

<400> SEQUENCE: 68
cgtaatttat tctcgctagc agatttag                                 28

-continued

```
<210> SEQ ID NO 69
<211> LENGTH: 33
<212> TYPE: DNA
<213> ORGANISM: Artificial sequence
<220> FEATURE:
<223> OTHER INFORMATION: nucleotide

<400> SEQUENCE: 69
cactgttcct tcgaacgcgt aaccttaaat acc                                33

<210> SEQ ID NO 70
<211> LENGTH: 686
<212> TYPE: PRT
<213> ORGANISM: Bacillus circulans

<400> SEQUENCE: 70
```

| Ala | Pro | Asp | Thr | Ser | Val | Ser | Asn | Lys | Gln | Asn | Phe | Ser | Thr | Asp | Val |
|---|---|---|---|---|---|---|---|---|---|---|---|---|---|---|---|
| 1 | | | | 5 | | | | | 10 | | | | | 15 | |

| Ile | Tyr | Gln | Ile | Phe | Thr | Asp | Arg | Phe | Ser | Asp | Gly | Asn | Pro | Ala | Asn |
|---|---|---|---|---|---|---|---|---|---|---|---|---|---|---|---|
| | | | 20 | | | | | 25 | | | | | 30 | | |

| Asn | Pro | Thr | Gly | Ala | Ala | Phe | Asp | Gly | Thr | Cys | Thr | Asn | Leu | Arg | Leu |
|---|---|---|---|---|---|---|---|---|---|---|---|---|---|---|---|
| | | 35 | | | | | 40 | | | | | 45 | | | |

| Tyr | Cys | Gly | Gly | Asp | Trp | Gln | Gly | Ile | Ile | Asn | Lys | Ile | Asn | Asp | Gly |
|---|---|---|---|---|---|---|---|---|---|---|---|---|---|---|---|
| | 50 | | | | | 55 | | | | | 60 | | | | |

| Tyr | Leu | Thr | Gly | Met | Gly | Val | Thr | Ala | Ile | Trp | Ile | Ser | Gln | Pro | Val |
|---|---|---|---|---|---|---|---|---|---|---|---|---|---|---|---|
| 65 | | | | | 70 | | | | | 75 | | | | | 80 |

| Glu | Asn | Ile | Tyr | Ser | Ile | Ile | Asn | Tyr | Ser | Gly | Val | Asn | Asn | Thr | Ala |
|---|---|---|---|---|---|---|---|---|---|---|---|---|---|---|---|
| | | | | 85 | | | | | 90 | | | | | 95 | |

| Tyr | His | Gly | Tyr | Trp | Ala | Arg | Asp | Phe | Lys | Lys | Thr | Asn | Pro | Ala | Tyr |
|---|---|---|---|---|---|---|---|---|---|---|---|---|---|---|---|
| | | | 100 | | | | | 105 | | | | | 110 | | |

| Gly | Thr | Ile | Ala | Asp | Phe | Gln | Asn | Leu | Ile | Ala | Ala | His | Ala | Lys |
|---|---|---|---|---|---|---|---|---|---|---|---|---|---|---|
| | | 115 | | | | | 120 | | | | | 125 | | |

| Asn | Ile | Lys | Val | Ile | Ile | Asp | Phe | Ala | Pro | Asn | His | Thr | Ser | Pro | Ala |
|---|---|---|---|---|---|---|---|---|---|---|---|---|---|---|---|
| 130 | | | | | 135 | | | | | 140 | | | | | |

| Ser | Ser | Asp | Gln | Pro | Ser | Phe | Ala | Glu | Asn | Gly | Arg | Leu | Tyr | Asp | Asn |
|---|---|---|---|---|---|---|---|---|---|---|---|---|---|---|---|
| 145 | | | | | 150 | | | | | 155 | | | | | 160 |

| Gly | Thr | Leu | Leu | Gly | Gly | Tyr | Thr | Asn | Asp | Thr | Gln | Asn | Leu | Phe | His |
|---|---|---|---|---|---|---|---|---|---|---|---|---|---|---|---|
| | | | | 165 | | | | | 170 | | | | | 175 | |

| His | Asn | Gly | Gly | Thr | Asp | Phe | Ser | Thr | Thr | Glu | Asn | Gly | Ile | Tyr | Lys |
|---|---|---|---|---|---|---|---|---|---|---|---|---|---|---|---|
| | | | 180 | | | | | 185 | | | | | 190 | | |

| Asn | Leu | Tyr | Asp | Leu | Ala | Asp | Leu | Asn | His | Asn | Asn | Ser | Thr | Val | Asp |
|---|---|---|---|---|---|---|---|---|---|---|---|---|---|---|---|
| | | | 195 | | | | | 200 | | | | | 205 | | |

| Val | Tyr | Leu | Lys | Asp | Ala | Ile | Lys | Met | Trp | Leu | Asp | Leu | Gly | Ile | Asp |
|---|---|---|---|---|---|---|---|---|---|---|---|---|---|---|---|
| | 210 | | | | | 215 | | | | | 220 | | | | |

| Gly | Ile | Arg | Met | Asp | Ala | Val | Lys | His | Met | Pro | Phe | Gly | Trp | Gln | Lys |
|---|---|---|---|---|---|---|---|---|---|---|---|---|---|---|---|
| 225 | | | | | 230 | | | | | 235 | | | | | 240 |

| Ser | Phe | Met | Ala | Ala | Val | Asn | Asn | Tyr | Lys | Pro | Val | Phe | Thr | Phe | Gly |
|---|---|---|---|---|---|---|---|---|---|---|---|---|---|---|---|
| | | | | 245 | | | | | 250 | | | | | 255 | |

| Glu | Trp | Phe | Leu | Gly | Val | Asn | Glu | Val | Ser | Pro | Glu | Asn | His | Lys | Phe |
|---|---|---|---|---|---|---|---|---|---|---|---|---|---|---|---|
| | | | 260 | | | | | 265 | | | | | 270 | | |

| Ala | Asn | Glu | Ser | Gly | Met | Ser | Leu | Leu | Asp | Phe | Arg | Phe | Ala | Gln | Lys |
|---|---|---|---|---|---|---|---|---|---|---|---|---|---|---|---|
| | | 275 | | | | | 280 | | | | | 285 | | | |

| Val | Arg | Gln | Val | Phe | Arg | Asp | Asn | Thr | Asp | Asn | Met | Tyr | Gly | Leu | Lys |
|---|---|---|---|---|---|---|---|---|---|---|---|---|---|---|---|
| | 290 | | | | | 295 | | | | | 300 | | | | |

| Ala | Met | Leu | Glu | Gly | Ser | Ala | Ala | Asp | Tyr | Ala | Gln | Val | Asp | Asp | Gln |
|---|---|---|---|---|---|---|---|---|---|---|---|---|---|---|---|
| 305 | | | | | 310 | | | | | 315 | | | | | 320 |

-continued

```
Val Thr Phe Ile Asp Asn His Asp Met Glu Arg Phe His Ala Ser Asn
            325                 330                 335

Ala Asn Arg Arg Lys Leu Glu Gln Ala Leu Ala Phe Thr Leu Thr Ser
            340                 345                 350

Arg Gly Val Pro Ala Ile Tyr Tyr Gly Thr Glu Gln Tyr Met Ser Gly
            355                 360                 365

Gly Thr Asp Pro Asp Asn Arg Ala Arg Ile Pro Ser Phe Ser Thr Ser
            370                 375                 380

Thr Thr Ala Tyr Gln Val Ile Gln Lys Leu Ala Pro Leu Arg Lys Cys
385                 390                 395                 400

Asn Pro Ala Ile Ala Tyr Gly Ser Thr Gln Glu Arg Trp Ile Asn Asn
            405                 410                 415

Asp Val Leu Ile Tyr Glu Arg Lys Phe Gly Ser Asn Val Ala Val Val
            420                 425                 430

Ala Val Asn Arg Asn Leu Asn Ala Pro Ala Ser Ile Ser Gly Leu Val
            435                 440                 445

Thr Ser Leu Pro Gln Gly Ser Tyr Asn Asp Val Leu Gly Gly Leu Leu
            450                 455                 460

Asn Gly Asn Thr Leu Ser Val Gly Ser Gly Gly Ala Ala Ser Asn Phe
465                 470                 475                 480

Thr Leu Ala Ala Gly Gly Thr Ala Val Trp Gln Tyr Thr Ala Ala Thr
            485                 490                 495

Ala Thr Pro Thr Ile Gly His Val Gly Pro Met Met Ala Lys Pro Gly
            500                 505                 510

Val Thr Ile Thr Ile Asp Gly Arg Gly Phe Gly Ser Ser Lys Gly Thr
            515                 520                 525

Val Tyr Phe Gly Thr Thr Ala Val Ser Gly Ala Asp Ile Thr Ser Trp
            530                 535                 540

Glu Asp Thr Gln Ile Lys Val Lys Ile Pro Ala Val Ala Gly Gly Asn
545                 550                 555                 560

Tyr Asn Ile Lys Val Ala Asn Ala Ala Gly Thr Ala Ser Asn Val Tyr
            565                 570                 575

Asp Asn Phe Glu Val Leu Ser Gly Asp Gln Val Ser Val Arg Phe Val
            580                 585                 590

Val Asn Asn Ala Thr Thr Ala Leu Gly Gln Asn Val Tyr Leu Thr Gly
            595                 600                 605

Ser Val Ser Glu Leu Gly Asn Trp Asp Pro Ala Lys Ala Ile Gly Pro
            610                 615                 620

Met Tyr Asn Gln Val Val Tyr Gln Tyr Pro Asn Trp Tyr Tyr Asp Val
625                 630                 635                 640

Ser Val Pro Ala Gly Lys Thr Ile Glu Phe Lys Phe Leu Lys Lys Gln
            645                 650                 655

Gly Ser Thr Val Thr Trp Glu Gly Gly Ser Asn His Thr Phe Thr Ala
            660                 665                 670

Pro Ser Ser Gly Thr Ala Thr Ile Asn Val Asn Trp Gln Pro
            675                 680                 685

<210> SEQ ID NO 71
<211> LENGTH: 676
<212> TYPE: PRT
<213> ORGANISM: Bacillus sp.

<400> SEQUENCE: 71

Glu Ala Asp Val Thr Asn Lys Val Asn Tyr Ser Lys Asp Val Ile Tyr
1               5                   10                  15
```

```
Gln Ile Val Thr Asp Arg Phe Ser Asp Gly Asn Pro Gly Asn Pro
             20                  25                  30

Ser Gly Ala Ile Phe Ser Gln Asn Cys Ile Asp Leu His Lys Tyr Cys
         35                  40                  45

Gly Gly Asp Trp Gln Gly Ile Ile Asp Lys Ile Asn Asp Gly Tyr Leu
     50                  55                  60

Thr Asp Leu Gly Ile Thr Ala Leu Trp Ile Ser Gln Pro Val Glu Asn
65                  70                  75                  80

Val Tyr Ala Leu His Pro Ser Gly Tyr Thr Ser Tyr His Gly Tyr Trp
                 85                  90                  95

Ala Arg Asp Tyr Lys Lys Thr Asn Pro Tyr Tyr Gly Asn Phe Asp Asp
             100                 105                 110

Phe Asp Arg Leu Met Ser Thr Ala His Ser Asn Gly Ile Lys Val Ile
         115                 120                 125

Met Asp Phe Thr Pro Asn His Ser Ser Pro Ala Leu Glu Thr Asn Pro
130                 135                 140

Asn Tyr Val Glu Asn Gly Ala Ile Tyr Asp Asn Gly Ala Leu Leu Gly
145                 150                 155                 160

Asn Tyr Ser Asn Asp Gln Gln Asn Leu Phe His Asn Gly Gly Thr
                 165                 170                 175

Asp Phe Ser Ser Tyr Glu Asp Ser Ile Tyr Arg Asn Leu Tyr Asp Leu
             180                 185                 190

Ala Asp Tyr Asp Leu Asn Asn Thr Val Met Asp Gln Tyr Leu Lys Glu
             195                 200                 205

Ser Ile Lys Phe Trp Leu Asp Lys Gly Ile Asp Gly Ile Arg Val Asp
     210                 215                 220

Ala Val Lys His Met Ser Glu Gly Trp Gln Thr Ser Leu Met Ser Glu
225                 230                 235                 240

Ile Tyr Ser His Lys Pro Val Phe Thr Phe Gly Glu Trp Phe Leu Gly
             245                 250                 255

Ser Gly Glu Val Asp Pro Gln Asn His His Phe Ala Asn Glu Ser Gly
             260                 265                 270

Met Ser Leu Leu Asp Phe Gln Phe Gly Gln Thr Ile Arg Asn Val Leu
     275                 280                 285

Lys Asp Arg Thr Ser Asn Trp Tyr Asp Phe Asn Glu Met Ile Thr Ser
290                 295                 300

Thr Glu Lys Glu Tyr Asn Glu Val Ile Asp Gln Val Thr Phe Ile Asp
305                 310                 315                 320

Asn His Asp Met Ser Arg Phe Ser Val Gly Ser Ser Asn Arg Gln
                 325                 330                 335

Thr Asp Met Ala Leu Ala Val Leu Leu Thr Ser Arg Gly Val Pro Thr
             340                 345                 350

Ile Tyr Tyr Gly Thr Glu Gln Tyr Val Thr Gly Gly Asn Asp Pro Glu
     355                 360                 365

Asn Arg Lys Pro Leu Lys Thr Phe Asp Arg Ser Thr Asn Ser Tyr Gln
370                 375                 380

Ile Ile Ser Lys Leu Ala Ser Leu Arg Gln Thr Asn Ser Ala Leu Gly
385                 390                 395                 400

Tyr Gly Thr Thr Thr Glu Arg Trp Leu Asn Glu Asp Ile Tyr Ile Tyr
                 405                 410                 415

Glu Arg Thr Phe Gly Asn Ser Ile Val Leu Thr Ala Val Asn Ser Ser
             420                 425                 430

Asn Ser Asn Gln Thr Ile Thr Asn Leu Asn Thr Ser Leu Pro Gln Gly
```

-continued

```
                435                 440                 445
Asn Tyr Thr Asp Glu Leu Gln Gln Arg Leu Asp Gly Asn Thr Ile Thr
    450                 455                 460

Val Asn Ala Asn Gly Ala Val Asn Ser Phe Gln Leu Arg Ala Asn Ser
465                 470                 475                 480

Val Ala Val Trp Gln Val Ser Asn Pro Ser Thr Ser Pro Leu Ile Gly
                485                 490                 495

Gln Val Gly Pro Met Met Gly Lys Ala Gly Asn Thr Ile Thr Val Ser
            500                 505                 510

Gly Glu Gly Phe Gly Asp Glu Arg Gly Ser Val Leu Phe Asp Ser Thr
            515                 520                 525

Ser Ser Glu Ile Ile Ser Trp Ser Asn Thr Lys Ile Ser Val Lys Val
530                 535                 540

Pro Asn Val Ala Gly Gly Tyr Tyr Asp Leu Ser Val Val Thr Ala Ala
545                 550                 555                 560

Asn Ile Lys Ser Pro Thr Tyr Lys Glu Phe Glu Val Leu Ser Gly Asn
                565                 570                 575

Gln Val Ser Val Arg Phe Gly Val Asn Asn Ala Thr Thr Ser Pro Gly
            580                 585                 590

Thr Asn Leu Tyr Ile Val Gly Asn Val Asn Glu Leu Gly Asn Trp Asp
            595                 600                 605

Ala Asp Lys Ala Ile Gly Pro Met Phe Asn Gln Val Met Tyr Gln Tyr
    610                 615                 620

Pro Thr Trp Tyr Tyr Asp Ile Ser Val Pro Ala Gly Lys Asn Leu Glu
625                 630                 635                 640

Tyr Lys Tyr Ile Lys Lys Asp Gln Asn Gly Asn Val Val Trp Gln Ser
                645                 650                 655

Gly Asn Asn Arg Thr Tyr Thr Ser Pro Thr Thr Gly Thr Asp Thr Val
            660                 665                 670

Met Ile Asn Trp
            675

<210> SEQ ID NO 72
<211> LENGTH: 685
<212> TYPE: PRT
<213> ORGANISM: Bacillus sp.

<400> SEQUENCE: 72

Ala Pro Asp Thr Ser Val Ser Asn Lys Gln Asn Phe Ser Thr Asp Val
1               5                   10                  15

Ile Tyr Gln Ile Phe Thr Asp Arg Phe Ser Asp Gly Asn Pro Ala Asn
                20                  25                  30

Asn Pro Thr Gly Ala Ala Phe Asp Gly Ser Cys Thr Asn Leu Arg Leu
            35                  40                  45

Tyr Cys Gly Gly Asp Trp Gln Gly Ile Ile Asn Lys Ile Asn Asp Gly
    50                  55                  60

Tyr Leu Thr Gly Met Gly Ile Thr Ala Ile Trp Ile Ser Gln Pro Val
65                  70                  75                  80

Glu Asn Ile Tyr Ser Val Ile Asn Tyr Ser Gly Val His Asn Thr Ala
                85                  90                  95

Tyr His Gly Tyr Trp Ala Arg Asp Phe Lys Lys Thr Asn Pro Ala Tyr
            100                 105                 110

Gly Thr Met Gln Asp Phe Lys Asn Leu Ile Asp Thr Ala His Ala His
            115                 120                 125

Asn Ile Lys Val Ile Ile Asp Phe Ala Pro Asn His Thr Ser Pro Ala
```

```
                130                 135                 140
Ser Ser Asp Asp Pro Ser Phe Ala Glu Asn Gly Arg Leu Tyr Asp Asn
145                 150                 155                 160

Gly Asn Leu Leu Gly Gly Tyr Thr Asn Asp Thr Gln Asn Leu Phe His
                165                 170                 175

His Tyr Gly Gly Thr Asp Phe Ser Thr Ile Glu Asn Gly Ile Tyr Lys
                180                 185                 190

Asn Leu Tyr Asp Leu Ala Asp Leu Asn His Asn Asn Ser Ser Val Asp
                195                 200                 205

Val Tyr Leu Lys Asp Ala Ile Lys Met Trp Leu Asp Leu Gly Val Asp
210                 215                 220

Gly Ile Arg Val Asp Ala Val Lys His Met Pro Phe Gly Trp Gln Lys
225                 230                 235                 240

Ser Phe Met Ser Thr Ile Asn Asn Tyr Lys Pro Val Phe Asn Phe Gly
                245                 250                 255

Glu Trp Phe Leu Gly Val Asn Glu Ile Ser Pro Glu Tyr His Gln Phe
                260                 265                 270

Ala Asn Glu Ser Gly Met Ser Leu Leu Asp Phe Pro Phe Ala Gln Lys
                275                 280                 285

Ala Arg Gln Val Phe Arg Asp Asn Thr Asp Asn Met Tyr Gly Leu Lys
                290                 295                 300

Ala Met Leu Glu Gly Ser Glu Val Asp Tyr Ala Gln Val Asn Asp Gln
305                 310                 315                 320

Val Thr Phe Ile Asp Asn His Asp Met Glu Arg Phe His Thr Ser Asn
                325                 330                 335

Gly Asp Arg Arg Lys Leu Glu Gln Ala Leu Ala Phe Thr Leu Thr Ser
                340                 345                 350

Arg Gly Val Pro Ala Ile Tyr Tyr Gly Ser Glu Gln Tyr Met Ser Gly
                355                 360                 365

Gly Asn Asp Pro Asp Asn Arg Ala Arg Ile Pro Ser Phe Ser Thr Thr
                370                 375                 380

Thr Thr Ala Tyr Gln Val Ile Gln Lys Leu Ala Pro Leu Arg Lys Ser
385                 390                 395                 400

Asn Pro Ala Ile Ala Tyr Gly Ser Thr Gln Glu Arg Trp Ile Asn Asn
                405                 410                 415

Asp Val Ile Ile Tyr Glu Arg Lys Phe Gly Asn Asn Val Ala Val Val
                420                 425                 430

Ala Ile Asn Arg Asn Met Asn Thr Pro Ala Ser Ile Thr Gly Leu Val
                435                 440                 445

Thr Ser Leu Pro Gln Gly Ser Tyr Asn Asp Val Leu Gly Gly Ile Leu
450                 455                 460

Asn Gly Asn Thr Leu Thr Val Gly Ala Gly Gly Ala Ala Ser Asn Phe
465                 470                 475                 480

Thr Leu Ala Pro Gly Gly Thr Ala Val Trp Gln Tyr Thr Thr Asp Ala
                485                 490                 495

Thr Ala Pro Ile Asn Gly Asn Val Gly Pro Met Met Ala Lys Ala Gly
                500                 505                 510

Val Thr Ile Thr Ile Asp Gly Arg Ala Ser Ala Arg Gln Gly Thr Val
                515                 520                 525

Tyr Phe Gly Thr Thr Ala Val Thr Gly Ala Asp Ile Val Ala Trp Glu
                530                 535                 540

Asp Thr Gln Ile Gln Val Lys Ile Leu Arg Val Pro Gly Gly Ile Tyr
545                 550                 555                 560
```

-continued

```
Asp Ile Arg Val Ala Asn Ala Gly Ala Ser Asn Ile Tyr Asp
            565                 570                 575

Asn Phe Glu Val Leu Thr Gly Asp Gln Val Thr Val Arg Phe Val Ile
            580                 585                 590

Asn Asn Ala Thr Thr Ala Leu Gly Gln Asn Val Phe Leu Thr Gly Asn
            595                 600                 605

Val Ser Glu Leu Gly Asn Trp Asp Pro Asn Asn Ala Ile Gly Pro Met
610                 615                 620

Tyr Asn Gln Val Val Tyr Gln Tyr Pro Thr Trp Tyr Tyr Asp Val Ser
625                 630                 635                 640

Val Pro Ala Gly Gln Thr Ile Glu Phe Lys Phe Leu Lys Lys Gln Gly
            645                 650                 655

Ser Thr Val Thr Trp Glu Gly Gly Ala Asn Arg Thr Phe Thr Thr Pro
            660                 665                 670

Thr Ser Gly Thr Ala Thr Val Asn Val Asn Trp Gln Pro
            675                 680                 685
```

<210> SEQ ID NO 73
<211> LENGTH: 686
<212> TYPE: PRT
<213> ORGANISM: Bacillus sp.

<400> SEQUENCE: 73

```
Ala Pro Asp Thr Ser Val Ser Asn Lys Gln Asn Phe Ser Thr Asp Val
1               5                   10                  15

Ile Tyr Gln Ile Phe Thr Asp Arg Phe Ser Asp Gly Asn Pro Ala Asn
                20                  25                  30

Asn Pro Thr Gly Ala Ala Phe Asp Gly Ser Cys Thr Asn Leu Arg Leu
            35                  40                  45

Tyr Cys Gly Gly Asp Trp Gln Gly Ile Ile Asn Lys Ile Asn Asp Gly
        50                  55                  60

Tyr Leu Thr Gly Met Gly Ile Thr Ala Ile Trp Ile Ser Gln Pro Val
65                  70                  75                  80

Glu Asn Ile Tyr Ser Val Ile Asn Tyr Ser Gly Val Asn Asn Thr Ala
                85                  90                  95

Tyr His Gly Tyr Trp Ala Arg Asp Phe Lys Lys Thr Asn Pro Ala Tyr
            100                 105                 110

Gly Thr Met Gln Asp Phe Lys Asn Leu Ile Asp Thr Ala His Ala His
        115                 120                 125

Asn Ile Lys Val Ile Ile Asp Phe Ala Pro Asn His Thr Ser Pro Ala
    130                 135                 140

Ser Ser Asp Asp Pro Ser Phe Ala Glu Asn Gly Arg Leu Tyr Asp Asn
145                 150                 155                 160

Gly Asn Leu Leu Gly Gly Tyr Thr Asn Asp Thr Gln Asn Leu Phe His
                165                 170                 175

His Tyr Gly Gly Thr Asp Phe Ser Thr Ile Glu Asn Gly Ile Tyr Lys
            180                 185                 190

Asn Leu Tyr Asp Leu Ala Asp Leu Asn His Asn Ser Ser Val Asp
        195                 200                 205

Val Tyr Leu Lys Asp Ala Ile Lys Met Trp Leu Asp Leu Gly Val Asp
    210                 215                 220

Gly Ile Arg Val Asp Ala Val Lys His Met Pro Phe Gly Trp Gln Lys
225                 230                 235                 240

Ser Phe Met Ala Thr Ile Asn Asn Tyr Lys Pro Val Phe Thr Phe Gly
                245                 250                 255
```

-continued

Glu Trp Phe Leu Gly Val Asn Glu Ile Ser Pro Glu Tyr His Gln Phe
        260                 265                 270

Ala Asn Glu Ser Gly Met Ser Leu Leu Asp Phe Arg Phe Ala Gln Lys
        275                 280                 285

Ala Arg Gln Val Phe Arg Asp Asn Thr Asp Asn Met Tyr Gly Leu Lys
290                 295                 300

Ala Met Leu Glu Gly Ser Glu Val Asp Tyr Ala Gln Val Asn Asp Gln
305                 310                 315                 320

Val Thr Phe Ile Asp Asn His Asp Met Glu Arg Phe His Thr Ser Asn
                325                 330                 335

Gly Asp Arg Arg Lys Leu Glu Gln Ala Leu Ala Phe Thr Leu Thr Ser
                340                 345                 350

Arg Gly Val Pro Ala Ile Tyr Tyr Gly Ser Glu Gln Tyr Met Ser Gly
        355                 360                 365

Gly Asn Asp Pro Asp Asn Arg Ala Arg Leu Pro Ser Phe Ser Thr Thr
        370                 375                 380

Thr Thr Ala Tyr Gln Val Ile Gln Lys Leu Ala Pro Leu Arg Lys Ser
385                 390                 395                 400

Asn Pro Ala Ile Ala Tyr Gly Ser Thr His Glu Arg Trp Ile Asn Asn
                405                 410                 415

Asp Val Ile Ile Tyr Glu Arg Lys Phe Gly Asn Asn Val Ala Val Val
                420                 425                 430

Ala Ile Asn Arg Asn Met Asn Thr Pro Ala Ser Ile Thr Gly Leu Val
                435                 440                 445

Thr Ser Leu Arg Arg Ala Ser Tyr Asn Asp Val Leu Gly Gly Ile Leu
        450                 455                 460

Asn Gly Asn Thr Leu Thr Val Gly Ala Gly Gly Ala Ala Ser Asn Phe
465                 470                 475                 480

Thr Leu Ala Pro Gly Gly Thr Ala Val Trp Gln Tyr Thr Thr Asp Ala
                485                 490                 495

Thr Thr Pro Ile Ile Gly Asn Val Gly Pro Met Met Ala Lys Pro Gly
                500                 505                 510

Val Thr Ile Thr Ile Asp Gly Arg Gly Phe Gly Ser Gly Lys Gly Thr
                515                 520                 525

Val Tyr Phe Gly Thr Thr Ala Val Thr Gly Ala Asp Ile Val Ala Trp
        530                 535                 540

Glu Asp Thr Gln Ile Gln Val Lys Ile Pro Ala Val Pro Gly Gly Ile
545                 550                 555                 560

Tyr Asp Ile Arg Val Ala Asn Ala Ala Gly Ala Ala Ser Asn Ile Tyr
                565                 570                 575

Asp Asn Phe Glu Val Leu Thr Gly Asp Gln Val Thr Val Arg Phe Val
                580                 585                 590

Ile Asn Asn Ala Thr Thr Ala Leu Gly Gln Asn Val Phe Leu Thr Gly
                595                 600                 605

Asn Val Ser Glu Leu Gly Asn Trp Asp Pro Asn Asn Ala Ile Gly Pro
610                 615                 620

Met Tyr Asn Gln Val Val Tyr Gln Tyr Pro Thr Trp Tyr Tyr Asp Val
625                 630                 635                 640

Ser Val Pro Ala Gly Gln Thr Ile Glu Phe Lys Phe Leu Lys Lys Gln
                645                 650                 655

Gly Ser Thr Val Thr Trp Glu Gly Gly Ala Asn Arg Thr Phe Thr Thr
                660                 665                 670

Pro Thr Ser Gly Thr Ala Thr Val Asn Val Asn Trp Gln Pro
                675                 680                 685

<210> SEQ ID NO 74
<211> LENGTH: 685
<212> TYPE: PRT
<213> ORGANISM: Bacillus licheniformis

<400> SEQUENCE: 74

```
Ala Asp Ala Asp Thr Ala Val Thr Asn Lys Gln Asn Phe Ser Thr Asp
  1               5                  10                  15

Val Ile Tyr Gln Val Phe Thr Asp Arg Phe Leu Asp Gly Asn Pro Ser
             20                  25                  30

Asn Asn Pro Thr Gly Ala Ala Phe Asp Gly Thr Cys Ser Asn Leu Lys
         35                  40                  45

Leu Tyr Cys Gly Gly Asp Trp Gln Gly Leu Val Asn Lys Ile Asn Asp
 50                  55                  60

Asn Tyr Phe Ser Asp Leu Gly Val Thr Ala Leu Trp Ile Ser Gln Pro
 65                  70                  75                  80

Val Glu Asn Ile Phe Ala Thr Ile Asn Tyr Ser Gly Val Thr Asn Thr
                 85                  90                  95

Ala Tyr His Gly Tyr Trp Ala Arg Asp Phe Lys Lys Thr Asn Pro Tyr
            100                 105                 110

Phe Gly Thr Met Thr Asp Phe Gln Asn Leu Val Thr Thr Ala His Ala
        115                 120                 125

Lys Gly Ile Lys Ile Ile Ile Asp Phe Ala Pro Asn His Thr Ser Pro
130                 135                 140

Ala Met Glu Thr Asp Thr Ser Phe Ala Glu Asn Gly Lys Leu Tyr Asp
145                 150                 155                 160

Asn Gly Asn Leu Val Gly Gly Tyr Thr Asn Asp Thr Asn Gly Tyr Phe
                165                 170                 175

His His Asn Gly Gly Ser Asp Phe Ser Thr Leu Glu Asn Gly Ile Tyr
            180                 185                 190

Lys Asn Leu Tyr Asp Leu Ala Asp Leu Asn His Asn Asn Ser Thr Ile
        195                 200                 205

Asp Thr Tyr Phe Lys Asp Ala Ile Lys Leu Trp Leu Asp Met Gly Val
    210                 215                 220

Asp Gly Ile Arg Val Asp Ala Val Lys His Met Pro Gln Gly Trp Gln
225                 230                 235                 240

Lys Asn Trp Met Ser Ser Ile Tyr Ala His Lys Pro Val Phe Thr Phe
                245                 250                 255

Gly Glu Trp Phe Leu Gly Ser Ala Ala Pro Asp Ala Asp Asn Thr Asp
            260                 265                 270

Phe Ala Asn Glu Ser Gly Met Ser Leu Leu Asp Phe Arg Phe Asn Ser
        275                 280                 285

Ala Val Arg Asn Val Phe Arg Asp Asn Thr Ser Asn Met Tyr Ala Leu
    290                 295                 300

Asp Ser Met Leu Thr Ala Thr Ala Asp Tyr Asn Gln Val Asn Asp
305                 310                 315                 320

Gln Val Thr Phe Ile Asp Asn His Asp Met Asp Arg Phe Lys Thr Ser
                325                 330                 335

Ala Val Asn Asn Arg Arg Leu Glu Gln Ala Leu Ala Phe Thr Leu Thr
            340                 345                 350

Ser Arg Gly Val Pro Ala Ile Tyr Tyr Gly Thr Glu Gln Tyr Leu Thr
        355                 360                 365

Gly Asn Gly Asp Pro Asp Asn Arg Gly Lys Met Pro Ser Phe Ser Lys
    370                 375                 380
```

-continued

```
Ser Thr Thr Ala Phe Asn Val Ile Ser Lys Leu Ala Pro Leu Arg Lys
385                 390                 395                 400

Ser Asn Pro Ala Ile Ala Tyr Gly Ser Thr Gln Gln Arg Trp Ile Asn
            405                 410                 415

Asn Asp Val Tyr Ile Tyr Glu Arg Lys Phe Gly Lys Ser Val Ala Val
            420                 425                 430

Val Ala Val Asn Arg Asn Leu Thr Thr Pro Thr Ser Ile Thr Asn Leu
            435                 440                 445

Asn Thr Ser Leu Pro Ser Gly Thr Tyr Thr Asp Val Leu Gly Gly Val
        450                 455                 460

Leu Asn Gly Asn Asn Ile Thr Ser Ser Gly Gly Asn Ile Ser Ser Phe
465                 470                 475                 480

Thr Leu Ala Ala Gly Ala Thr Ala Val Trp Gln Tyr Thr Ala Ser Glu
                485                 490                 495

Thr Thr Pro Thr Ile Gly His Val Gly Pro Val Met Gly Lys Pro Gly
                500                 505                 510

Asn Val Val Thr Ile Asp Gly Arg Gly Phe Gly Ser Ala Lys Gly Thr
            515                 520                 525

Val Tyr Phe Gly Thr Thr Ala Val Thr Gly Ser Ala Ile Thr Ser Trp
        530                 535                 540

Glu Asp Thr Gln Ile Lys Val Thr Ile Pro Pro Val Ala Gly Gly Asp
545                 550                 555                 560

Tyr Ala Val Lys Val Ala Ala Asn Gly Val Asn Ser Asn Ala Tyr Asn
                565                 570                 575

Asp Phe Thr Ile Leu Ser Gly Asp Gln Val Ser Val Arg Phe Val Ile
            580                 585                 590

Asn Asn Ala Thr Thr Ala Leu Gly Glu Asn Ile Tyr Leu Thr Gly Asn
            595                 600                 605

Val Ser Glu Leu Gly Asn Trp Thr Thr Gly Ala Ala Ser Ile Gly Pro
        610                 615                 620

Ala Phe Asn Gln Val Ile His Ala Tyr Pro Thr Trp Tyr Tyr Asp Val
625                 630                 635                 640

Ser Val Pro Ala Gly Lys Gln Leu Glu Phe Lys Phe Lys Lys Asn
            645                 650                 655

Gly Ala Thr Ile Thr Trp Glu Gly Gly Ser Asn His Thr Phe Thr Thr
                660                 665                 670

Pro Thr Ser Gly Thr Ala Thr Val Thr Ile Asn Trp Gln
        675                 680                 685

<210> SEQ ID NO 75
<211> LENGTH: 687
<212> TYPE: PRT
<213> ORGANISM: Bacillus macerans

<400> SEQUENCE: 75

Ser Pro Asp Thr Ser Val Asp Asn Lys Val Asn Phe Ser Thr Asp Val
1               5                   10                  15

Ile Tyr Gln Ile Val Thr Asp Arg Phe Ala Asp Gly Asp Arg Thr Asn
            20                  25                  30

Asn Pro Ala Gly Asp Ala Phe Ser Gly Asp Arg Ser Asn Leu Lys Leu
        35                  40                  45

Tyr Phe Gly Gly Asp Trp Gln Gly Ile Ile Asp Lys Ile Asn Asp Gly
    50                  55                  60

Tyr Leu Thr Gly Met Gly Val Thr Ala Leu Trp Ile Ser Gln Pro Val
65                  70                  75                  80
```

-continued

Glu Asn Ile Thr Ser Val Ile Lys Tyr Ser Gly Val Asn Asn Thr Ser
                85                  90                  95

Tyr His Gly Tyr Trp Ala Arg Asp Phe Lys Gln Thr Asn Asp Ala Phe
            100                 105                 110

Gly Asp Phe Ala Asp Phe Gln Asn Leu Ile Asp Thr Ala His Ala His
            115                 120                 125

Asn Ile Lys Val Val Ile Asp Phe Ala Pro Asn His Thr Ser Pro Ala
130                 135                 140

Asp Arg Asp Asn Pro Gly Phe Ala Glu Asn Gly Met Tyr Asp Asn
145                 150                 155                 160

Gly Ser Leu Leu Gly Ala Tyr Ser Asn Asp Thr Ala Gly Leu Phe His
            165                 170                 175

His Asn Gly Gly Thr Asp Phe Ser Thr Ile Glu Asp Gly Ile Tyr Lys
            180                 185                 190

Asn Leu Tyr Asp Leu Ala Asp Ile Asn His Asn Asn Ala Met Asp
            195                 200                 205

Ala Tyr Phe Lys Ser Ala Ile Asp Leu Trp Leu Gly Met Gly Val Asp
210                 215                 220

Gly Ile Arg Phe Asp Ala Val Lys His Met Pro Phe Gly Trp Gln Lys
225                 230                 235                 240

Ser Phe Val Ser Ser Ile Tyr Gly Gly Asp His Pro Val Phe Thr Phe
            245                 250                 255

Gly Glu Trp Tyr Leu Gly Ala Asp Gln Thr Asp Gly Asp Asn Ile Lys
            260                 265                 270

Phe Ala Asn Glu Ser Gly Met Asn Leu Leu Asp Phe Glu Tyr Ala Gln
            275                 280                 285

Glu Val Arg Glu Val Phe Arg Asp Lys Thr Glu Thr Met Lys Asp Leu
290                 295                 300

Tyr Glu Val Leu Ala Ser Thr Glu Ser Gln Tyr Asp Tyr Ile Asn Asn
305                 310                 315                 320

Met Val Thr Phe Ile Asp Asn His Asp Met Asp Arg Phe Gln Val Ala
            325                 330                 335

Gly Ser Gly Thr Arg Ala Thr Glu Gln Ala Leu Ala Leu Thr Leu Thr
            340                 345                 350

Ser Arg Gly Val Pro Ala Ile Tyr Tyr Gly Thr Glu Gln Tyr Met Thr
            355                 360                 365

Gly Asp Gly Asp Pro Asn Asn Arg Ala Met Met Thr Ser Phe Asn Thr
370                 375                 380

Gly Thr Thr Ala Tyr Lys Val Ile Gln Ala Leu Ala Pro Leu Arg Lys
385                 390                 395                 400

Ser Asn Pro Ala Ile Ala Tyr Gly Thr Thr Thr Glu Arg Trp Val Asn
            405                 410                 415

Asn Asp Val Leu Ile Ile Glu Arg Lys Phe Gly Ser Ser Ala Ala Leu
            420                 425                 430

Val Ala Ile Asn Arg Asn Ser Ser Ala Ala Tyr Pro Ile Ser Gly Leu
            435                 440                 445

Leu Ser Ser Leu Pro Ala Gly Thr Tyr Ser Asp Val Leu Asn Gly Leu
450                 455                 460

Leu Asn Gly Asn Ser Ile Thr Val Gly Ser Gly Ala Val Thr Asn
465                 470                 475                 480

Phe Thr Leu Ala Ala Gly Gly Thr Ala Val Trp Gln Tyr Thr Ala Pro
            485                 490                 495

Glu Thr Ser Pro Ala Ile Gly Asn Val Gly Pro Thr Met Gly Gln Pro

```
                    500                 505                 510
Gly Asn Ile Val Thr Ile Asp Gly Arg Gly Phe Gly Thr Ala Gly
            515                 520                 525

Thr Val Tyr Phe Gly Thr Thr Ala Val Thr Gly Ser Gly Ile Val Ser
530                     535                 540

Trp Glu Asp Thr Gln Ile Lys Ala Val Ile Pro Lys Val Ala Ala Gly
545                     550                 555                 560

Lys Thr Gly Val Ser Val Lys Thr Ser Ser Gly Thr Ala Ser Asn Thr
                565                 570                 575

Phe Lys Ser Phe Asn Val Leu Thr Gly Asp Gln Val Thr Val Arg Phe
                580                 585                 590

Leu Val Asn Gln Ala Asn Thr Asn Tyr Gly Thr Asn Val Tyr Leu Val
                595                 600                 605

Gly Asn Ala Ala Glu Leu Gly Ser Trp Asp Pro Asn Lys Ala Ile Gly
            610                 615                 620

Pro Met Tyr Asn Gln Val Ile Ala Lys Tyr Pro Ser Trp Tyr Tyr Asp
625                     630                 635                 640

Val Ser Val Pro Ala Gly Thr Lys Leu Asp Phe Lys Phe Ile Lys Lys
                    645                 650                 655

Gly Gly Gly Thr Val Thr Trp Glu Gly Gly Asn His Thr Tyr Thr
                660                 665                 670

Thr Pro Ala Ser Gly Val Gly Thr Val Thr Val Asp Trp Gln Asn
            675                 680                 685

<210> SEQ ID NO 76
<211> LENGTH: 675
<212> TYPE: PRT
<213> ORGANISM: Bacillus ohbensis

<400> SEQUENCE: 76

Asp Val Thr Asn Lys Val Asn Tyr Thr Arg Asp Val Ile Tyr Gln Ile
1               5                   10                  15

Val Thr Asp Arg Phe Ser Asp Gly Asp Pro Ser Asn Asn Pro Thr Gly
            20                  25                  30

Ala Ile Tyr Ser Gln Asp Cys Ser Asp Leu His Lys Tyr Cys Gly Gly
        35                  40                  45

Asp Trp Gln Gly Ile Ile Asp Lys Ile Asn Asp Gly Tyr Leu Thr Asp
    50                  55                  60

Leu Gly Ile Thr Ala Ile Trp Ile Ser Gln Pro Val Glu Asn Val Tyr
65                  70                  75                  80

Ala Leu His Pro Ser Gly Tyr Thr Ser Tyr His Gly Tyr Trp Ala Arg
                85                  90                  95

Asp Tyr Lys Arg Thr Asn Pro Phe Tyr Gly Asp Phe Ser Asp Phe Asp
            100                 105                 110

Arg Leu Met Asp Thr Ala His Ser Asn Gly Ile Lys Val Ile Met Asp
        115                 120                 125

Phe Thr Pro Asn His Ser Ser Pro Ala Leu Glu Thr Asp Pro Ser Tyr
    130                 135                 140

Ala Glu Asn Gly Ala Val Tyr Asn Asp Gly Val Leu Ile Gly Asn Tyr
145                 150                 155                 160

Ser Asn Asp Pro Asn Asn Leu Phe His His Asn Gly Gly Thr Asp Phe
                165                 170                 175

Ser Ser Tyr Glu Asp Ser Ile Tyr Arg Asn Leu Tyr Asp Leu Ala Asp
            180                 185                 190

Tyr Asp Leu Asn Asn Thr Val Met Asp Gln Tyr Leu Lys Glu Ser Ile
```

-continued

```
                195                 200                 205
Lys Leu Trp Leu Asp Lys Gly Ile Asp Gly Ile Arg Val Asp Ala Val
    210                 215                 220
Lys His Met Ser Glu Gly Trp Gln Thr Ser Leu Met Ser Asp Ile Tyr
225                 230                 235                 240
Ala His Glu Pro Val Phe Thr Phe Gly Glu Trp Phe Leu Gly Ser Gly
                245                 250                 255
Glu Val Asp Pro Gln Asn His His Phe Ala Asn Glu Ser Gly Met Ser
                260                 265                 270
Leu Leu Asp Phe Gln Phe Gly Gln Thr Ile Arg Asp Val Leu Met Asp
            275                 280                 285
Gly Ser Ser Asn Trp Tyr Asp Phe Asn Glu Met Ile Ala Ser Thr Glu
290                 295                 300
Glu Asp Tyr Asp Glu Val Ile Asp Gln Val Thr Phe Ile Asp Asn His
305                 310                 315                 320
Asp Met Ser Arg Phe Ser Phe Glu Gln Ser Ser Asn Arg His Thr Asp
                325                 330                 335
Ile Ala Leu Ala Val Leu Leu Thr Ser Arg Gly Val Pro Thr Ile Tyr
            340                 345                 350
Tyr Gly Thr Glu Gln Tyr Leu Thr Gly Gly Asn Asp Pro Glu Asn Arg
        355                 360                 365
Lys Pro Met Ser Asp Phe Asp Arg Thr Thr Asn Ser Tyr Gln Ile Ile
370                 375                 380
Ser Thr Leu Ala Ser Leu Arg Gln Asn Asn Pro Ala Leu Gly Tyr Gly
385                 390                 395                 400
Asn Thr Ser Glu Arg Trp Ile Asn Ser Asp Val Tyr Ile Tyr Glu Arg
                405                 410                 415
Ser Phe Gly Asp Ser Val Val Leu Thr Ala Val Asn Ser Gly Asp Thr
            420                 425                 430
Ser Tyr Thr Ile Asn Asn Leu Asn Thr Ser Leu Pro Gln Gly Gln Tyr
        435                 440                 445
Thr Asp Glu Leu Gln Gln Leu Leu Asp Gly Asn Glu Ile Thr Val Asn
    450                 455                 460
Ser Asn Gly Ala Val Asp Ser Phe Gln Leu Ser Ala Asn Gly Val Ser
465                 470                 475                 480
Val Trp Gln Ile Thr Glu Glu His Ala Ser Pro Leu Ile Gly His Val
                485                 490                 495
Gly Pro Met Met Gly Lys His Gly Asn Thr Val Thr Ile Thr Gly Glu
            500                 505                 510
Gly Phe Gly Asp Asn Glu Gly Ser Val Leu Phe Asp Ser Asp Phe Ser
        515                 520                 525
Asp Val Leu Ser Trp Ser Asp Thr Lys Ile Glu Val Ser Val Pro Asp
    530                 535                 540
Val Thr Ala Gly His Tyr Asp Ile Ser Val Val Asn Ala Gly Asp Ser
545                 550                 555                 560
Gln Ser Pro Thr Tyr Asp Lys Phe Glu Val Leu Thr Gly Asp Gln Val
                565                 570                 575
Ser Ile Arg Phe Ala Val Asn Asn Ala Thr Thr Ser Leu Gly Thr Asn
            580                 585                 590
Leu Tyr Met Val Gly Asn Val Asn Glu Leu Gly Asn Trp Asp Pro Asp
        595                 600                 605
Gln Ala Ile Gly Pro Met Phe Asn Gln Val Met Tyr Gln Tyr Pro Thr
    610                 615                 620
```

-continued

```
Trp Tyr Tyr Asp Ile Ser Val Pro Ala Glu Glu Asn Leu Glu Tyr Lys
625                 630                 635                 640

Phe Ile Lys Lys Asp Ser Ser Gly Asn Val Val Trp Glu Ser Gly Asn
                645                 650                 655

Asn His Thr Tyr Thr Thr Pro Ala Thr Gly Thr Asp Thr Val Leu Val
                660                 665                 670

Asp Trp Gln
        675

<210> SEQ ID NO 77
<211> LENGTH: 680
<212> TYPE: PRT
<213> ORGANISM: Bacillus stearothermophilus

<400> SEQUENCE: 77

Ala Gly Asn Leu Asn Lys Val Asn Phe Thr Ser Asp Val Val Tyr Gln
1               5                   10                  15

Ile Val Val Asp Arg Phe Val Asp Gly Asn Thr Ser Asn Asn Pro Ser
                20                  25                  30

Gly Ala Leu Phe Ser Ser Gly Cys Thr Asn Leu Arg Lys Tyr Cys Gly
            35                  40                  45

Gly Asp Trp Gln Gly Ile Ile Asn Lys Ile Asn Asp Gly Tyr Leu Thr
50                  55                  60

Asp Met Gly Val Thr Ala Ile Trp Ile Ser Gln Pro Val Glu Asn Val
65                  70                  75                  80

Phe Ser Val Met Asn Asp Ala Ser Gly Ser Ala Ser Tyr His Gly Tyr
                85                  90                  95

Trp Ala Arg Asp Phe Lys Lys Pro Asn Pro Phe Phe Gly Thr Leu Ser
            100                 105                 110

Asp Phe Gln Arg Leu Val Asp Ala Ala His Ala Lys Gly Ile Lys Val
        115                 120                 125

Ile Ile Asp Phe Ala Pro Asn His Thr Ser Pro Ala Ser Glu Thr Asn
130                 135                 140

Pro Ser Tyr Met Glu Asn Gly Arg Leu Tyr Asp Asn Gly Thr Leu Leu
145                 150                 155                 160

Gly Gly Tyr Thr Asn Asp Ala Asn Met Tyr Phe His His Asn Gly Gly
                165                 170                 175

Thr Thr Phe Ser Ser Leu Glu Asp Gly Ile Tyr Arg Asn Leu Phe Asp
            180                 185                 190

Leu Ala Asp Leu Asn His Gln Asn Pro Val Ile Asp Arg Tyr Leu Lys
        195                 200                 205

Asp Ala Val Lys Met Trp Ile Asp Met Gly Ile Asp Gly Ile Arg Met
210                 215                 220

Asp Ala Val Lys His Met Pro Phe Gly Trp Gln Lys Ser Leu Met Asp
225                 230                 235                 240

Glu Ile Asp Asn Tyr Arg Pro Val Phe Thr Phe Gly Glu Trp Phe Leu
                245                 250                 255

Ser Glu Asn Glu Val Asp Ala Asn Asn His Tyr Phe Ala Asn Glu Ser
            260                 265                 270

Gly Met Ser Leu Leu Asp Phe Arg Phe Gly Gln Lys Leu Arg Gln Val
        275                 280                 285

Leu Arg Asn Asn Ser Asp Asn Trp Tyr Gly Phe Asn Gln Met Ile Gln
290                 295                 300

Asp Thr Ala Ser Ala Tyr Asp Glu Val Leu Asp Gln Val Thr Phe Ile
305                 310                 315                 320
```

```
Asp Asn His Asp Met Asp Arg Phe Met Ile Asp Gly Gly Asp Pro Arg
            325                 330                 335

Lys Val Asp Met Ala Leu Ala Val Leu Leu Thr Ser Arg Gly Val Pro
            340                 345                 350

Asn Ile Tyr Tyr Gly Thr Glu Gln Tyr Met Thr Gly Asn Gly Asp Pro
            355                 360                 365

Asn Asn Arg Lys Met Met Ser Ser Phe Asn Lys Asn Thr Arg Ala Tyr
            370                 375                 380

Gln Val Ile Gln Lys Leu Ser Ser Leu Arg Arg Asn Asn Pro Ala Leu
385                 390                 395                 400

Ala Tyr Gly Asp Thr Glu Gln Arg Trp Ile Asn Gly Asp Val Tyr Val
                405                 410                 415

Tyr Glu Arg Gln Phe Gly Lys Asp Val Val Leu Val Ala Val Asn Arg
                420                 425                 430

Ser Ser Ser Ser Asn Tyr Ser Ile Thr Gly Leu Phe Thr Ala Leu Pro
                435                 440                 445

Ala Gly Thr Tyr Thr Asp Gln Leu Gly Gly Leu Leu Asp Gly Asn Thr
                450                 455                 460

Ile Gln Val Gly Ser Asn Gly Ser Val Asn Ala Phe Asp Leu Gly Pro
465                 470                 475                 480

Gly Glu Val Gly Val Trp Ala Tyr Ser Ala Thr Glu Ser Thr Pro Ile
                485                 490                 495

Ile Gly His Val Gly Pro Met Met Gly Gln Val Gly His Gln Val Thr
                500                 505                 510

Ile Asp Gly Glu Gly Phe Gly Thr Asn Thr Gly Thr Val Lys Phe Gly
                515                 520                 525

Thr Thr Ala Ala Asn Val Val Ser Trp Ser Asn Gln Ile Val Val
                530                 535                 540

Ala Val Pro Asn Val Ser Pro Gly Lys Tyr Asn Ile Thr Val Gln Ser
545                 550                 555                 560

Ser Ser Gly Gln Thr Ser Ala Ala Tyr Asp Asn Phe Glu Val Leu Thr
                565                 570                 575

Asn Asp Gln Val Ser Val Arg Phe Val Val Asn Asn Ala Thr Thr Asn
                580                 585                 590

Leu Gly Gln Asn Ile Tyr Ile Val Gly Asn Val Tyr Glu Leu Gly Asn
                595                 600                 605

Trp Asp Thr Ser Lys Ala Ile Gly Pro Met Phe Asn Gln Val Val Tyr
                610                 615                 620

Ser Tyr Pro Thr Trp Tyr Ile Asp Val Ser Val Pro Glu Gly Lys Thr
625                 630                 635                 640

Ile Glu Phe Lys Phe Ile Lys Lys Asp Ser Gln Gly Asn Val Thr Trp
                645                 650                 655

Glu Ser Gly Ser Asn His Val Tyr Thr Thr Pro Thr Asn Thr Thr Gly
                660                 665                 670

Lys Ile Ile Val Asp Trp Gln Asn
                675                 680

<210> SEQ ID NO 78
<211> LENGTH: 624
<212> TYPE: PRT
<213> ORGANISM: Klebsiella pneumoniae

<400> SEQUENCE: 78

Glu Pro Glu Glu Thr Tyr Leu Asp Phe Arg Lys Glu Thr Ile Tyr Phe
1               5                   10                  15
```

-continued

```
Leu Phe Leu Asp Arg Phe Ser Asp Gly Asp Pro Ser Asn Asn Ala Gly
            20                  25                  30

Phe Asn Ser Ala Thr Tyr Asp Pro Asn Asn Leu Lys Lys Tyr Thr Gly
            35                  40                  45

Gly Asp Leu Arg Gly Leu Ile Asn Lys Leu Pro Tyr Leu Lys Ser Leu
 50                  55                  60

Gly Val Thr Ser Ile Trp Ile Thr Pro Pro Ile Asp Asn Val Asn Asn
 65                  70                  75                  80

Thr Asp Ala Ala Gly Asn Thr Gly Tyr His Gly Tyr Trp Gly Arg Asp
                85                  90                  95

Tyr Phe Arg Ile Asp Glu His Phe Gly Asn Leu Asp Asp Phe Lys Glu
                100                 105                 110

Leu Thr Ser Leu Met His Ser Pro Asp Tyr Asn Met Lys Leu Val Leu
                115                 120                 125

Asp Tyr Ala Pro Asn His Ser Asn Ala Asn Asp Glu Asn Glu Phe Gly
130                 135                 140

Ala Leu Tyr Arg Asp Gly Val Phe Ile Thr Asp Tyr Pro Thr Asn Val
145                 150                 155                 160

Ala Ala Asn Thr Gly Trp Tyr His His Asn Gly Val Thr Asn Trp
                165                 170                 175

Asn Asp Phe Phe Gln Val Lys Asn His Asn Leu Phe Asn Leu Ser Asp
                180                 185                 190

Leu Asn Gln Ser Asn Thr Asp Val Tyr Gln Tyr Leu Leu Asp Gly Ser
                195                 200                 205

Lys Phe Trp Ile Asp Ala Gly Val Asp Ala Ile Arg Ile Asp Ala Ile
                210                 215                 220

Lys His Met Asp Lys Ser Phe Ile Gln Lys Trp Thr Ser Asp Ile Tyr
225                 230                 235                 240

Asp Tyr Ser Lys Ser Ile Gly Arg Glu Gly Phe Phe Phe Gly Glu
                245                 250                 255

Trp Phe Gly Ala Ser Ala Asn Thr Thr Thr Gly Val Asp Gly Asn Ala
                260                 265                 270

Ile Asp Tyr Ala Asn Thr Ser Gly Ser Ala Leu Leu Asp Phe Gly Phe
                275                 280                 285

Arg Asp Thr Leu Glu Arg Val Leu Val Gly Arg Ser Gly Asn Thr Met
290                 295                 300

Lys Thr Leu Asn Ser Tyr Leu Ile Lys Arg Gln Thr Val Phe Thr Ser
305                 310                 315                 320

Asp Asp Trp Gln Val Val Phe Met Asp Asn His Asp Met Ala Arg Ile
                325                 330                 335

Gly Thr Ala Leu Arg Ser Asn Ala Thr Thr Phe Gly Pro Gly Asn Asn
                340                 345                 350

Glu Thr Gly Gly Ser Gln Ser Glu Ala Phe Ala Gln Lys Arg Ile Asp
                355                 360                 365

Leu Gly Leu Val Ala Thr Met Thr Val Arg Gly Ile Pro Ala Ile Tyr
                370                 375                 380

Tyr Gly Thr Glu His Tyr Ala Ala Asn Phe Thr Ser Asn Ser Phe Gly
385                 390                 395                 400

Gln Val Gly Ser Asp Pro Tyr Asn Arg Glu Lys Met Pro Gly Phe Asp
                405                 410                 415

Thr Glu Ser Glu Ala Phe Ser Ile Ile Lys Thr Leu Gly Asp Leu Arg
                420                 425                 430

Lys Ser Ser Pro Ala Ile Gln Asn Gly Thr Tyr Thr Glu Leu Trp Val
                435                 440                 445
```

```
Asn Asp Asp Ile Leu Val Phe Glu Arg Arg Ser Gly Asn Asp Ile Val
    450                 455                 460

Ile Val Ala Leu Asn Arg Gly Glu Ala Asn Thr Ile Asn Val Lys Asn
465                 470                 475                 480

Ile Ala Val Pro Asn Gly Val Tyr Pro Ser Leu Ile Gly Asn Asn Ser
            485                 490                 495

Val Ser Val Ala Asn Lys Arg Thr Thr Leu Thr Leu Met Gln Asn Glu
            500                 505                 510

Ala Val Val Ile Arg Ser Gln Ser Asp Asp Ala Glu Asn Pro Thr Val
        515                 520                 525

Gln Ser Ile Asn Phe Thr Cys Asn Asn Gly Tyr Thr Ile Ser Gly Gln
    530                 535                 540

Ser Val Tyr Ile Ile Gly Asn Ile Pro Gln Leu Gly Gly Trp Asp Leu
545             550                 555                 560

Thr Lys Ala Val Lys Ile Ser Pro Thr Gln Tyr Pro Gln Trp Ser Ala
            565                 570                 575

Ser Leu Glu Leu Pro Ser Asp Leu Asn Val Glu Trp Lys Cys Val Lys
            580                 585                 590

Arg Asn Glu Thr Asn Pro Thr Ala Asn Val Glu Trp Gln Ser Gly Ala
        595                 600                 605

Asn Asn Gln Phe Asn Ser Asn Asp Thr Gln Thr Thr Asn Gly Ser Phe
610                 615                 620
```

CYCLOMALTODEXTRIN GLUCANOTRANSFERASE VARIANTS

CROSS-REFERENCE TO RELATED APPLICATIONS

This application is a continuation of application Ser. No. PCT/DK96/00179 filed Apr. 22, 1996 and claims priority under 35 U.S.C. 119 of Danish application Ser. Nos. 0477/95, 1173/95 and 1281/95 filed Apr. 21, 1995, Oct. 17, 1995 and Nov. 16, 1995, respectively, the contents of which are fully incorporated herein by reference.

TECHNICAL FIELD

The present invention relates to variants of cyclomaltodextrin glucanotransferase. More specifically the invention relates to a method of modifying the substrate binding and/or product selectivity of a precursor CGTase enzyme, and CGTase variants derived from a precursor CGTase enzyme by substitution, insertion and/or deletion of one or more amino acid residue(s), which amino acid residue(s) holds a position close to the substrate. Moreover, the invention relates to DNA constructs encoding the CGTase variants, expression vectors, host cells and methods of producing the CGTase variants of the invention.

BACKGROUND ART

Cyclomaltodextrin glucanotransferase (E.C. 2.4.1.19), also designated cyclodextrin glucanotransferase or cyclodextrin glycosyltransferase, in the following termed CGTase, catalyses the conversion of starch and similar substrates into cyclomaltodextrins via an intramolecular transglycosylation reaction, thereby forming cyclomaltodextrins, in the following termed cyclodextrins (or CD), of various sizes. Commercially most important are cyclodextrins of 6, 7 and 8 glucose units, which are termed α-, β- and γ-cyclodextrins, respectively. Commercially less important are cyclodextrins of 9, 10, and 11 glucose units, which are termed δ-, ε-, and ζ-cyclodextrins, respectively.

Cyclodextrins are thus cyclic glucose oligomers with a hydrophobic internal cavity. They are able to form inclusion complexes with many small hydrophobic molecules in aqueous solutions, resulting in changes in physical properties, e.g. increased solubility and stability and decreased chemical reactivity and volatility. Cyclodextrins find applications particularly in the food, cosmetic, chemical and pharmaceutical industries.

Most CGTases have both starch-degrading activity and transglycosylation activity. Although some CGTases produce mainly α-cyclodextrins and some CGTases produce mainly β-cyclodextrins, CGTases usually form a mixture of α-, β- and γ-cyclodextrins. Selective precipitation steps with organic solvents may be used for the isolation of separate α-, β- and γ-cyclodextrins. To avoid expensive and environmentally harmful procedures, the availability of CGTases capable of producing an increased ratio of one particular type of cyclodextrin is desirable.

CGTases from different bacterial sources, including CGTases obtained from Bacillus, Brevibacterium, Clostridium, Corynebacterium, Klebsiella, Micrococcus, Thermoanaerobacter and Thermoanaerobacterium have been described in the literature.

Thus Kimura et al. [Kimura K, Kataoka S, Ishii Y, Takano T and Yamane K; *J. Bacteriol.* 1987 169 4399–4402] describe a Bacillus sp. 1011 CGTase, Kaneko et al. [Kaneko T, Hamamoto T and Horikoshi K; *J. Gen. Microbiol.* 1988 134 97–105] describe a Bacillus sp. Strain 38-2 CGTase, Kaneko et al. [Kaneko T, Song K B, Hamamoto T, Kudo T and Horikoshi K; *J. Gen. Microbiol.* 1989 135 3447–3457] describe a Bacillus sp. Strain 17-1 CGTase, Itkor et al. [Itkor P, Tsukagoshi N and Udaka S; *Biochem. Biophys. Res. Commun.* 1990 166 630–636] describe a Bacillus sp. B1018 CGTase, Schmid et al. [Schmid G, Englbrecht A, Schmid D; Proceedings of the Fourth International Symposium on Cyclodextrins (Huber O, Szejtli J, Eds.), 1988 71–76] describe a Bacillus sp. 1-1 CGTase, Kitamoto et al. [Kitamoto N, Kimura T, Kito Y, Ohmiya K; *J. Ferment. Bioeng.* 1992 74 345–351] describe a Bacillus sp. KC201 CGTase, Sakai et al. [Sakai S, Kubota M, Nakada T, Torigoe K, Ando O and Sugimoto T; *J. Jpn. Soc. Starch. Sci.* 1987 34 140–147] describe a *Bacillus stearothermophilis* CGTase and a *Bacillus macerans* CGTase, Takano et al. [Takano T, Fukuda M, Monma M, Kobayashi S, Kainuma K and Yamane K; *J. Bacteriol.* 1986 166 (3) 1118–1122] describe a *Bacillus macerans* CGTase, Sin et al. [Sin K A, Nakamura A, Kobayashi K, Masaki H and Uozumi T; *Appl. Microbiol. Biotechnol.* 1991 35 600–605] describe a *Bacillus ohbensis* CGTase, Nitschke et al. [Nitschke L, Heeger K, Bender H and Schultz G; *Appl. Microbiol. Biotechnol.* 1990 33 542–546] describe a *Bacillus circulans* CGTase, Hill et al. [Hill D E, Aldape R and Rozzell J D; *Nucleic Acids Res.* 1990 18 199] describe a *Bacillus licheniformis* CGTase, Tomita et al. [Tomita K, Kaneda M, Kawamura K and Nakanishi K; *J. Ferm. Bioeng.* 1993 75 (2) 89–92] describe a *Bacillus autolyticus* CGTase, Jamuna et al. [Jamuna R, Saswathi N, Sheela R and Ramakrishna S V; *Appl. Biochem. Biotechnol.* 1993 43 163–176] describe a *Bacillus cereus* CGTase, Akimaru et al. [Akimaru K, Yagi T and Yamamoto S; *J. Ferm. Bioeng.* 1991 71 (5) 322–328] describe a *Bacillus coagulans* CGTase, Schmid G [Schmid G; *New Trends in Cyclodextrins and Derivatives* (Duchene D, Ed.), Editions de Sante, Paris, 1991, 25–54] describes a *Bacillus firmus* CGTase, Abelian et al. [Abelian V A, Adamian M O, Abelian L A A, Balayan A M and Afrikian E K; *Biochememistry (Moscow)* 1995 60 (6) 665–669] describe a *Bacillus halophilus* CGTase, and Kato et al. [Kato T and Horikoshi K; *J. Jpn. Soc. Starch Sci.* 1986 33 (2) 137–143] describe a *Bacillus subtilis* CGTase.

EP 614971 describes a Brevibacterium CGTase, Haeckel & Bahl [Haeckel K, Bahl H; *FEMS Microbiol. Lett.* 1989 60 333–338] describe *Clostridium thermosulfurogenes* CGTase, Podkovyrov & Zeikus [Podkovyrov S M, Zeikus J G; *J. Bacteriol.* 1992 174 5400–5405] describe a *Clostridium thermohydrosulfricum* CGTase, JP 7000183 describes a Corynebacterium CGTase, Binder et al. [Binder F, Huber O and Böck A; *Gene* 1986 47 269–277] describe a *Klebsiella pneumoniae* CGTase, U.S. Pat. No. 4,317,881 describes a Micrococcus CGTase, and Wind et al. [Wind R D, Liebl W, Buitelaar R M, Penninga D, Spreinat A, Dijkhuizen L, Bahl H; *Appl. Environ. Microbiol.* 1995 61 (4) 1257–1265] describe *Thermoanaerobacterium thermosulfurigenes* CGTase.

A CGTase produced by Thermoanaerobacter sp. has been reported by Norman & Jorgensen [Norman B E, Jorgensen S T; *Denpun Kagaku* 1992 39 99–106, and WO 89/03421], however, its amino acid sequence has never been disclosed. Here we report the nucleotide sequence encoding the Thermoanaerobacter sp. CGTase (presented as SEQ ID:NO 1), as well as its amino acid sequence (presented as SEQ ID:NO 2).

Also, CGTases from thermophilic Actinomycetes have been reported [Abelian V A, Afyan K B, Avakian Z G, Melkumyan A G and Afrikian E G; *Biochemistry (Moscow)* 1995 60 (10) 1223–1229].

Recently protein engineering has been employed in order to modify certain CGTases to selectively produce more or less of a specific cyclodextrin.

The Structure of CGTases

CGTases are functionally related to α-amylases. CGTases and α-amylases both degrade starch by hydrolysis of the α-(1,4)-glycosidic bonds, but produce virtually exclusively cyclic and linear products, respectively.

Members of the CGTase family possess a high overall amino acid sequence identity, more than 60%. CGTases and α-amylases share about 30% amino acid sequence identity. However, the active site clefts of CGTases and α-amylases, located between the A and B domain (Asp229, Glu257 and Asp328), are rather similar.

Recently, the tertiary structures of CGTases were determined. Thus, Hofman et al. [Hofman B E, Bender H, Schultz G E; *J. Mol. Biol.* 1989 209 793–800] and Klein & Schulz [Klein C, Schulz G E; *J. Mol. Biol.* 1991 217 737–750] report the tertiary structure of a CGTase derived from *Bacillus circulans* Strain 8, Kubota et al. [Kubota M, Matsuura Y, Sakai S and Katsube Y; *Denpun Kagaku* 1991 38 141–146] report the tertiary structure of a CGTase derived from *Bacillus stearothermophilus* TC-91, Lawson et al. [Lawson C L, van Monifort R, Strokopytov B, Rozeboom H J, Kalk K H, de Vries G E, Penninga D, Dijkhuizen L, and Dijkstra B W; *J. Mol. Biol.* 1994 236 590–600] report the tertiary structure of a CGTase derived from *Bacillus circulans* Strain 251, Strokopytov et al. [Strokopytov B, Penninga D, Rozeboom H J, Kalk K H, Dijkhuizen L and Dijkstra B W; *Biochemistry* 1995 34 2234–2240] report the tertiary structure of a CGTase derived from *Bacillus circulans* Strain 251, which CGTase has been complexed with acarbose, an effective CGTase inhibitor, and Knegtel et al. [Knegtel R M A, Wind R D, Rozeboom H J, Kalk K H, Buitelaar R M, Dijkhuizen L and Dijkstra B W; *J. Mol. Biol.* 1996 256 611–622] report the tertiary structure of a CGTase derived from *Thermoanaerobacterium thermosulfurigenes*.

These and other studies reveal that *Bacillus circulans* CGTases are composed of five domains. The three-dimensional structures also reveal that the N-terminal domains of CGTases have structural similarities to those of α-amylases, whereas the C-terminal domains were found to be unique to CGTases.

The catalytic site of CGTases is located in the A domain, and has three catalytic residues (in *Bacillus circulans* strain 251 these are Asp229, Glu257 and Asp328, respectively, cf. Strokopytov et al. 1995, op cit.). A central amino acid residue is located in the B domain, around which residue the cyclodextrins are formed, i.e. the cyclization axis. Substitution of this central residue, e.g. tyrosine at residue 188 in *Bacillus ohbensis* (corresponding to position 195, CGTase numbering) in order to increase the relative production of γ-cyclodextrin to β-cyclodextrin has been the object of the study described by Sin et al. [Sin K, Nakamura A, Masaki H, Matsuura Y and Uozumi T; *Journal of Biotechnology* 1994 32 283–288] and JP-A-5219948.

Nakamura et al. [Nakamura A, Haga K and Yamane K; *Biochemistry* 1994 33 9929–9936] describe the effects on substrate binding and cyclization characteristics by replacements carried out at four residues in the active center of a *Bacillus* sp. Strain 1011 CGTase. In these CGTase variants, a phenylalanine at position 183 has been replaced by leucine, a tyrosine at position 195 has been replaced by alanine, phenylalanine, leucine, threonine, valine, and tryptophan, respectively, a phenylalanine at position 259 has been replaced by leucine, and a phenylalanine at position 283 has been replaced by leucine.

Penninga et al. [Penninga D, Strokopytov B, Rozeboom H J, Lawson C L, Dijkstra B W, Bergsma J and Dijkhuizen L; *Biochemistry* 1995 34 3368–3376] describe the effect on activity and product selectivity of site-directed mutations in tyrosine at position 195 of a *Bacillus circulans* Strain 251 CGTase. In this publication four CGTase variants have been produced, in which variants the tyrosine at position 195 have been replaced by phenylalanine, tryptophan, leucine and glycine, respectively.

Fujiware et al. [Fujiwara S, Kakihara H, Sakaguchi K and Imanaka T; *J. Bacteriol.* 1992 174 (22) 7478–7481] describe CGTase variants derived from *Bacillus stearothermophilus*, in which a tyrosine residue at position 191 (corresponding to position 195 CGTase numbering) has been replaced by phenylalanine, a tryptophan residue at position 254 (corresponding to position 258, CGTase numbering) has been replaced by valine, a phenylalanine at position 255 (corresponding to position 259, CGTase numbering) has been replaced by phenylalanine and isoleucine, respectively, a threonine residue at position 591 (corresponding to position 598, CGTase numbering) has been replaced by phenylalanine, and a tryptophan residue at position 629 (corresponding to position 636, CGTase numbering) has been replaced by phenylalanine.

JP-A-7023781 describes CGTase variants derived from *Bacillus* sp. 1011, in which a tyrosine residue at position 195 has been replaced by leucine, valine, phenylalanine and isoleucine, respectively.

JP-A-5244945 describes CGTase variants derived from *Bacillus stearothermophilus* TC-91, in which tyrosine residues at positions 222 and 286 (corresponding to positions 195 and 259, CGTase numbering) have been replaced by phenylalanine in order to increase the relative production of α-cyclodextrin to β-cyclodextrin.

JP-A-5041985 describes CGTase variants derived from *Bacillus* sp. #1011, in which histidine at residue 140 in region A, histidine at residue 233 in region B, and histidine at residue 327 in region C, respectively, have been replaced by arginine and asparagine residues, respectively.

EP 630,967 describes CGTase variants in which a tyrosine residue at position 211 of a *Bacillus* sp. 290-3 CGTase (corresponding to position 195, CGTase numbering), at position 217 of a *Bacillus* sp. 1-1 CGTase (corresponding to position 195, CGTase numbering), and at position 229 of a *Bacillus circulans* CGTase (corresponding to position 195, CGTase numbering), have been substituted for tryptophan and serine.

Up to now, all efforts in making CGTase variants have lead to substitutions in the region around the active site, in particular at the central cyclization residue, corresponding to position 195, CGTase numbering. Only few CGTase variants holding substitutions at more distant regions have been suggested, and the manufacture of these variants have not been based on any particular concept.

SUMMARY OF THE INVENTION

It is an object of the present invention to provide novel variants of CGTases, which variants, when compared to the precursor enzyme, show increased product selectivity and/or reduced product inhibition.

Accordingly, in its first aspect, the invention provides a method of modifying the substrate binding and/or product selectivity of a precursor CGTase enzyme, which method comprises substitution, insertion and/or deletion of one or more amino acid residue(s) of the precursor enzyme, which amino acid residue(s) holds a position close to the substrate.

In another aspect, the invention provides a CGTase variant derived from a precursor CGTase enzyme by substitution, insertion and/or deletion of one or more amino acid residue(s), which amino acid residue(s) holds a position close to the substrate.

In a third aspect, the invention provides a DNA construct encoding a CGTase variant of the invention.

In a fourth aspect, the invention provides a recombinant expression vector comprising the DNA construct of the invention.

In a fifth aspect, the invention provides a host cell comprising the DNA construct of the invention, or the recombinant expression vector of the invention.

In a sixth aspect, the invention provides a method of producing a CGTase variant of the invention, which method comprises culturing the host cell of the invention under conditions permitting the production of the CGTase variant, and recovering the enzyme from the culture.

In further aspects, the invention provides CGTase variants for use in processes for the manufacture of cyclodextrins, in processes for the manufacture of linear oligosaccharides, and in processes for in situ generation of cyclodextrins.

Amino Acids

In the context of this invention the following symbols and abbreviations for amino acids and amino acid residues are used:

| | | | | |
|---|---|---|---|---|
| A | = | Ala | = | Alanine |
| C | = | Cys | = | Cysteine |
| D | = | Asp | = | Aspartic acid |
| E | = | Glu | = | Glutamic acid |
| F | = | Phe | = | Phenylalanine |
| G | = | Gly | = | Glycine |
| H | = | His | = | Histidine |
| I | = | Ile | = | Isoleucine |
| K | = | Lys | = | Lysine |
| L | = | Leu | = | Leucine |
| M | = | Met | = | Methionine |
| N | = | Asn | = | Asparagine |
| P | = | Pro | = | Proline |
| Q | = | Gln | = | Glutamine |
| R | = | Arg | = | Arginine |
| S | = | Ser | = | Serine |
| T | = | Thr | = | Threonine |
| V | = | Val | = | Valine |
| W | = | Trp | = | Tryptophan |
| Y | = | Tyr | = | Tyrosine |
| B | = | Asx | = | Asp or Asn |
| Z | = | Glx | = | Glu or Gln |
| X | = | Xaa | = | Any amino acid |
| * | = | Deletion or absent amino acid | | |

CGTase Variants

A CGTase variant of this invention is a CGTase variant or mutated CGTase, having an amino acid sequence not found in nature.

A CGTase variant or mutated CGTase of this invention is a functional derivative of a precursor CGTase enzyme (i.e. the native, parental, or wild-type enzyme), and may be obtained by alteration of a DNA nucleotide sequence of a precursor gene or its derivatives, encoding the precursor enzyme. The CGTase variant or mutated CGTase may be expressed and produced when the DNA nucleotide sequence encoding the CGTase variant is inserted into a suitable vector in a suitable host organism. The host organism is not necessarily identical to the organism from which the precursor gene originated.

In the literature, enzyme variants have also been referred to as mutants or muteins.

CGTase Numbering

In the context of this invention a specific numbering of amino acid residue positions in CGTase enzymes is employed. By alignment of the amino acid sequences of various known CGTases it is possible to unambiguously allot a CGTase amino acid position number to any amino acid residue position in any CGTase enzyme, which amino acid sequence is known.

Using the numbering system originating from the amino acid sequence of the CGTase obtained from *Bacillus circulans* Strain 251, which sequence is shown in Table 1 (a), aligned with the amino acid sequence of a number of other known CGTases, it is possible to indicate the position of an amino acid residue in a CGTase enzyme unambiguously.

In describing the various CGTase variants produced or contemplated according to the invention, the following nomenclatures are adapted for ease of reference:

[Original amino acid; Position; Substituted amino acid]

Accordingly, the substitution of serine with alanine in position 145 is designated as S145A.

Amino acid residues which represent insertions in relation to the amino acid sequence of the CGTase from *Bacillus circulans* Strain 251, are numbered by the addition of letters in alphabetical order to the preceding CGTase number, such as e.g. position 91aF for the "insert" Phe between Thr at position 91 and Gly at position 92 of the amino acid sequence of the CGTase from Thermoanaerobacter sp. ATCC 53627, cf. Table 1 (j).

Deletion of a proline at position 149 is indicated as P149*, and an insertion between position 147 and 148 where no amino acid residue is present, is indicated as *147aD for insertion of an aspartic acid in position 147a.

Multiple mutations are separated by slash marks ("/"), e.g. S145A/D147L, representing mutations in positions 145 and 147 substituting serine with alanine and aspartic acid with leucine, respectively.

If a substitution is made by mutation in e.g. a CGTase derived from a strain of *Bacillus circulans*, the product is designated e.g. "*B. circulans*/S145A".

All positions referred to in this application by CGTase numbering refer to the CGTase numbers described above.

TABLE 1

Amino Acid Sequence Alignment, CGTase Numbering and Domains of Selected CGTases of Different Bacterial Origin
a *Bacillus circulans* 251 (SEQ ID NO: 70); b Bacillus sp. 1-1 (SEQ ID NO: 71); c Bacillus sp. 38-2 (SEQ ID NO: 72); d Bacillus sp. 1011 (SEQ ID NO: 73); e *Bacillus licheniformis* (SEQ ID NO: 74); f *Bacillus macerans* (SEQ ID NO: 75); g *Bacillus ohbensis* (SEQ ID NO: 76); h *Bacillus stearothermophilus* (SEQ ID NO: 77); i *Klebsiella pneumoniae* (SEQ ID NO: 78); j Thermoanaerobacter ATCC 53627 (SEQ ID NO: 2).

| No | a | b | c | d | e | f | g | h | i | j | Domain |
|---|---|---|---|---|---|---|---|---|---|---|---|
| 1 | A | E | A | A | D | S | D | A | E | A | A |
| 2 | P | A | P | P | A | P | * | G | P | P | A |
| 3 | D | D | D | D | D | D | * | N | B | D | A |
| 4 | T | * | T | T | T | T | * | * | E | T | A |
| 5 | S | * | S | S | * | S | * | * | T | S | A |
| 6 | V | V | V | V | V | V | V | * | Y | V | A |
| 7 | S | T | S | S | T | D | T | L | * | S | A |
| 8 | N | N | N | N | N | N | N | N | * | N | A |
| 9 | K | K | K | K | K | K | K | K | * | V | A |
| 10 | Q | V | Q | Q | Q | V | V | V | L | V | A |
| 11 | N | N | N | N | N | N | N | N | D | N | A |
| 12 | F | Y | F | F | F | F | Y | F | F | Y | A |
| 13 | S | S | S | S | S | S | T | T | R | S | A |
| 14 | T | D | T | T | T | T | R | S | K | T | A |
| 14a | * | K | * | * | * | * | R | * | K | * | A |
| 15 | D | D | D | D | D | D | D | D | E | D | A |
| 16 | V | V | V | V | V | V | V | V | T | V | A |
| 17 | I | I | I | I | I | I | I | V | I | I | A |
| 18 | Y | Y | Y | Y | Y | Y | Y | Y | Y | Y | A |
| 19 | Q | Q | Q | Q | Q | Q | Q | Q | F | Q | A |

TABLE 1-continued

Amino Acid Sequence Alignment, CGTase Numbering and Domains of Selected CGTases of Different Bacterial Origin
a *Bacillus circulans* 251 (SEQ ID NO: 70); b Bacillus sp. 1-1 (SEQ ID NO: 71); c Bacillus sp. 38-2 (SEQ ID NO: 72); d Bacillus sp. 1011 (SEQ ID NO: 73); e *Bacillus licheniformis* (SEQ ID NO: 74); f *Bacillus macerans* (SEQ ID NO: 75); g *Bacillus ohbensis* (SEQ ID NO: 76); h *Bacillus stearothermophilus* (SEQ ID NO: 77); i *Klebsiella pneumoniae* (SEQ ID NO: 78); j Thermoanaerobacter ATCC 53627 (SEQ ID NO: 2).

| No | a | b | c | d | e | f | g | h | i | j | Domain |
|---|---|---|---|---|---|---|---|---|---|---|---|
| 20 | I | I | I | I | V | I | I | I | L | I | A |
| 21 | F | V | F | F | F | V | V | V | F | V | A |
| 22 | T | T | T | T | T | T | T | V | L | T | A |
| 23 | D | D | D | D | D | D | D | D | D | D | A |
| 24 | R | R | R | R | R | R | R | R | R | R | A |
| 25 | F | F | F | F | F | F | F | F | F | F | A |
| 26 | S | S | S | S | L | A | S | V | S | L | A |
| 27 | D | D | D | D | D | D | D | D | D | D | A |
| 28 | G | G | G | G | G | G | G | G | G | G | A |
| 29 | N | N | N | N | N | D | D | N | D | N | A |
| 30 | P | P | P | P | P | R | P | T | P | P | A |
| 31 | A | G | A | A | S | T | S | S | S | S | A |
| 32 | N | N | N | N | N | N | N | N | N | N | A |
| 33 | N | N | N | N | N | N | N | N | N | N | A |
| 34 | P | P | P | P | P | P | P | P | A | P | A |
| 35 | T | S | T | T | T | A | T | S | G | T | A |
| 36 | G | G | G | G | G | G | G | G | F | G | A |
| 37 | A | A | A | A | A | D | A | A | N | D | A |
| 38 | A | I | A | A | A | A | I | L | S | L | A |
| 39 | F | F | F | F | F | F | Y | F | A | Y | A |
| 40 | D | S | D | D | D | S | S | S | T | D | A |
| 41 | G | Q | G | G | G | G | Q | S | Y | P | A |
| 42 | T | N | S | S | T | D | D | G | D | T | A |
| 43 | C | C | C | C | C | R | C | C | P | H | A |
| 44 | T | I | T | T | S | S | S | T | N | T | A |
| 45 | N | D | N | N | N | N | D | N | N | S | A |
| 46 | L | L | L | L | L | L | L | L | L | L | A |
| 47 | R | H | R | R | K | K | H | R | K | K | A |
| 48 | L | K | L | L | L | L | K | K | K | K | A |
| 49 | Y | Y | Y | Y | Y | Y | Y | Y | Y | Y | A |
| 50 | C | C | C | C | C | F | C | C | T | F | A |
| 51 | G | G | G | G | G | G | G | G | G | G | A |
| 52 | G | G | G | G | G | G | G | G | G | G | A |
| 53 | D | D | D | D | D | D | D | D | D | D | A |
| 54 | W | W | W | W | W | W | W | W | L | W | A |
| 55 | Q | Q | Q | Q | Q | Q | Q | Q | R | Q | A |
| 56 | G | G | G | G | G | G | G | G | G | G | A |
| 57 | I | I | I | I | L | I | I | I | L | I | A |
| 58 | I | I | I | I | V | I | I | I | L | I | A |
| 59 | N | D | N | N | N | D | D | N | N | N | A |
| 60 | K | K | K | K | K | K | K | K | K | K | A |
| 61 | I | I | I | I | I | I | I | I | L | I | A |
| 62 | N | N | N | N | N | N | N | N | * | N | A |
| 63 | D | D | D | D | D | D | D | D | * | D | A |
| 64 | G | G | G | G | N | G | G | G | P | G | A |
| 65 | Y | Y | Y | Y | Y | Y | Y | Y | Y | Y | A |
| 66 | L | L | L | L | F | L | L | L | L | L | A |
| 67 | T | T | T | T | S | T | T | T | K | T | A |
| 68 | G | D | G | G | D | G | D | D | S | G | A |
| 69 | M | L | M | M | L | M | L | M | L | M | A |
| 70 | G | G | G | G | G | G | G | G | G | G | A |
| 71 | V | I | I | I | V | V | I | V | V | I | A |
| 72 | T | T | T | T | T | T | T | T | T | T | A |
| 73 | A | A | A | A | A | A | A | A | S | A | A |
| 74 | I | L | I | I | L | L | I | I | I | I | A |
| 75 | W | W | W | W | W | W | W | W | W | W | A |
| 76 | I | I | I | I | I | I | I | I | I | I | A |
| 77 | S | S | S | S | S | S | S | S | T | S | A |
| 78 | Q | Q | Q | Q | Q | Q | Q | Q | P | Q | A |
| 79 | P | P | P | P | P | P | P | P | P | P | A |
| 80 | V | V | V | V | V | V | V | V | I | V | A |
| 81 | B | B | E | B | E | E | E | E | D | E | A |
| 82 | N | N | N | N | N | N | N | N | N | N | A |
| 83 | I | V | I | I | I | I | V | V | V | I | A |
| 84 | Y | Y | Y | Y | F | T | Y | F | N | Y | A |
| 85 | S | A | S | S | A | S | A | S | N | A | A |
| 86 | I | * | V | V | T | V | * | V | T | V | A |
| 87 | I | L | I | I | I | I | L | M | D | L | A |
| 88 | N | H | N | N | N | K | H | N | * | P | A |
| 89 | Y | P | Y | Y | Y | Y | P | D | * | D | A |
| 90 | S | S | S | S | S | S | S | A | A | S | A |
| 91 | G | G | G | G | G | G | S | G | A | T | A |
| 91a | * | Y | * | * | * | * | Y | * | * | F | A |
| 92 | V | * | V | V | V | V | * | * | * | G | A |
| 93 | N | * | H | N | T | N | * | G | G | G | A |
| 94 | N | * | N | N | N | N | * | S | N | S | A |
| 95 | T | T | T | T | T | T | T | A | T | T | A |
| 96 | A | S | A | A | A | S | S | S | G | S | A |
| 97 | Y | Y | Y | Y | Y | Y | Y | Y | Y | Y | A |
| 98 | H | H | H | H | H | H | H | H | H | H | A |
| 99 | G | G | G | G | G | G | G | G | G | G | A |
| 100 | Y | Y | Y | Y | Y | Y | Y | Y | Y | Y | A |
| 101 | W | W | W | W | W | W | W | W | W | W | A |
| 102 | A | A | A | A | A | A | A | A | G | A | A |
| 103 | R | R | R | R | R | R | R | R | R | R | A |
| 104 | D | D | D | D | D | D | D | D | D | D | A |
| 105 | F | Y | F | F | F | F | Y | F | Y | F | A |
| 106 | K | K | K | K | K | K | K | K | F | K | A |
| 107 | K | K | K | K | K | Q | R | K | R | K | A |
| 108 | T | T | T | T | T | T | T | T | P | I | A |
| 109 | N | N | N | N | N | N | N | N | D | N | A |
| 110 | P | P | P | P | P | D | P | P | E | P | A |
| 111 | A | Y | A | A | Y | A | F | F | H | F | A |
| 112 | Y | Y | Y | Y | F | F | Y | F | F | F | A |
| 113 | G | G | G | G | G | G | G | G | G | G | A |
| 114 | T | N | T | T | T | D | D | T | N | S | A |
| 115 | I | F | M | M | M | F | F | L | L | F | A |
| 116 | A | D | Q | Q | T | A | S | S | D | T | A |
| 117 | D | D | D | D | D | D | D | D | D | D | A |
| 118 | F | F | F | F | F | F | F | F | F | F | A |
| 119 | Q | D | K | K | Q | Q | D | Q | K | Q | A |
| 120 | N | R | N | N | N | N | R | N | E | N | A |
| 121 | L | L | L | L | L | L | L | L | L | L | A |
| 122 | I | M | I | I | V | I | M | V | T | I | A |
| 123 | A | S | D | D | T | D | D | D | S | A | A |
| 124 | A | T | T | T | T | T | T | A | L | T | A |
| 125 | A | A | A | A | A | L | A | A | M | A | A |
| 126 | H | H | H | H | H | T | H | H | H | H | A |
| 127 | A | S | A | A | A | L | S | A | S | A | A |
| 128 | K | N | H | H | K | I | N | K | P | H | A |
| 129 | N | G | N | N | G | T | G | G | D | N | A |
| 130 | I | I | I | I | I | S | I | I | Y | I | A |
| 131 | K | K | K | K | K | R | K | K | N | K | A |
| 132 | V | V | V | V | I | S | V | V | M | V | A |
| 133 | I | I | I | I | I | D | I | I | K | I | A |
| 134 | I | M | I | I | I | R | M | I | L | I | A |
| 135 | D | D | D | D | D | L | D | D | V | D | A |
| 136 | F | F | F | F | F | R | F | R | F | L | A |
| 137 | A | T | A | A | A | P | T | A | D | A | A |
| 138 | P | P | P | P | P | Q | P | P | Y | P | A |
| 139 | N | N | N | N | N | P | N | N | A | N | A |
| 140 | H | H | H | H | H | H | H | H | P | H | A |
| 141 | T | S | T | T | T | V | S | T | N | T | A |
| 142 | S | S | S | S | S | S | S | S | H | S | A |
| 143 | P | P | P | P | P | G | P | P | S | P | A |
| 144 | A | A | A | A | A | R | A | A | N | A | A |
| 145 | S | L | S | S | M | A | L | S | A | S | B |
| 146 | S | E | S | S | E | G | E | E | N | E | B |
| 147 | D | T | D | D | T | T | T | T | D | T | B |
| 148 | Q | N | D | D | D | N | D | N | E | D | B |
| 149 | P | P | P | P | T | P | P | P | N | P | B |
| 150 | S | N | S | S | S | G | S | S | E | S | B |
| 151 | F | Y | F | F | F | F | Y | Y | P | Y | B |
| 152 | A | V | A | A | A | A | A | M | G | A | B |
| 153 | E | E | E | E | E | E | B | E | A | E | B |
| 154 | N | N | N | N | N | N | N | N | L | N | B |

TABLE 1-continued

Amino Acid Sequence Alignment, CGTase Numbering and Domains of Selected CGTases of Different Bacterial Origin
a *Bacillus circulans* 251 (SEQ ID NO: 70); b Bacillus sp. 1-1 (SEQ ID NO: 71); c Bacillus sp. 38-2 (SEQ ID NO: 72); d Bacillus sp. 1011 (SEQ ID NO: 73); e *Bacillus licheniformis* (SEQ ID NO: 74); f *Bacillus macerans* (SEQ ID NO: 75); g *Bacillus ohbensis* (SEQ ID NO: 76); h *Bacillus stearothermophilus* (SEQ ID NO: 77); i *Klebsiella pneumoniae* (SEQ ID NO: 78); j Thermoanaerobacter ATCC 53627 (SEQ ID NO: 2).

| No | a | b | c | d | e | f | g | h | i | j | Domain |
|---|---|---|---|---|---|---|---|---|---|---|---|
| 155 | G | G | G | G | G | G | G | G | Y | G | B |
| 156 | R | A | R | R | K | A | A | R | R | R | B |
| 157 | L | I | L | L | L | L | V | L | D | L | B |
| 158 | Y | Y | Y | Y | Y | Y | Y | Y | G | Y | B |
| 159 | D | D | D | D | D | D | N | D | V | D | B |
| 160 | N | N | N | N | N | N | D | N | F | N | B |
| 161 | G | G | G | G | G | G | G | G | I | G | B |
| 162 | T | A | N | N | N | S | V | T | T | V | B |
| 163 | L | L | L | L | L | L | L | L | D | L | B |
| 164 | L | L | L | L | V | L | I | L | Y | L | B |
| 165 | G | G | G | G | G | G | G | G | P | G | B |
| 166 | G | N | G | G | G | A | N | G | T | G | B |
| 167 | Y | Y | Y | Y | Y | Y | Y | Y | N | Y | B |
| 168 | T | S | T | T | T | S | S | T | V | T | B |
| 169 | N | N | N | N | N | N | N | N | A | N | B |
| 170 | D | D | D | D | D | D | D | D | A | D | B |
| 171 | T | Q | T | T | T | T | P | A | N | T | B |
| 172 | Q | Q | Q | Q | N | A | N | N | T | N | B |
| 173 | N | N | N | N | G | G | N | M | G | G | B |
| 174 | L | L | L | L | Y | L | L | Y | W | Y | B |
| 175 | F | F | F | F | F | F | F | F | Y | F | B |
| 176 | H | H | H | H | H | H | H | H | H | H | B |
| 177 | H | H | H | H | H | H | H | H | H | H | B |
| 178 | N | N | Y | Y | N | N | N | N | N | Y | B |
| 179 | G | G | G | G | G | G | G | G | G | G | B |
| 180 | G | G | G | G | G | G | G | G | G | G | B |
| 181 | T | T | T | T | S | T | T | T | V | T | B |
| 182 | D | D | D | D | D | D | D | T | T | N | B |
| 182a | * | * | * | * | * | * | * | * | N | * | B |
| 183 | F | F | F | F | F | F | F | F | W | F | B |
| 184 | S | S | S | S | S | S | S | S | N | S | B |
| 185 | T | S | T | T | T | T | S | S | D | S | B |
| 186 | T | Y | I | I | L | I | Y | L | F | Y | B |
| 187 | E | E | E | E | E | E | E | E | F | E | B |
| 188 | N | D | N | N | N | D | D | D | Q | D | B |
| 189 | G | S | G | G | G | G | S | G | V | G | B |
| 190 | I | I | I | I | I | I | I | I | K | I | B |
| 191 | Y | Y | Y | Y | Y | Y | Y | Y | N | Y | B |
| 192 | K | R | K | K | K | K | R | R | H | R | B |
| 193 | N | N | N | N | N | N | N | N | N | N | B |
| 194 | L | L | L | L | L | L | L | L | L | L | B |
| 195 | Y | Y | Y | Y | Y | Y | Y | F | F | F | B |
| 196 | D | D | D | D | D | D | D | D | N | D | B |
| 197 | L | L | L | L | L | L | L | L | L | L | B |
| 198 | A | A | A | A | A | A | A | A | S | A | B |
| 199 | D | D | D | D | D | D | D | D | D | D | B |
| 200 | L | Y | L | L | L | I | Y | L | L | L | B |
| 201 | N | D | N | N | N | N | D | N | N | D | B |
| 202 | H | L | H | H | H | H | L | H | Q | Q | B |
| 203 | N | N | N | N | N | N | N | Q | S | Q | B |
| 204 | N | N | N | N | N | N | N | N | N | N | B |
| 205 | S | T | S | S | S | N | T | P | T | S | A |
| 206 | T | V | S | S | T | A | V | V | D | T | A |
| 207 | V | M | V | V | J | M | M | I | V | I | A |
| 208 | D | D | D | D | D | D | D | D | Y | D | A |
| 209 | V | Q | V | V | T | A | Q | R | Q | S | A |
| 210 | Y | Y | Y | Y | Y | Y | Y | Y | Y | Y | A |
| 211 | L | L | L | L | F | F | L | L | L | L | A |
| 212 | K | K | K | K | K | K | K | K | L | K | A |
| 213 | D | E | D | D | D | S | E | D | D | A | A |
| 214 | A | S | A | A | A | A | S | A | G | A | A |
| 215 | I | I | I | I | I | I | I | V | S | I | A |
| 216 | K | K | K | K | K | D | K | K | K | K | A |
| 217 | M | F | M | M | L | L | L | M | F | L | A |
| 218 | W | W | W | W | W | W | W | W | W | W | A |
| 219 | L | L | L | L | L | L | L | I | I | L | A |
| 220 | D | D | D | D | D | G | D | D | D | D | A |
| 221 | L | K | L | L | M | M | K | M | A | M | A |
| 222 | G | G | G | G | G | G | G | G | G | G | A |
| 223 | I | I | V | V | V | V | I | I | V | I | A |
| 224 | D | D | D | D | D | D | D | D | D | D | A |
| 225 | G | G | G | G | G | G | G | G | A | G | A |
| 226 | I | I | J | I | I | I | I | I | I | I | A |
| 227 | R | R | R | R | R | R | R | R | R | R | A |
| 228 | M | V | V | V | V | F | V | M | I | M | A |
| 229 | D | D | D | D | D | D | D | D | D | D | A |
| 230 | A | A | A | A | A | A | A | A | A | A | A |
| 231 | V | V | V | V | V | V | V | V | I | V | A |
| 232 | K | K | K | K | K | K | K | K | K | K | A |
| 233 | H | H | H | H | H | Q | H | H | H | H | A |
| 234 | M | M | M | M | M | Y | M | M | M | M | A |
| 235 | P | S | P | P | P | P | S | P | D | A | A |
| 236 | F | E | F | F | Q | F | E | F | K | F | A |
| 237 | G | G | G | G | G | G | G | G | S | G | A |
| 238 | W | W | W | W | W | W | W | W | F | W | A |
| 239 | Q | Q | Q | Q | Q | Q | Q | Q | I | Q | A |
| 240 | K | T | K | K | K | K | T | K | Q | K | A |
| 241 | S | S | S | S | N | S | S | S | K | N | A |
| 242 | F | L | F | F | W | F | L | L | W | F | A |
| 243 | M | M | M | M | M | V | M | M | T | M | A |
| 244 | A | S | S | A | S | S | S | D | S | D | A |
| 245 | A | B | T | T | S | S | D | E | D | S | A |
| 246 | V | I | I | I | I | I | I | I | I | I | A |
| 247 | N | Y | N | N | Y | Y | Y | D | Y | L | A |
| 248 | N | S | N | N | A | G | A | N | D | S | A |
| 249 | Y | H | Y | Y | H | G | H | Y | Y | Y | A |
| 249a | * | * | * | * | * | D | * | * | S | * | A |
| 250 | K | K | K | K | K | H | E | R | K | R | A |
| 251 | P | P | P | P | P | P | P | P | S | P | A |
| 252 | V | V | V | V | V | V | V | V | I | V | A |
| 253 | F | F | F | F | F | F | F | F | G | F | A |
| 254 | T | T | N | T | T | T | T | T | R | T | A |
| 255 | F | F | F | F | F | F | F | F | E | F | A |
| 256 | G | G | G | G | G | G | G | G | G | G | A |
| 257 | E | E | E | E | E | E | E | E | F | E | A |
| 258 | W | W | W | W | W | W | W | W | F | W | A |
| 259 | F | F | F | F | F | Y | F | F | F | Y | A |
| 260 | L | L | L | L | L | L | L | L | F | L | A |
| 261 | G | G | G | G | G | G | G | S | G | G | A |
| 262 | V | S | V | V | S | A | S | E | E | T | A |
| 263 | N | G | N | N | A | D | G | N | W | N | A |
| 264 | E | E | E | E | A | Q | E | E | F | E | A |
| 265 | V | V | I | I | P | T | V | V | G | V | A |
| 266 | S | D | S | S | D | D | D | D | A | D | A |
| 267 | P | P | P | P | A | G | P | A | S | P | A |
| 268 | E | Q | E | E | D | D | Q | N | A | N | A |
| 269 | N | N | Y | Y | N | N | N | N | N | N | A |
| 270 | H | H | H | H | T | I | H | H | T | T | A |
| 271 | K | H | Q | Q | D | K | H | Y | T | Y | A |
| 272 | F | F | F | F | F | F | F | F | T | F | A |
| 273 | A | A | A | A | A | A | A | A | G | A | A |
| 274 | N | N | N | N | N | N | N | N | V | N | A |
| 275 | E | E | E | E | E | E | E | E | D | E | A |
| 276 | S | S | S | S | S | S | S | S | G | S | A |
| 277 | G | G | G | G | G | G | G | G | N | G | A |
| 278 | M | M | M | M | M | M | M | M | A | M | A |
| 279 | S | N | S | S | S | N | S | S | I | S | A |
| 280 | L | L | L | L | L | L | L | L | D | L | A |
| 281 | L | L | L | L | L | L | L | L | Y | L | A |
| 282 | D | D | D | D | D | D | D | D | A | D | A |
| 283 | F | F | F | F | F | F | F | F | N | F | A |
| 284 | R | Q | P | R | R | E | Q | R | T | R | A |
| 285 | F | F | F | F | F | Y | F | F | S | F | A |
| 286 | A | G | A | A | N | A | G | G | G | A | A |
| 287 | Q | Q | Q | Q | S | Q | Q | Q | S | Q | A |
| 288 | K | T | K | K | A | E | T | K | A | K | A |

TABLE 1-continued

Amino Acid Sequence Alignment, CGTase Numbering and Domains of Selected CGTases of Different Bacterial Origin
a *Bacillus circulans* 251 (SEQ ID NO: 70); b Bacillus sp. 1-1 (SEQ ID NO: 71); c Bacillus sp. 38-2 (SEQ ID NO: 72); d Bacillus sp. 1011 (SEQ ID NO: 73); e *Bacillus licheniformis* (SEQ ID NO: 74); f *Bacillus macerans* (SEQ ID NO: 75); g *Bacillus ohbensis* (SEQ ID NO: 76); h *Bacillus stearothermophilus* (SEQ ID NO: 77); i *Klebsiella pneumoniae* (SEQ ID NO: 78); j Thermoanaerobacter ATCC 53627 (SEQ ID NO: 2).

| No | a | b | c | d | e | f | g | h | i | j | Domain |
|---|---|---|---|---|---|---|---|---|---|---|---|
| 289 | V | I | A | A | V | V | I | L | L | V | A |
| 290 | R | R | R | R | R | R | R | R | L | R | A |
| 291 | Q | N | Q | Q | N | E | D | Q | D | Q | A |
| 292 | V | V | V | V | V | V | V | V | F | V | A |
| 293 | F | L | F | F | F | F | L | L | G | F | A |
| 294 | R | K | R | R | R | R | M | R | F | R | A |
| 295 | D | D | D | D | D | D | D | N | R | D | A |
| 296 | N | R | N | N | N | K | G | N | D | N | A |
| 297 | T | T | T | T | T | T | S | S | T | T | A |
| 298 | D | S | D | D | S | E | S | D | L | D | A |
| 299 | N | N | N | N | N | T | N | N | E | T | A |
| 300 | M | W | M | M | M | M | W | W | R | M | A |
| 301 | Y | Y | Y | Y | Y | K | Y | Y | V | Y | A |
| 302 | G | D | G | G | A | D | D | G | L | G | A |
| 303 | L | F | L | L | L | L | F | F | V | L | A |
| 304 | K | N | K | K | D | Y | N | N | G | D | A |
| 305 | A | E | A | A | S | E | E | Q | R | S | A |
| 306 | M | M | M | M | M | V | M | M | S | M | A |
| 307 | L | I | L | L | L | L | I | I | G | I | A |
| 308 | E | T | E | E | T | A | A | Q | N | Q | A |
| 309 | G | S | G | G | A | S | S | D | T | S | A |
| 310 | S | T | S | S | T | T | T | T | M | T | A |
| 311 | A | E | E | B | A | B | B | A | K | A | A |
| 312 | A | K | V | V | A | S | E | S | T | A | A |
| 313 | D | E | D | D | D | Q | D | A | L | D | A |
| 314 | Y | Y | Y | Y | Y | Y | Y | Y | N | Y | A |
| 315 | A | N | A | A | N | D | D | D | S | N | A |
| 316 | Q | E | Q | Q | Q | Y | E | B | Y | F | A |
| 317 | V | V | V | V | V | I | V | V | L | I | A |
| 318 | D | I | N | N | N | N | I | L | I | N | A |
| 319 | D | D | D | D | D | N | D | D | K | D | A |
| 320 | Q | Q | Q | Q | Q | M | Q | Q | R | M | A |
| 321 | V | V | V | V | V | V | V | V | Q | V | A |
| 322 | T | T | T | T | T | T | T | T | T | T | A |
| 323 | F | F | F | F | F | F | F | F | V | F | A |
| 324 | I | I | I | I | I | I | I | I | F | I | A |
| 325 | D | D | D | D | D | D | D | D | T | D | A |
| 326 | N | N | N | N | N | N | N | N | S | N | A |
| 327 | H | H | H | H | H | H | H | H | D | H | A |
| 328 | D | D | D | D | D | D | D | D | D | D | A |
| 329 | M | M | M | M | M | M | M | M | W | M | A |
| 330 | E | S | E | E | D | D | S | D | Q | D | A |
| 331 | R | R | R | R | R | R | R | R | V | R | A |
| 332 | F | F | F | F | F | F | F | F | V | F | A |
| 333 | H | S | H | H | K | Q | S | M | F | Y | A |
| 334 | A | V | T | T | T | V | F | I | M | T | A |
| 335 | S | G | S | S | S | A | B | D | D | G | A |
| 336 | N | S | N | N | A | G | Q | G | N | * | A |
| 337 | A | S | G | G | V | S | S | G | H | G | A |
| 338 | N | S | D | D | N | G | S | D | D | S | A |
| 339 | R | N | R | R | N | T | N | P | M | T | A |
| 340 | R | R | R | R | R | R | R | R | A | R | A |
| 341 | K | Q | K | K | R | A | H | K | R | P | A |
| 342 | L | T | L | L | L | T | T | V | I | V | A |
| 343 | E | D | E | E | E | E | D | D | G | E | A |
| 344 | Q | M | Q | Q | Q | Q | I | M | T | Q | A |
| 345 | A | A | A | A | A | A | A | A | A | A | A |
| 346 | L | L | L | L | L | L | L | L | L | L | A |
| 347 | A | A | A | A | A | A | A | A | R | A | A |
| 348 | F | V | F | F | F | L | V | V | S | F | A |
| 349 | T | L | T | T | T | T | L | L | N | T | A |
| 350 | L | L | L | L | L | L | L | L | A | L | A |
| 351 | T | T | T | T | T | T | T | T | T | T | A |
| 352 | S | S | S | S | S | S | S | S | T | S | A |
| 353 | R | R | R | R | R | R | R | R | F | R | A |
| 354 | G | G | G | G | G | G | G | G | G | G | A |
| 355 | V | V | V | V | V | V | V | V | P | V | A |
| 356 | P | P | P | P | P | P | P | P | G | P | A |
| 357 | A | T | A | A | A | A | T | N | N | A | A |
| 358 | I | I | I | I | I | I | I | I | N | I | A |
| 359 | Y | Y | Y | Y | Y | Y | Y | Y | E | Y | A |
| 360 | Y | Y | Y | Y | Y | Y | Y | Y | T | Y | A |
| 361 | G | G | G | G | G | G | G | G | G | G | A |
| 362 | T | T | S | S | T | T | T | T | G | T | A |
| 363 | E | E | E | E | E | E | E | E | S | E | A |
| 364 | Q | Q | Q | Q | Q | Q | Q | Q | Q | Q | A |
| 365 | Y | Y | Y | Y | Y | Y | Y | Y | S | Y | A |
| 366 | M | V | M | M | L | M | L | M | E | M | A |
| 367 | S | T | S | S | T | T | T | T | A | T | A |
| 368 | G | G | G | G | G | G | G | G | F | G | A |
| 369 | G | G | G | G | N | D | G | N | A | N | A |
| 370 | T | N | N | N | G | G | N | G | Q | G | A |
| 371 | D | D | D | D | D | D | D | D | K | D | A |
| 372 | P | P | P | P | P | P | P | P | R | P | A |
| 373 | D | E | D | D | D | N | E | N | I | Y | A |
| 374 | N | N | N | N | N | N | N | N | D | N | A |
| 375 | R | R | R | R | R | R | R | R | L | R | A |
| 376 | A | K | A | A | G | A | K | K | G | A | A |
| 377 | R | P | R | R | K | M | P | M | L | M | A |
| 378 | I | L | I | L | M | M | M | M | V | M | A |
| 379 | P | K | P | P | P | T | S | S | A | T | A |
| 380 | S | T | S | S | S | S | D | S | T | S | A |
| 381 | F | F | F | F | F | F | F | F | M | F | A |
| 382 | S | D | S | S | S | N | D | N | T | D | A |
| 383 | T | R | T | T | K | T | R | K | V | T | A |
| 384 | S | S | T | T | S | G | T | N | R | T | A |
| 385 | T | T | T | T | T | T | T | T | G | T | A |
| 386 | T | N | T | T | T | T | N | R | I | T | A |
| 387 | A | S | A | A | A | A | S | A | P | A | A |
| 388 | Y | Y | Y | Y | F | Y | Y | Y | A | Y | A |
| 389 | Q | Q | Q | Q | N | K | Q | Q | I | N | A |
| 390 | V | I | V | V | V | V | I | V | Y | V | A |
| 391 | I | I | I | I | I | I | I | I | Y | I | A |
| 392 | Q | S | Q | Q | S | Q | S | Q | G | K | A |
| 393 | K | K | K | K | K | A | T | K | T | K | A |
| 394 | L | L | L | L | L | L | L | L | E | L | A |
| 395 | A | A | A | A | A | A | A | S | H | A | A |
| 396 | P | S | P | P | P | P | S | S | Y | P | A |
| 397 | L | L | L | L | L | L | L | L | A | L | A |
| 398 | R | R | R | R | R | R | R | R | A | R | A |
| 399 | K | Q | K | K | K | K | Q | R | N | K | A |
| 400 | C | T | S | S | S | S | N | N | F | S | A |
| 401 | N | N | N | N | N | N | N | N | T | N | A |
| 402 | P | S | P | P | P | P | P | P | S | P | A |
| 403 | A | A | A | A | A | A | A | A | N | A | A |
| 404 | I | L | I | I | I | I | L | L | S | I | A |
| 405 | A | G | A | A | A | A | G | A | F | A | A |
| 406 | Y | Y | Y | Y | Y | Y | Y | Y | G | Y | A |
| 407 | G | G | G | G | G | G | G | G | Q | G | C |
| 408 | S | T | S | S | S | T | N | D | V | T | C |
| 409 | T | T | T | T | T | T | T | T | G | Q | C |
| 410 | Q | T | Q | H | Q | T | S | E | S | K | C |
| 411 | E | E | E | E | Q | E | E | Q | D | Q | C |
| 412 | R | R | R | R | R | R | R | R | P | R | C |
| 413 | W | W | W | W | W | W | W | W | Y | W | C |
| 414 | I | L | I | I | I | V | I | I | N | I | C |
| 415 | N | N | N | N | N | N | N | N | R | N | C |
| 416 | N | E | N | N | N | N | S | G | E | N | C |
| 417 | D | D | D | D | D | D | D | D | k | D | C |
| 418 | V | I | V | V | V | V | V | V | M | V | C |
| 419 | L | Y | I | I | Y | L | Y | Y | P | Y | C |
| 420 | I | I | I | I | I | I | I | V | G | I | C |
| 421 | Y | Y | Y | Y | Y | I | Y | Y | F | Y | C |
| 422 | E | E | E | E | E | E | E | E | D | E | C |
| 423 | R | R | R | R | R | R | R | R | T | R | C |
| 424 | K | T | K | K | K | K | S | Q | E | Q | C |

TABLE 1-continued

Amino Acid Sequence Alignment, CGTase Numbering and Domains of Selected CGTases of Different Bacterial Origin a *Bacillus circulans* 251 (SEQ ID NO: 70); b Bacillus sp. 1-1 (SEQ ID NO: 71); c Bacillus sp. 38-2 (SEQ ID NO: 72); d Bacillus sp. 1011 (SEQ ID NO: 73); e *Bacillus licheniformis* (SEQ ID NO: 74); f *Bacillus macerans* (SEQ ID NO: 75); g *Bacillus ohbensis* (SEQ ID NO: 76); h *Bacillus stearothermophilus* (SEQ ID NO: 77); i *Klebsiella pneumoniae* (SEQ ID NO: 78); j Thermoanaerobacter ATCC 53627 (SEQ ID NO: 2).

| No | a | b | c | d | e | f | g | h | i | j | Domain |
|---|---|---|---|---|---|---|---|---|---|---|---|
| 425 | F | F | F | F | F | F | F | F | S | F | C |
| 426 | G | G | G | G | G | G | G | G | E | G | C |
| 427 | S | N | N | N | K | S | D | K | A | N | C |
| 428 | N | S | N | N | S | S | S | D | F | N | C |
| 429 | V | I | V | V | V | A | V | V | S | V | C |
| 430 | A | V | A | A | A | A | V | V | I | A | C |
| 431 | V | L | V | V | V | L | L | L | I | L | C |
| 432 | V | T | V | V | V | V | T | V | K | V | C |
| 433 | A | A | A | A | A | A | A | R | T | A | C |
| 434 | V | V | i | I | V | I | V | V | L | I | C |
| 435 | N | N | N | N | N | N | N | N | G | N | C |
| 436 | R | S | R | R | R | R | S | R | D | R | C |
| 437 | N | * | N | N | N | N | * | S | L | N | C |
| 438 | L | S | M | M | L | S | G | S | R | L | C |
| 439 | N | N | N | N | T | S | D | S | K | S | C |
| 440 | A | S | T | T | T | A | T | S | S | T | C |
| 441 | P | N | P | P | P | A | S | N | S | S | C |
| 442 | A | Q | A | A | T | Y | Y | Y | P | Y | C |
| 443 | S | T | S | S | S | P | T | S | A | Y | C |
| 444 | I | I | I | I | I | I | I | I | I | I | C |
| 445 | S | T | T | T | T | S | N | T | Q | T | C |
| 446 | G | N | G | G | N | G | N | G | N | G | C |
| 447 | L | L | L | L | L | L | L | L | G | L | C |
| 448 | V | N | V | V | N | L | N | F | T | Y | C |
| 449 | T | T | T | T | T | S | T | T | Y | T | C |
| 450 | S | S | S | S | S | S | S | A | T | A | C |
| 451 | L | L | L | L | L | L | L | L | E | L | C |
| 452 | P | P | P | R | P | P | P | P | L | P | C |
| 453 | Q | Q | Q | R | S | A | Q | A | W | A | C |
| 454 | G | G | G | A | G | G | G | G | V | G | C |
| 455 | S | N | S | S | T | T | Q | T | N | T | C |
| 456 | Y | Y | Y | Y | Y | Y | Y | Y | D | Y | C |
| 457 | N | T | N | N | T | S | T | T | D | S | C |
| 458 | D | D | D | D | D | D | D | D | I | D | C |
| 459 | V | E | V | V | V | V | E | Q | L | M | C |
| 460 | L | L | L | L | L | L | L | L | V | L | C |
| 461 | G | Q | G | G | G | N | Q | Q | F | G | C |
| 462 | G | Q | G | G | G | G | Q | G | E | G | C |
| 463 | L | R | I | I | V | L | L | L | R | L | C |
| 464 | L | L | L | L | L | L | L | L | R | L | C |
| 465 | N | D | N | N | N | N | D | D | S | N | C |
| 466 | G | G | G | G | G | G | G | G | G | G | C |
| 467 | N | N | N | N | N | N | N | N | N | S | C |
| 468 | T | T | T | T | N | S | E | T | D | S | C |
| 469 | L | I | L | L | I | I | I | I | I | I | C |
| 470 | S | T | T | T | T | T | T | Q | V | T | C |
| 471 | V | V | V | V | S | V | V | V | I | V | C |
| 472 | G | N | G | G | S | G | N | G | V | S | C |
| 473 | S | A | A | A | G | S | S | S | A | S | C |
| 474 | G | N | G | G | G | N | N | L | N | G | C |
| 475 | G | G | G | G | N | G | G | N | G | N | C |
| 476 | A | A | A | A | I | A | A | S | R | S | C |
| 477 | A | V | A | A | * | V | V | V | G | V | C |
| 478 | S | N | S | S | S | T | D | N | E | T | C |
| 479 | N | S | N | N | S | N | S | A | A | P | C |
| 480 | F | F | F | F | F | F | F | N | F | F | C |
| 481 | T | Q | T | T | T | T | Q | D | T | T | C |
| 482 | L | L | L | L | L | L | L | L | I | L | C |
| 483 | A | R | A | A | A | A | S | G | N | A | C |
| 484 | N | A | P | P | A | A | A | P | V | P | C |
| 485 | G | N | G | G | G | G | N | G | K | G | C |
| 486 | G | S | G | G | A | G | G | B | N | E | C |
| 487 | T | V | T | T | T | T | V | V | I | V | C |
| 488 | A | A | A | A | A | A | S | G | A | A | C |
| 489 | V | V | V | V | V | V | V | V | V | V | C |
| 490 | W | W | W | W | W | W | W | W | P | W | C |
| 491 | Q | Q | Q | Q | Q | Q | Q | A | N | Q | C |
| 492 | Y | V | Y | Y | Y | Y | I | Y | G | Y | C |
| 493 | T | S | T | T | T | T | T | S | V | V | C |
| 494 | A | N | T | T | A | A | E | A | Y | S | C |
| 495 | A | W | D | D | S | P | B | T | P | T | C |
| 496 | T | S | A | A | E | E | H | E | S | T | D |
| 497 | A | T | T | T | T | T | A | S | L | N | D |
| 498 | T | S | A | T | T | S | S | T | I | P | D |
| 499 | P | P | P | P | P | P | P | P | G | P | D |
| 500 | T | L | I | I | T | A | L | I | N | L | D |
| 501 | I | I | N | I | I | I | I | I | N | I | D |
| 502 | G | G | G | G | G | G | G | G | S | G | D |
| 503 | H | Q | N | N | H | N | H | H | V | H | D |
| 504 | V | V | V | V | V | V | V | V | S | V | D |
| 505 | G | G | G | G | G | G | G | G | V | G | D |
| 506 | P | P | P | P | P | P | P | P | A | P | D |
| 507 | M | M | M | M | V | T | M | M | N | T | D |
| 508 | M | M | M | M | M | M | M | M | K | M | D |
| 509 | A | G | A | A | G | G | G | G | R | T | D |
| 510 | K | K | K | K | K | Q | K | Q | T | K | D |
| 511 | P | A | A | P | P | P | H | V | T | A | D |
| 512 | G | G | G | G | G | G | G | G | L | G | D |
| 513 | V | N | V | V | N | N | N | N | H | T | D |
| 514 | T | T | T | T | V | I | T | Q | L | T | D |
| 515 | I | I | I | I | V | V | V | V | M | I | D |
| 516 | T | T | T | T | T | T | T | T | Q | T | D |
| 517 | I | V | I | I | I | I | I | I | N | I | D |
| 518 | D | S | D | D | D | D | T | D | E | D | D |
| 519 | G | G | G | G | G | G | G | G | A | G | D |
| 520 | R | E | R | R | R | R | B | E | V | R | D |
| 521 | G | A | G | G | G | G | G | G | V | G | D |
| 522 | F | F | * | F | F | F | F | F | I | F | D |
| 523 | G | S | S | G | G | G | G | G | R | G | D |
| 524 | S | D | A | S | S | G | D | T | S | T | D |
| 525 | S | E | R | G | A | T | N | N | Q | T | D |
| 526 | K | R | Q | K | K | A | E | T | S | A | D |
| 527 | G | G | G | G | G | G | G | D | G | D | D |
| 528 | T | S | T | T | T | T | S | T | D | Q | D |
| 529 | V | V | V | V | V | V | V | V | A | V | D |
| 530 | Y | L | Y | Y | Y | Y | L | K | E | L | D |
| 531 | F | F | F | F | F | F | F | F | N | F | D |
| 532 | G | D | G | G | G | G | D | G | P | G | D |
| 533 | T | T | T | T | T | T | S | T | T | T | D |
| 534 | T | T | T | T | T | T | D | T | V | T | D |
| 535 | A | S | A | A | A | A | F | A | Q | P | D |
| 536 | V | S | V | V | V | V | S | A | S | A | D |
| 537 | S | E | T | T | T | T | D | N | I | T | D |
| 538 | G | * | G | G | G | G | * | * | N | * | D |
| 539 | A | * | A | A | S | S | * | F | * | * | D |
| 540 | D | * | D | D | A | G | * | * | T | * | D |
| 541 | I | I | I | I | I | I | V | V | C | I | D |
| 542 | T | I | V | V | T | V | L | V | N | V | D |
| 543 | S | S | A | A | S | S | S | S | N | S | D |
| 544 | W | W | W | W | W | W | W | W | G | W | D |
| 545 | E | S | E | E | E | E | S | S | Y | E | D |
| 546 | D | N | D | D | D | D | D | N | T | D | D |
| 547 | T | T | T | T | T | T | T | T | N | I | D |
| 548 | Q | K | Q | Q | Q | Q | K | Q | S | E | D |
| 549 | I | I | I | I | I | I | I | I | G | V | D |
| 550 | K | S | Q | Q | K | K | E | V | Q | K | D |
| 551 | V | V | V | V | V | A | V | V | S | V | D |
| 552 | K | K | K | K | T | V | S | A | V | K | D |
| 553 | I | V | I | I | I | I | V | V | Y | V | D |
| 554 | P | P | L | P | P | P | P | P | I | P | D |
| 555 | A | N | R | A | A | P | K | D | N | A | D |
| 556 | V | V | V | V | V | V | V | V | G | L | D |
| 557 | A | A | P | P | A | A | T | S | N | T | D |
| 558 | G | G | G | G | G | A | A | P | I | P | D |
| 559 | G | G | G | G | G | G | G | P | G | G | D |
| 560 | N | Y | I | I | D | K | H | K | Q | K | D |

TABLE 1-continued

Amino Acid Sequence Alignment, CGTase Numbering and Domains of Selected CGTases of Different Bacterial Origin
a *Bacillus circulans* 251 (SEQ ID NO: 70); b *Bacillus* sp. 1-1 (SEQ ID NO: 71); c *Bacillus* sp. 38-2 (SEQ ID NO: 72); d *Bacillus* sp. 1011 (SEQ ID NO: 73); e *Bacillus licheniformis* (SEQ ID NO: 74); f *Bacillus macerans* (SEQ ID NO: 75); g *Bacillus ohbensis* (SEQ ID NO: 76); h *Bacillus stearothermophilus* (SEQ ID NO: 77); i *Klebsiella pneumoniae* (SEQ ID NO: 78); j *Thermoanaerobacter* ATCC 53627 (SEQ ID NO: 2).

| No | a | b | c | d | e | f | g | h | i | j | Domain |
|---|---|---|---|---|---|---|---|---|---|---|---|
| 561 | Y | Y | Y | Y | Y | T | Y | Y | L | Y | D |
| 562 | N | D | D | D | A | G | D | N | G | N | D |
| 563 | I | L | I | I | V | V | I | I | G | I | D |
| 564 | K | S | R | R | K | S | S | T | W | T | D |
| 565 | V | V | V | V | V | V | V | V | D | L | D |
| 566 | A | V | A | A | A | K | V | Q | L | K | D |
| 567 | N | T | N | N | A | T | N | S | T | T | D |
| 568 | A | A | A | A | * | S | A | S | K | A | D |
| 569 | A | A | A | A | N | S | G | S | A | S | D |
| 570 | G | N | G | G | G | G | D | G | V | G | D |
| 571 | T | I | A | A | V | T | S | Q | K | V | D |
| 572 | A | K | A | A | N | A | Q | T | I | T | D |
| 573 | S | S | S | S | S | S | S | S | S | S | D |
| 574 | N | P | N | N | N | N | P | A | P | N | D |
| 575 | V | T | I | I | A | T | T | A | T | S | D |
| 576 | Y | Y | Y | Y | Y | F | Y | Y | Q | Y | D |
| 577 | D | K | D | D | N | K | D | D | Y | N | D |
| 578 | N | E | N | N | D | S | K | N | P | N | D |
| 579 | F | F | F | F | F | F | F | F | Q | I | D |
| 580 | B | E | E | E | T | N | B | E | W | N | D |
| 581 | V | V | V | V | I | V | V | V | S | V | D |
| 582 | L | L | L | L | L | L | L | L | A | L | D |
| 583 | S | S | T | T | S | T | T | T | S | T | D |
| 584 | G | G | G | G | G | G | G | N | L | G | E |
| 585 | D | N | D | D | D | D | D | D | E | N | E |
| 586 | Q | Q | Q | Q | Q | Q | Q | Q | L | Q | E |
| 587 | V | V | V | V | V | V | V | V | P | V | E |
| 588 | S | S | T | T | S | T | S | S | S | C | E |
| 589 | V | V | V | V | V | V | I | V | D | V | E |
| 590 | R | R | R | R | R | R | R | R | L | R | E |
| 591 | F | F | F | F | F | F | F | F | N | F | E |
| 592 | V | G | V | V | V | L | A | V | V | V | E |
| 593 | V | V | I | I | I | V | V | V | E | V | E |
| 594 | N | N | N | N | N | N | N | N | W | N | E |
| 595 | N | N | N | N | Q | N | N | K | N | N | E |
| 596 | A | A | A | A | A | A | A | A | C | A | E |
| 597 | T | T | T | T | T | N | T | T | V | T | E |
| 598 | T | T | T | T | T | T | T | T | K | T | E |
| 599 | A | S | A | A | A | N | S | N | R | V | E |
| 600 | L | P | L | L | L | Y | L | L | N | W | E |
| 601 | G | G | G | G | G | G | G | G | E | G | E |
| 602 | Q | T | Q | Q | E | T | T | Q | T | E | E |
| 603 | N | N | N | N | N | N | N | N | N | N | E |
| 604 | V | L | V | V | I | V | L | I | P | V | E |
| 605 | Y | Y | F | F | Y | Y | Y | Y | T | Y | E |
| 606 | L | I | L | L | L | L | M | I | A | L | E |
| 607 | T | V | T | T | T | V | V | V | N | T | E |
| 608 | G | G | G | G | G | G | G | G | V | G | E |
| 609 | S | N | N | N | N | N | N | N | E | N | E |
| 610 | V | V | V | V | V | A | V | V | W | V | E |
| 611 | S | N | S | S | S | S | A | N | Y | Q | E |
| 612 | E | E | E | E | E | E | E | E | S | E | E |
| 613 | L | L | L | L | L | L | L | L | G | L | E |
| 614 | G | G | G | G | G | G | G | G | A | G | E |
| 615 | N | N | N | N | N | T | N | N | N | N | E |
| 616 | W | W | W | W | W | W | W | W | N | W | E |
| 617 | D | D | D | D | T | D | D | D | Q | D | E |
| 618 | P | A | P | P | T | P | P | T | F | T | E |
| 619 | A | D | N | N | G | N | D | S | N | S | E |
| 620 | K | N | N | N | A | K | Q | K | S | K | E |
| 621 | A | A | A | A | A | A | A | A | N | A | E |
| 621a | * | * | * | * | S | * | * | * | * | * | E |
| 622 | I | I | I | I | I | I | I | I | D | I | E |
| 623 | G | G | G | G | G | G | G | G | T | G | E |
| 624 | P | P | P | P | P | P | P | P | Q | P | E |
| 625 | M | M | M | M | A | M | M | M | T | M | E |
| 626 | Y | F | Y | Y | F | Y | P | F | T | F | E |
| 627 | N | N | N | N | N | N | N | N | N | N | E |
| 628 | Q | Q | Q | Q | Q | Q | Q | Q | G | Q | E |
| 629 | V | V | V | V | V | V | V | V | S | V | E |
| 630 | V | M | V | V | I | I | M | V | F | V | E |
| 631 | Y | Y | Y | Y | H | A | Y | Y | F | Y | E |
| 632 | Q | Q | Q | Q | A | K | Q | S | Q | Q | E |
| 633 | Y | Y | Y | Y | Y | Y | Y | Y | Y | Y | E |
| 634 | P | P | P | P | P | P | P | P | P | P | E |
| 635 | N | T | T | T | T | T | S | T | T | T | E |
| 636 | W | W | W | W | W | W | W | W | W | W | E |
| 637 | Y | Y | Y | Y | Y | Y | Y | Y | Y | Y | E |
| 638 | Y | Y | Y | Y | Y | Y | Y | Y | I | Y | E |
| 639 | D | D | D | D | D | D | D | D | D | D | E |
| 640 | V | I | V | V | V | V | V | I | V | V | E |
| 641 | S | S | S | S | S | S | S | S | S | S | E |
| 642 | V | V | V | V | V | V | V | V | V | V | E |
| 643 | P | P | P | P | P | P | P | P | P | P | E |
| 644 | A | A | A | A | A | A | A | A | E | A | E |
| 645 | G | G | G | G | G | G | E | G | G | G | E |
| 646 | K | K | Q | Q | K | T | E | K | T | T | E |
| 647 | T | N | T | T | Q | K | N | T | T | T | E |
| 648 | I | L | I | I | L | L | L | L | I | I | E |
| 649 | E | E | E | E | E | D | E | E | E | E | E |
| 650 | F | Y | F | F | F | F | Y | F | F | F | E |
| 651 | K | K | K | K | K | K | K | K | K | K | E |
| 652 | F | Y | F | F | F | F | F | F | F | F | E |
| 653 | L | I | L | L | F | I | I | I | I | I | E |
| 654 | K | K | K | K | K | K | K | K | K | K | E |
| 655 | K | K | K | K | K | K | K | K | K | K | E |
| 656 | Q | D | Q | Q | N | G | D | D | N | N | E |
| 657 | G | Q | G | G | G | G | S | S | S | G | E |
| 658 | S | N | S | S | A | G | S | Q | S | S | E |
| 658a | * | G | * | * | * | * | G | G | * | * | E |
| 659 | T | N | T | T | T | T | N | N | T | T | E |
| 660 | V | V | V | V | I | V | V | V | V | V | E |
| 661 | T | V | T | T | T | T | T | V | T | T | E |
| 662 | W | W | W | W | W | W | W | W | W | W | E |
| 663 | E | Q | E | B | B | B | B | B | E | E | E |
| 664 | G | S | G | G | G | G | S | S | S | G | E |
| 665 | G | G | G | G | G | G | G | G | G | G | E |
| 666 | S | N | A | A | S | G | N | S | Y | N | E |
| 667 | N | N | N | N | N | N | N | N | N | N | E |
| 668 | H | R | R | R | H | H | H | H | H | H | E |
| 669 | T | T | T | T | T | T | T | T | V | V | E |
| 670 | F | Y | P | P | P | Y | Y | Y | Y | Y | E |
| 671 | T | T | T | T | T | T | T | T | T | T | E |
| 672 | A | S | T | T | T | T | T | T | T | T | E |
| 673 | P | P | P | P | P | P | P | P | P | P | E |
| 674 | S | T | T | T | T | A | A | T | T | T | E |
| 675 | S | T | S | S | S | S | S | T | N | S | E |
| 676 | G | G | G | G | G | G | G | T | G | T | E |
| 677 | T | T | T | T | T | T | V | T | T | T | E |
| 678 | A | D | A | A | A | G | D | G | A | A | E |
| 679 | T | T | T | T | T | T | T | T | K | T | E |
| 680 | I | V | V | V | V | V | V | V | I | V | E |
| 681 | N | M | N | N | T | T | N | L | I | I | E |
| 682 | V | I | V | V | I | V | V | V | I | V | E |
| 683 | N | N | N | N | N | D | N | D | D | D | E |
| 684 | W | W | W | W | W | W | W | W | W | W | E |
| 685 | Q | | Q | Q | Q | Q | Q | Q | Q | Q | E |
| 686 | P | | P | P | P | | N | | N | P | E |

*Amino acid residue absent in this position

BRIEF DESCRIPTION OF THE DRAWINGS

The present invention is further illustrated by reference to the accompanying drawings, in which:

FIG. 7 shows the product formation (○ α-cyclodextrin formation; □ β-cyclodextrin formation, and Δ γ-cyclodextrin formation) of two CGTase variants of the invention (N193G, FIG. 7B, and Y89G, FIG. 7C) compared to the wild-type enzyme (from *Bacillus circulans* Strain 251, FIG. 7A) during incubation for 0 to 45 hours;

FIG. 9 shows the product formation (○ α-cyclodextrin formation; □ β-cyclodextrin formation, and Δ γ-cyclodextrin formation) of two CGTase variants of the invention (N193G, FIG. 9B, and Y89G, FIG. 9C) compared to the wild-type enzyme (from *Bacillus circulans* Strain 251, FIG. 9A) during incubation for 0 to 10 hours; and FIG. 10 shows the product formation (○ α-cyclodextrin formation; □ β-cyclodextrin formation, and Δ γ-cyclodextrin formation) of two CGTase variants of the invention (145aI, FIG. 10B, and D371G, FIG. 10C) compared to the wild-type enzyme (from *Bacillus circulans* Strain 251, FIG. 10A) during incubation for 0 to 10 hours.

DETAILED DISCLOSURE OF THE INVENTION
Methods of Making CGTase Variants

In its first aspect, the present invention provides a method of modifying the substrate binding and/or increasing the product selectivity of a CGTase enzyme, thereby obtaining a CGTase variant having a modified substrate binding capability and/or an increased product selectivity, as compared to the precursor enzyme.

In the context of this invention, a CGTase variant of modified substrate binding capability is meant to describe a CGTase variant that is able to more efficiently act on its substrate, and/or a CGTase variant that is less affected by product inhibition. In the context of this invention, product inhibition is meant to describe the phenomenon that increasing amounts of product reduce or even inhibit the substrate conversion. It is desirable to obtain CGTase variants that are less affected by product inhibition (i.e. variants of reduced product inhibition).

Moreover, in the context of this invention, a CGTase variant of increased product selectivity is meant to describe a CGTase variant that is able to more selectively produce any of the various cyclodextrins thereby increasing the ratio of the desired product, as compared to the precursor enzyme.

The present invention is based on the concept of removing and/or introducing "obstacles" in the subsites of the active site cleft, the substrate binding cleft, or the groove leading to these clefts, thereby facilitating introduction of the substrate and its disposition in such a way that products of a predetermined size are obtained, and in such a way that substrate binding is not inhibited by the product.

By modifying the substrate binding of a CGTase enzyme, its product selectivity can be modified in order that the CGTase variant is able to more selectively produce any of the various cyclodextrins, α-, β- and γ-cyclodextrins. Even CGTases capable of producing δ-, ε-, and ζ-cyclodextrins with 9, 10 and 11 glucose units, respectively, may be obtained. Modification of the substrate binding of a CGTase may also reduce the tendency of product inhibition, thereby increasing the cyclodextrin yield of the CGTase variant.

The concept of the invention may be expressed differently as the modification of enzyme-substrate side chain intermolecular interactions. By introducing specific mutations according to the invention, the intermolecular interactions between substrate and CGTase can be changed in order to direct the substrate to a specific location in the active site cleft, thereby obtaining a cyclic or linear product of pre-defined size, preferably α-, a β- or a γ-cyclodextrin, or δ-, ε, and ζ-cyclodextrins, or a linear oligosaccharide of similar size, preferably of 2–12 glucose units, more preferred 2–9 glucose units.

Figure 1:
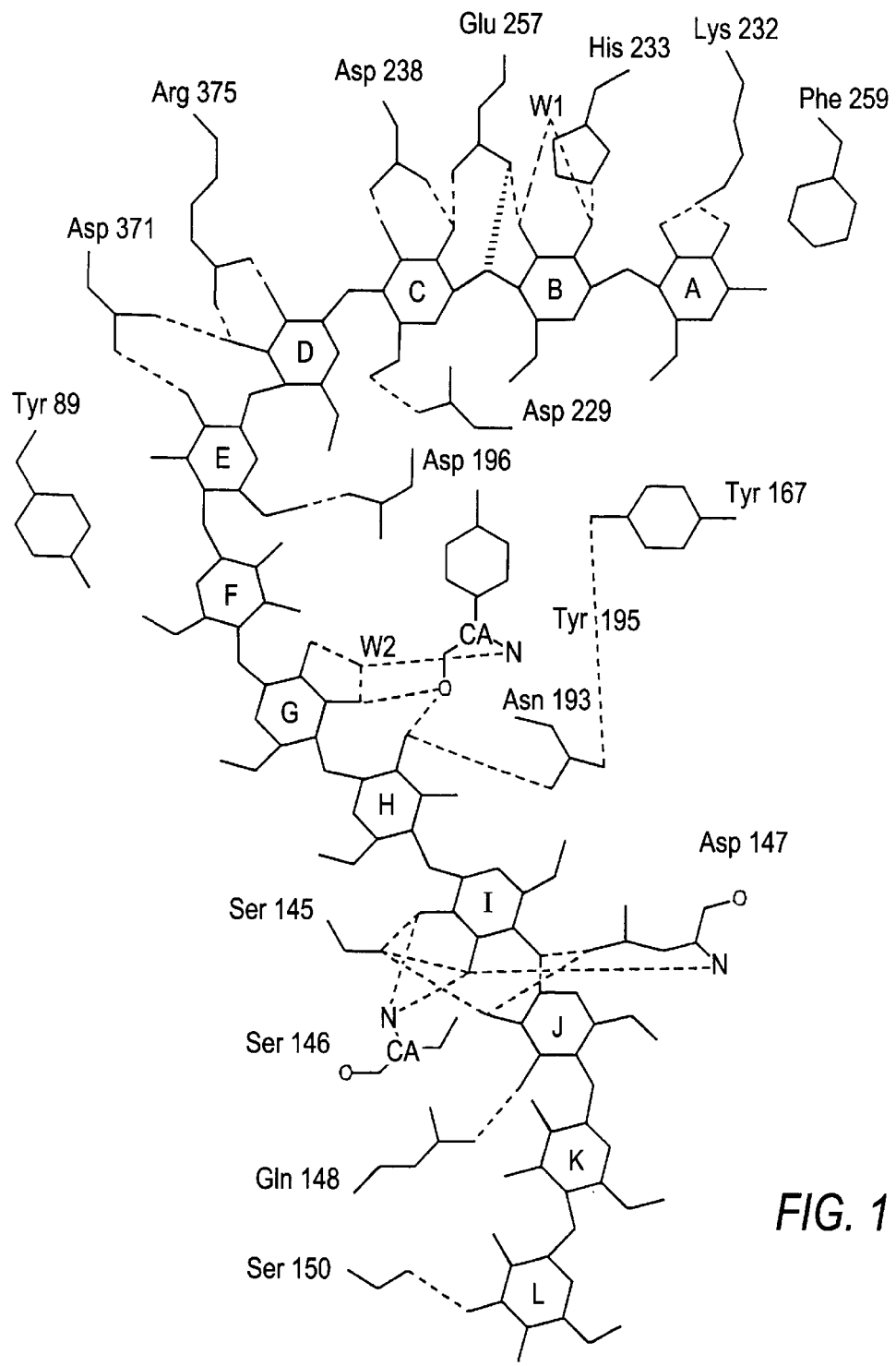
FIG. 1 shows a model of the structure of the active site cleft (domains A and B) of a CGTase from *Bacillus circulans* Strain 251, which has been complexed with a linear starch molecule, and residues involved in the enzyme-substrate interactions.

In a preferred embodiment of the invention, the introduction of more intermolecular interactions (e.g. more hydrogen bonding potential) in the region around glucose units C to I, preferably C to H, of FIG. 1, will lock the substrate in a position 6 glucose units from the catalytic site (between glucose units B and C of FIG. 1), and lead to increased product selectivity for α-cyclodextrins (6 glucose units). Moreover, the formation of larger cyclodextrins and/or larger linear oligosaccharides may simultaneously be reduced by reducing potential intermolecular interactions of glucose unit I to J of FIG. 1.

In another preferred embodiment of the invention, the introduction of more intermolecular interactions (e.g. more hydrogen bonding potential) in the region around glucose units F to J, preferably H and I, of FIG. 1, will lock the substrate in a position 7 glucose units from the catalytic site (between glucose units B and C of FIG. 1), and lead to increased product selectivity for β-cyclodextrins (7 glucose units). Moreover, the formation of e.g. α-cyclodextrins and/or small linear oligosaccharides may simultaneously be reduced by reducing potential intermolecular interactions of glucose unit C to G of FIG. 1.

In a third preferred embodiment of the invention, the introduction of more intermolecular interactions (e.g. more hydrogen bonding potential) in the region around glucose units H to K, preferably I and J, of FIG. 1, will lock the substrate in a position 8 glucose units from the catalytic site (between glucose units B and C of FIG. 1), and lead to increased product selectivity for γ-cyclodextrins (8 glucose units). Moreover, the formation of smaller cyclodextrins and/or linear oligosaccharides may simultaneously be reduced by reducing potential intermolecular interactions of glucose unit C to H of FIG. 1.

In a fourth preferred embodiment of the invention, the introduction of more intermolecular interactions (e.g. more hydrogen bonding potential) in the region around glucose units J to M, preferably K and L, of FIG. 1, will lock the substrate in a position 9 glucose units from the catalytic site (between glucose units B and C of FIG. 1), and lead to increased product selectivity for δ-cyclodextrins (9 glucose units).

Moreover, the formation of smaller cyclodextrins and/or linear oligosaccharides may simultaneously be reduced by reducing potential intermolecular interactions of glucose unit C to H of FIG. 1.

In a fifth preferred embodiment of the invention, the introduction of more intermolecular interactions (e.g. more hydrogen bonding potential) in the region around glucose units K to N, preferably L and M, of FIG. 1, will lock the substrate in a position 10 glucose units from the catalytic site (between glucose units B and C of FIG. 1), and lead to increased product selectivity for ε-cyclodextrins (10 glucose units). Moreover, the formation of smaller cyclodextrins and/or linear oligosaccharides may simultaneously be reduced by reducing potential intermolecular interactions of glucose unit C to H of FIG. 1.

In a sixth preferred embodiment of the invention, the introduction of more intermolecular interactions (e.g. more hydrogen bonding potential) in the region around glucose units L to O, preferably M and N, of FIG. 1, will lock the substrate in a position 11 glucose units from the catalytic site (between glucose units B and C of FIG. 1), and lead to increased product selectivity for ζ-cyclodextrins (11 glucose units). Moreover, the formation of smaller cyclodextrins and/or linear oligosaccharides may simultaneously be reduced by reducing potential intermolecular interactions of glucose unit C to H of FIG. 1.

In a seventh preferred embodiment of the invention, the formation of linear oligosaccharides of desired length may be increased by combining the above conditions with substitution at the cyclization axis, corresponding to position 195, CGTase numbering.

The CGTase enzyme subjected to the method of the invention may be any CGTase found in nature. However, the CGTase preferably is a microbial enzyme, preferably a bacterial enzyme, and preferably the CGTase is derived from a strain of Bacillus, a strain of Brevibacterium, a strain of Clostridium, a strain of Corynebacterium, a strain of Klebsiella, a strain of Micrococcus, a strain of Thermoanaerobium, a strain of Thermoanaerobacter, a strain of Thermoanaerobacterium, or a strain of Thermoactinomyces.

In more preferred embodiments, the CGTase is derived from a strain of *Bacillus autolyticus,* a strain of *Bacillus cereus,* a strain of *Bacillus circulans,* a strain of *Bacillus circulans var. alkalophilus,* a strain of *Bacillus coagulans,* a strain of *Bacillus firmus,* a strain of *Bacillus halophilus,* a strain of *Bacillus macerans,* a strain of *Bacillus megaterium,* a strain of *Bacillus ohbensis,* a strain of *Bacillus stearothermophilus,* a strain of *Bacillus subtilis,* a strain of *Klebsiella pneumonia,* a strain of *Thermoanaerobacter ethanolicus,* a strain of *Thermoanaerobacter finnii,* a strain of *Clostridium thermoamylolyticum,* a strain of *Clostridium thermosaccharolyticum,* or a strain of *Thermoanaerobacterium thermosulfurigenes.*

In most preferred embodiments, the CGTase is derived from the strain Bacillus sp. Strain 1011, the strain Bacillus sp. Strain 38-2, the strain Bacillus sp. Strain 17-1, the strain Bacillus sp. 1-1, the strain Bacillus sp. Strain B1018, the strain *Bacillus circulans* Strain 8, the strain Thermoanaerobacter sp. ATCC 53627, or the strain *Bacillus circulans* Strain 251, or a mutant or a variant thereof.

The strain Thermoanaerobacter sp. ATCC 53627 was deposited according to the Budapest Treaty on the International Recognition of the Deposit of Microorganisms for the Purposes of Patent Procedure at the American Type Culture Collection (ATCC), 12301 Parklawn Drive, Rockville, Md. 20852, USA, on Jun. 3, 1987. The strain *Bacillus circulans* Strain 251 has been deposited in the open collection at Rijksinstituut voor Volksgezondheid (RIV), Bilthoven, The Netherlands, and allotted the accession number RIV 11115, and thus is publicly available.

The method of the invention comprises substitution, insertion and/or deletion of one or more amino acid residue(s) of the enzyme, which residue(s) hold a position close to the substrate, when the substrate has bound to the CGTase enzyme at its substrate binding sites. In more specific aspects, the method of the invention comprises substitution, insertion and/or deletion of two or more amino acid residue(s), preferably of three or more amino acid residue(s).

In the context of this invention, a CGTase amino acid residue holding a position close to the substrate indicates an amino acid residue located within the enzyme in a way that it is within a potential intermolecular (i.e. enzyme-substrate) interactive distance from a glucose unit of the substrate (i.e. a polysaccharide). Examples of potential intermolecular interactions include, but are not limited to hydrogen bonding, salt bridge formation, polar interactions, hydrophobic interactions, and aromatic interactions.

In a preferred embodiment of this invention, an amino acid position close to the substrate indicates a distance less than 8 Å (angstrom), preferably less than 5 Å, more preferred less than 3 Å, from the substrate.

In a more preferred embodiment of this invention, these distances are calculated using the CGTase from *Bacillus circulans* Strain 251 [cf. Lawson C L, van Montfort R, Strokopytov B, Rozeboom H J, Kalk K H, de Vries G E, Penninga D, Dijkhuizen L, and Dijkstra B W; *J. Mol. Biol.* 1994 236 590–600], complexed with a derivative of maltonanose, the coordinates of which have been deposited with the Protein Data Bank, Biology Department, Bldg. 463, Brookhaven National Laboratory, P.O. Box 5000, Upton, N.Y. 11973-5000, USA, under the entry code 1DIJ. Knowledge of this structure makes it possible to identify similar positions in other CGTases, having a known primary structure, which positions corresponds to the positions stated in e.g. Table 2, cf. also Table 1.

CGTases have substrate binding regions located at the A domain, at the B domain, at the C domain and at the E domain of the enzyme. Consequently, in a preferred embodiment, the method of the invention comprises substituting one or more amino acid residue(s) of the CGTase enzyme, which residue(s) are located in one or more of the A, B, C and/or E domains, cf. Table 1.

By sequence alignment and molecular modelling of a CGTase enzyme found in nature, amino acid residues located close to the substrate can be identified. By using sequence alignment, the tertiary structure of any homologous CGTase can be modelled based on known three-dimensional CGTase structures.

Table 2, below, presents a list of CGTase amino acid positions located within 8 Å from the substrate, and therefore to be considered in the context of this invention. The amino acid residues are identified by CGTase numbering, which allows identification of the corresponding amino acid positions in any CGTase enzyme.

Preferably, the method of the invention comprises substitution, insertion and/or deletion at one or more amino acid residue(s) identified in Table 2, below.

TABLE 2

CGTase Amino Acid Residues less than 8 Å from the Substrate
Positions Identified by CGTase Numbering

| | | | | | |
|---|---|---|---|---|---|
| 19 | 142 | 192 | 301 | 476 | 634 |
| 21 | 143 | 193 | 304 | 596 | 635 |
| 46 | 144 | 194 | 326 | 597 | 636 |
| 47 | 145 | 195 | 327 | 598 | 649 |
| 75 | 146 | 196 | 328 | 599 | 650 |
| 78 | 147 | 197 | 329 | 600 | 651 |
| 82 | 148 | 198 | 370 | 601 | 652 |
| 87 | 149 | 199 | 371 | 602 | 653 |
| 88 | 150 | 227 | 372 | 603 | 655 |
| 89 | 151 | 228 | 374 | 604 | 656 |
| 90 | 154 | 229 | 375 | 605 | 660 |
| 94 | 167 | 230 | 410 | 607 | 661 |
| 95 | 168 | 231 | 411 | 608 | 662 |
| 96 | 176 | 232 | 412 | 609 | 663 |
| 97 | 177 | 233 | 413 | 615 | 664 |
| 98 | 178 | 257 | 414 | 616 | 665 |
| 99 | 179 | 258 | 415 | 617 | 666 |
| 100 | 180 | 259 | 416 | 618 | 667 |
| 101 | 181 | 260 | 418 | 624 | 668 |
| 102 | 182 | 261 | 420 | 625 | 685 |
| 135 | 183 | 262 | 443 | 626 | 686 |
| 136 | 184 | 264 | 444 | 627 | |
| 137 | 185 | 266 | 445 | 628 | |
| 138 | 186 | 268 | 446 | 629 | |
| 139 | 187 | 281 | 447 | 631 | |
| 140 | 188 | 283 | 448 | 632 | |
| 141 | 189 | 287 | 449 | 633 | |

By molecular modelling of the CGTase obtained from *Bacillus circulans* Strain 251, the amino acid positions presented in Tables 3–5, below, have been identified as positions close to the substrate, i.e. at a distance of 8 Å, 5 Å and 3 Å, respectively.

In a more preferred embodiment, the method of the invention comprises substitution, insertion and/or deletion at one or more amino acid residue(s) identified in Tables 3–5, below.

TABLE 3

CGTase Amino Acid Residues less than 8 Å from the Substrate
Positions Identified in *B. circulans* Strain 251 (CGTase Numbering)

| | | | | | |
|---|---|---|---|---|---|
| Gln-19 | Ser-142 | Gly-189 | Phe-0283 | Leu-447 | Val-629 |
| Phe-21 | Pro-143 | Lys-192 | Gln-287 | Val-448 | Tyr-631 |
| Arg-47 | Ala-144 | Asn-193 | Tyr-301 | Thr-449 | Gln-632 |
| Trp-75 | Ser-145 | Leu-194 | Lys-304 | Ala-476 | Tyr-633 |
| Gln-78 | Ser-146 | Phe-195 | Asn-326 | Ala-596 | Pro-634 |
| Asn-82 | Asp-147 | Asp-196 | His-327 | Thr-597 | Asn-635 |
| Ile-87 | Gln-148 | Leu-197 | Asp-328 | Thr-598 | Trp-636 |
| Asn-88 | Pro-149 | Ala-198 | Met-329 | Ala-599 | Glu-649 |
| Tyr-89 | Ser-150 | Asp-199 | Thr-370 | Leu-600 | Phe-650 |
| Ser-90 | Phe-151 | Arg-227 | Asp-371 | Gly-601 | Lys-651 |
| Asn-94 | Asn-154 | Met-228 | Pro-372 | Gln-602 | Phe-652 |
| Thr-95 | Tyr-167 | Asp-229 | Asn-374 | Asn-603 | Lys-655 |
| Ala-96 | Thr-168 | Ala-230 | Arg-375 | Val-604 | Gln-656 |
| Tyr-97 | His-176 | Val-231 | Gln-410 | Tyr-605 | Val-660 |
| His-98 | His-177 | Lys-232 | Glu-411 | Thr-607 | Thr-661 |

TABLE 3-continued

CGTase Amino Acid Residues less than 8 Å from the Substrate
Positions Identified in *B. circulans* Strain 251 (CGTase Numbering)

| | | | | | |
|---|---|---|---|---|---|
| Gly-99 | Asn-178 | His-233 | Arg-412 | Gly-608 | Trp-662 |
| Tyr-100 | Gly-179 | Glu-257 | Trp-413 | Ser-609 | Glu-663 |
| Trp-101 | Gly-180 | Trp-258 | Ile-414 | Asn-615 | Gly-664 |
| Ala-102 | Thr-181 | Phe-259 | Asn-415 | Trp-616 | Gly-665 |
| Asp-135 | Asp-182 | Leu-260 | Asn-416 | Asp-617 | Ser-666 |
| Phe-136 | Phe-183 | Gly-261 | Val-418 | Pro-618 | Asn-667 |
| Ala-137 | Ser-184 | Val-262 | Ile-420 | Pro-624 | His-668 |
| Pro-138 | Thr-185 | Glu-264 | Ser-443 | Met-625 | Gln-685 |
| Asn-139 | Thr-186 | Ser-266 | Ile-444 | Tyr-626 | Pro-686 |
| His-140 | Glu-187 | Glu-268 | Ser-445 | Asn-627 | |
| Thr-141 | Asn-188 | Leu-281 | Gly-446 | Gln-628 | |

TABLE 4

CGTase Amino Acid Residues less than 5 Å from the Substrate
Positions Identified in *B circulans* Strain 251 (CGTase Numbering)

| | | | | | |
|---|---|---|---|---|---|
| Tyr-89 | Pro-149 | Asn-193 | Leu-260 | Asn-415 | Tyr-626 |
| His-98 | Ser-150 | Leu-194 | Gly-261 | Gly-446 | Asn-627 |
| Tyr-100 | Tyr-167 | Phe-195 | Glu-264 | Leu-447 | Gln-628 |
| Trp-101 | Gly-179 | Asp-196 | Tyr-301 | Val-448 | Tyr-633 |
| Ala-137 | Gly-180 | Leu-197 | His-327 | Thr-598 | Trp-636 |
| His-140 | Thr-181 | Arg-227 | Asp-328 | Ala-599 | Glu-649 |
| Pro-143 | Asp-182 | Asp-229 | Asp-371 | Leu-600 | Lys-651 |
| Ala-144 | Phe-183 | Ala-230 | Arg-375 | Gly-601 | Trp-662 |
| Ser-145 | Ser-184 | Lys-232 | Glu-411 | Gln-602 | Glu-663 |
| Ser-146 | Thr-185 | His-233 | Arg-412 | Asn-603 | Asn-667 |
| Asp-147 | Glu-187 | Glu-257 | Trp-413 | Trp-616 | |
| Gln-148 | Asn-188 | Phe-259 | Ile-414 | Met-625 | |

TABLE 5

CGTase Amino Acid Residues less than 3 Å from the Substrate
Positions Identified in *B. circulans* Strain 251 (CGTase Numbering)

| | | | | | |
|---|---|---|---|---|---|
| Tyr-89 | Asp-147 | Asn-193 | Phe-259 | Thr-598 | Gln-628 |
| His-98 | Gln-148 | Phe-195 | His-327 | Ala-599 | Tyr-633 |
| Tyr-100 | Gly-180 | Asp-196 | Asp-328 | Leu-600 | Trp-636 |
| Trp-101 | Asp-182 | Asp-229 | Asp-371 | Gly-601 | Lys-651 |
| His-140 | Phe-183 | Lys-232 | Glu-411 | Gln-602 | Asn-667 |
| Ser-145 | Ser-184 | His-233 | Ile-414 | Asn-603 | |
| Ser-146 | Thr-185 | Glu-257 | Gly-446 | Asn-627 | |

In a similar manner, molecular modelling of the CGTase obtained from the strain Thermoanaerobacter sp. ATCC 53627, has revealed the amino acid positions presented in Tables 6–8, below, as being positions close to the substrate, i.e. at a distance of 8 Å, 5 Å and 3 Å, respectively.

In another preferred embodiment, the method of the invention comprises substitution, insertion and/or deletion at one or more amino acid residue(s) identified in Tables 6–8, below.

TABLE 6

CGTase Amino Acid Residues less than 8 Å from the Substrate
Positions Identified in Thermoanaerobacter sp. (CGTase Numbering)

| | | | | | |
|---|---|---|---|---|---|
| Gln-19 | His-140 | Tyr-186 | Glu-264 | Tyr-443 | Met-625 |
| Val-21 | Thr-141 | Glu-187 | Asp-266 | Ile-444 | Phe-626 |
| Leu-46 | Ser-142 | Asp-188 | Asn-268 | Thr-445 | Asn-627 |
| Lys-47 | Pro-143 | Gly-189 | Leu-281 | Gly-446 | Gln-628 |
| Trp-75 | Ala-144 | Arg-192 | Phe-283 | Leu-447 | Gln-632 |
| Gln-78 | Ser-145 | Asn-193 | Gln-287 | Tyr-448 | Tyr-633 |
| Asn-82 | Glu-146 | Leu-194 | Tyr-301 | Ser-476 | Pro-634 |
| Leu-87 | Thr-147 | Phe-195 | Asn-326 | Ala-596 | Thr-635 |
| Pro-88 | Asp-148 | Asp-196 | His-327 | Thr-597 | Trp-636 |
| Asp-89 | Pro-149 | Leu-197 | Asp-328 | Thr-598 | Glu-649 |

TABLE 6-continued

CGTase Amino Acid Residues less than 8 Å from the Substrate
Positions Identified in Thermoanaerobacter sp. (CGTase Numbering)

| | | | | | |
|---|---|---|---|---|---|
| Phe-91a | Thr-150 | Ala-198 | Met-329 | Val-599 | Phe-650 |
| Ser-94 | Tyr-151 | Asp-199 | Gly-370 | Trp-600 | Lys-651 |
| Thr-95 | Asn-154 | Arg-227 | Asp-371 | Gly-601 | Phe-652 |
| Ser-96 | Tyr-167 | Met-228 | Pro-372 | Glu-602 | Ile-653 |
| Tyr-97 | Thr-168 | Asp-229 | Asn-374 | Asn-603 | Lys-655 |
| His-98 | His-176 | Ala-230 | Arg-375 | Val-604 | Asn-656 |
| Gly-99 | His-177 | Val-231 | Lys-410 | Tyr-605 | Thr-661 |
| Tyr-100 | Tyr-178 | Lys-232 | Gln-411 | Thr-607 | Trp-662 |
| Trp-101 | Gly-179 | His-233 | Arg-412 | Gly-608 | Glu-663 |
| Ala-102 | Gly-180 | Glu-257 | Trp-413 | Asn-609 | Gly-664 |
| Asp-135 | Thr-181 | Trp-258 | Ile-414 | Asn-615 | Gly-665 |
| Phe-136 | Asn-182 | Tyr-259 | Asn-415 | Trp-616 | Tyr-666 |
| Ala-137 | Phe-183 | Leu-260 | Asn-416 | Asp-617 | Asn-667 |
| Pro-138 | Ser-184 | Gly-261 | Val-418 | Thr-618 | His-668 |
| Asn-139 | Ser-185 | Thr-262 | Ile-420 | Pro-624 | Gln-685 |

TABLE 7

CGTase Amino Acid Residues less than 5 Å from the Substrate
Positions Identified in Thermoanaerobacter sp. (CGTase Numbering)

| | | | | | |
|---|---|---|---|---|---|
| Lys-47 | Lys-148 | Asn-193 | Gly-261 | Thr-445 | Gln-628 |
| Ser-94 | Pro-149 | Leu-194 | Glu-264 | Gly-446 | Tyr-633 |
| Tyr-97 | Thr-150 | Phe-195 | Asp-266 | Leu-447 | Trp-636 |
| His-98 | Tyr-151 | Asp-196 | Tyr-301 | Tyr-448 | Glu-649 |
| Tyr-100 | Tyr-167 | Leu-197 | His-327 | Thr-598 | Lys-651 |
| Trp-101 | Gly-179 | Arg-227 | Asp-328 | Val-599 | Trp-662 |
| Ala-137 | Gly-180 | Asp-229 | Asp-371 | Trp-600 | Glu-663 |
| His-140 | Thr-181 | Ala-230 | Arg-375 | Gly-601 | Gly-665 |
| Pro-143 | Asn-182 | Lys-232 | Gln-411 | Glu-602 | Asn-667 |
| Ala-144 | Phe-183 | His-233 | Arg-412 | Asn-603 | |
| Ser-145 | Ser-184 | Glu-257 | Trp-413 | Trp-616 | |
| Glu-146 | Ser-185 | Tyr-259 | Ile-414 | Met-625 | |
| Thr-147 | Tyr-186 | Leu-260 | Asn-415 | Asn-627 | |

TABLE 8

CGTase Amino Acid Residues less than 3 Å from the Substrate
Positions Identified in Thermoanaerobacter sp. (CGTase Numbering)

| | | | | | |
|---|---|---|---|---|---|
| His-98 | Thr-147 | Phe-195 | Asp-328 | Thr-598 | Asn-627 |
| Tyr-100 | Gly-180 | Asp-229 | Asp-371 | Val-599 | Tyr-633 |
| Trp-101 | Phe-183 | His-233 | Arg-375 | Trp-600 | Lys-651 |
| His-140 | Ser-184 | Glu-257 | Gln-411 | Gly-601 | Asn-667 |
| Ser-145 | Ser-185 | Tyr-259 | Ile-414 | Glu-602 | |
| Glu-146 | Asn-193 | His-327 | Gly-446 | Asn-603 | |

As described above, the substrate binding and product selectivity of a CGTase variant of the invention can be designed by removing existing and/or introducing potential intermolecular interactions between the CGTase variant and its substrate.

Examples of intermolecular interactions include, but are not limited to hydrogen bonding, salt bridge formation, polar interactions, hydrophobic interactions, and aromatic interactions.

Amino acid residues having side chains with hydrogen bonding potentials (i.e. having H-bonding capability) are generally the following:

Ser (S), Thr (T), Asn (N), Gln (Q), His (H), Asp (D), Tyr (Y), Glu (E), Lys (K), Arg (R), Trp (W), and Cys (C).

Correspondingly the following amino acids do not in general possess the potential ability to form side chain hydrogen bonds (i.e. no H-bonding capability):

Ala (A), Val (V), Leu (L), Ile (I), Phe (F), Gly (G), Met (M), and Pro (P).

Amino acid residues having side chains with salt bridge formation potentials are generally the following:

Asp (D), Glu (E), Lys (K), Arg (R), and His (H).

Amino acid residues having side chains with polar interaction potentials are generally the following:

Asp (D), Asn (N), Glu (E), Gln (Q), Lys (K), Arg (R), His (H), Tyr (Y), Trp (W), and Cys (C).

Amino acid residues having side chains with hydrophobic interaction potentials are generally the following:

Ala (A), Val (V), Leu (L), Ile (I), Phe (F), Met (M), Pro (P), and part of the Arg (R), Glu (E) and Gln (Q) side-chains.

Amino acid residues having side chains with aromatic interaction potentials are generally the following:

His (H), Phe (F), Tyr (Y) and Trp (W).

CGTase Variants

In its second aspect, the present invention provides novel CGTase variants, having an amino acid sequence not found in nature. Functionally, the CGTase variant of the invention is regarded a derivative of a precursor CGTase enzyme (i.e. the native, parental, or wild-type enzyme).

In a CGTase variant of the invention, the substrate binding and/or product selectivity has been modified, as compared to the precursor CGTase enzyme, by replacement, insertion and/or deletion of one or more amino acid residue(s) holding a position close to the substrate.

The CGTase variant of the invention may be derived from any CGTase enzyme found in nature. However, the CGTase variant of the invention preferably is derived from a microbial enzyme, preferably a bacterial enzyme, and preferably the CGTase variant is derived from a strain of Bacillus, a strain of Brevibacterium, a strain of Clostridium, a strain of Corynebacterium, a strain of Klebsiella, a strain of Micrococcus, a strain of Thermoanaerobium, a strain of Thermoanaerobacter, a strain of Thermoanaerobacterium, or a strain of Thermoactinomyces.

In more preferred embodiments, the CGTase variant of the invention is derived from a strain of *Bacillus autolyticus*, a strain of *Bacillus cereus*, a strain of *Bacillus circulans*, a strain of *Bacillus circulans var. alkalophilus*, a strain of *Bacillus coagulans*, a strain of *Bacillus firmus*, a strain of *Bacillus halophilus*, a strain of *Bacillus macerans*, a strain of *Bacillus megaterium*, a strain of *Bacillus ohbensis*, a strain of *Bacillus stearothermophilus*, a strain of *Bacillus subtilis*, a strain of *Klebsiella pneumonia*, a strain of *Thermoanaerobacter ethanolicus*, a strain of *Thermoanaerobacter finnii*, a strain of *Clostridium thermoamylolyticum*, a strain of *Clostridium thermosaccharolyticum*, or a strain of *Thermoanaerobacterium thermosulfurigenes*.

In most preferred embodiments, the CGTase variant of the invention is derived from the strain Bacillus sp. Strain 1011, the strain Bacillus sp. Strain 38-2, the strain Bacillus sp. Strain 17-1, the strain Bacillus sp. 1-1, the strain Bacillus sp. Strain B1018, the strain *Bacillus circulans* Strain 8, the strain *Bacillus circulans* Strain 251, or the strain Thermoanaerobacter sp. ATCC 53627, or a mutant or a variant thereof.

In the context of this invention, an amino acid residue holding a position close to the substrate indicates an amino acid residue located within the enzyme in such a way that it is within a potential intermolecular (i.e. enzyme-substrate) interactive distance from a glucose unit of the substrate (i.e. a polysaccharide).

Examples of potential intermolecular interactions include, but are not limited to hydrogen bonding, salt bridge formation, polar interactions, hydrophobic interactions, and aromatic interactions.

In a preferred embodiment of this invention, an amino acid position close to the substrate indicates a distance less than 8 Å (angstrom), preferably less than 5 Å, more preferred less than 3 Å, from the substrate.

Moreover, CGTases have substrate binding regions located at the A domain, at the B domain, at the C domain and at the E domain. Consequently, in a preferred embodiment, the invention provides a CGTase variant, in which variant a substitution, an insertion and/or a deletion have been introduced at one or more of the amino acid residue(s) located in one or more of the A, B, C and E domains.

In another preferred embodiment, the invention provides a CGTase variant, in which variant a substitution, an insertion and/or a deletion have been introduced at one or more of the amino acid positions corresponding to the positions stated in Table 2.

However, if a substitutions at positions 195 and 198 (CGTase numbering) have been accomplished, the CGTase is not contemplated a CGTase variant of the invention unless additional substitution, insertion and/or deletion at one or more amino acid residue(s) has been introduced. Moreover, a CGTase comprising any of the following specific mutations: H140R, H140N, F183L, H233R, H233N, W258V, F259L, F259I, F259Y, F283L, H327R, H327N, T598F and/ or W636F, is not contemplated a CGTase variant of the invention, unless additional substitution, insertion and/or deletion of amino acid residue(s) at one or more positions not stated here has been introduced. Finally, a CGTase comprising any of the following specific mutations: F195Y/ F259Y, W258F/F259I, T598F/W636F, and F183L/F259L, is not contemplated a CGTase variant of the invention, unless additional substitution, insertion and/or deletion of amino acid residue(s) at one or more positions has been introduced. Therefore such CGTase variants are disclaimed according to the present invention.

In a more preferred embodiment, the CGTase variant of the invention is a CGTase variant derived from an enzyme obtainable from a strain of Bacillus, which enzyme has been modified by substitution, insertion and/or deletion at one or more amino acid positions corresponding to the positions stated in Tables 3–5. Preferably the CGTase variant is derived from a strain of *Bacillus autolyticus*, a strain of *Bacillus cereus*, a strain of *Bacillus circulans,* a strain of *Bacillus circulans var. alkalophilus,* a strain of *Bacillus coagulans*, a strain of *Bacillus firmus*, a strain of *Bacillus halophilus*, a strain of *Bacillus macerans*, a strain of *Bacillus megaterium,* a strain of *Bacillus ohbensis*, a strain of *Bacillus stearothermophilus,* or a strain of *Bacillus subtilis.* Most preferred, the CGTase variant is derived from the strain Bacillus sp. Strain 1011, the strain Bacillus sp. Strain 38-2, the strain Bacillus sp. Strain 17-1, the strain Bacillus sp. 1-1, the strain Bacillus sp. Strain B1018, the strain *Bacillus circulans* Strain 8, or the strain *Bacillus circulans* Strain 251, or a mutant or a variant thereof.

In another preferred embodiment, the CGTase variant of the invention is a CGTase variant derived from an enzyme obtainable from a strain of Thermoanaerobacter, which enzyme has been modified by substitution, insertion and/or deletion at one or more of the amino acid positions corresponding to the positions stated in Tables 6–8. Preferably the CGTase variant is derived from the strain Thermoanaerobacter sp. ATCC 53627, or a mutant or a variant thereof.

In a CGTase variant of the invention, the intermolecular enzyme/substrate interactions have been modified, as compared to the precursor enzyme. Examples of potential intermolecular interactions include, but are not limited to hydrogen bonding, salt bridge formation, polar interactions, hydrophobic interactions, and aromatic interactions. Such modifications may be accomplished by substitution, insertion and/or deletion at one or more of the above described positions, according to the following guidance.

Amino acid residues having side chains with hydrogen bonding potentials (i.e. having H-bonding capability) are generally the following:

Ser (S), Thr (T), Asn (N), Gln (Q), His (H), Asp (D), Tyr (Y), Glu (E), Lys (K), Arg (R), Trp (W), and Cys (C).

Correspondingly the following amino acids do not in general possess the potential ability to form side chain hydrogen bonds (i.e. no H-bonding capability):

Ala (A), Val (V), Leu (L), Ile (I), Phe (F), Gly (G), Met (M), and Pro (P).

Amino acid residues having side chains with salt bridge formation potentials are generally the following:

Asp (D), Glu (E), Lys (K), Arg (R), and His (H).

Amino acid residues having side chains with polar interaction potentials are generally the following:

Asp (D), Asn (N), Glu (E), Gln (Q), Lys (K), Arg (R), His (H), Tyr (Y), Trp (W), and Cys (C).

Amino acid residues having side chains with hydrophobic interaction potentials are generally the following:

Ala (A), Val (V), Leu (L), Ile (I), Phe (F), Met (M), Pro (P), and part of the Arg (R), Glu (E) and Gln (Q) side-chains.

Amino acid residues having side chains with aromatic interaction potentials are generally the following:

His (H), Phe (F), Tyr (Y) and Trp (W).

By the method of the invention variants are obtained, which possess an altered number of hydrogen bonds or other interactions in the subsites of the active cleft or in the groove leading to this cleft or on the maltose binding sites.

By altering subsites in the binding cleft it is possible to manipulate the number of sugars which are able to bind and thus alter the ratios of α-, β-, γ-cyclodextrins, etc., produced by the enzyme.

In particular, when construction of α-cyclodextrin forming CGTase variants is contemplated, interactions on or before subsites C-I of the substrate (cf. FIG. 1) should be increased, and interactions on subsites I and higher should be decreased. Alternatively sterical hindrance could be applied to prevent binding on subsites I and higher. For instance, starting from an Bacillus CGTase, the following mutations are contemplated, separately or in combinations.

Less coupling and disproportionating activity is achieved by removing interactions between the enzyme and the donor/acceptor, i.e. between the CGTase and subsites A, B, C and D. Mutations which remove hydrogen bonds are e.g.:

H233Q, D135L, R47L or R47Q.

Mutations which increase hydrogen bonding relative to the substrate are e.g.:

H233Q (relative to subsite B of the substrate), L197D or L197E (subsite D), N94Q or N94K or N94R or N94W or N94F (subsite E), D371N or D371G (subsite E+F), Y89D (subsite E), A144K or A144R or A144D (subsite H), N193D or N193E (subsite H), Y167F (in order to release the residue at position 193 for H-bonding to subsite H), and T185R or T185E or T185D (on maltose binding site 2, cf. below).

Mutations which alter the conformation of the substrate binding cleft, and thus make new enzyme-substrate interactions are e.g.:

N88P and P143G.

Mutations which decrease hydrogen bonding relative to the substrate are e.g.:

S145E or S145A, and S146P or S146Q or S146G (relative to subsite I of the substrate).

A mutation which increases the hydrogen bonding relative to subsite H is e.g. A144R.

A mutation which increases hydrogen bonding relative to the substrate is e.g. N88K.

Mutations which leads to sterical hindrance are e.g.:

S145W or S145Y or S145F, and S146W or S146I or S146R or S146P (prevent binding on subsite I of the substrate).

Mutations which increase electrostatic interactions (stacking) are e.g.:

L600W or L600F or L600Y (of maltose binding site 2, cf. below).

In a preferred embodiment, an α-cyclodextrin forming CGTase variant of the invention may be a variant, which at positions 87–94 comprises the partial amino acid sequence IKYSGVNN (SEQ ID NO:11), and/or at positions 143–151 comprises the partial amino acid sequence GRAGTNPGF (SEQ ID NO:12), or at positions 143–145 comprises the partial amino acid sequence GRW.

In order to produce an enzyme with an improved product selectivity towards β-cyclodextrins it is necessary to circumvent the production of both smaller and larger cyclic products. A rationale might be to prevent the production of α-cyclodextrin by removing hydrogen bonds between the enzyme and substrate, which enable the substrate to move more quickly into the active site. Conversely, introduction of hydrogen bonds at relevant positions slow down the movement of substrate leading to the production of larger cyclodextrins. This approach, coupled with the substitution of amino acid residues which cause sterical hindrance for smaller amino acid residues at positions designed to block the movement of substrate, prevent the formation of cyclodextrins larger than β-cyclodextrin. Therefore, if construction of β-cyclodextrin forming CGTase variants is contemplated, the following mutations are contemplated, separately or in combinations, also starting from an Bacillus CGTase.

Mutations which alter the conformation of the substrate binding cleft close to the active site and thus create space for larger cyclodextrins (β- and γ-cyclodextrins) are e.g.:

N88P, Y89* (a deletion), 91aY (an insertion), V92* or N92*, and N94*.

A mutation which increases hydrogen bonding relative to the substrate is e.g. S146E.

Mutations which decrease hydrogen bonding relative to the substrate are e.g.

S145L, and Q148N.

Mutations which remove hydrogen bonds from subsites D, E, F, H, I and J of the substrate are e.g.:

R375G, D371G, D371N, Y89G, N193G, S145A, Q148A, and *145aI.

A mutation which introduce sterical hindrance between subsites I and J of the substrate, designed to shift the product ratio towards the production of smaller cyclodextrins is e.g. D147W.

In a preferred embodiment, a β-cyclodextrin forming CGTase variant of the invention may be a variant, which at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAETWPAF (SEQ ID NO:5).

In another preferred embodiment, a β-cyclodextrin forming CGTase variant of the invention may be a variant, which at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAETWPAF (SEQ ID NO:5), and which variant at position 195 holds a leucine residue (X195L).

In a third preferred embodiment, a CGTase variant of the invention capable of forming linear oligosaccharides may be a variant, which at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAETWPAF (SEQ ID NO:5), and which variant at position 195 holds a glycine residue (X195G).

Similarly, if construction of γ-cyclodextrin forming CGTase variants is contemplated, the following mutations are contemplated, separately or in combinations, again starting from an Bacillus CGTase.

Mutations which alter the conformation of the substrate binding cleft close to the active site and thus create space for larger cyclodextrins (β- and γ-cyclodextrins) are e.g.:

N88P, Y89* (a deletion), 91aY (an insertion), V92* or N92*, and N94*.

A mutation which increases hydrogen bonding relative to the substrate is e.g. S146E.

Mutations which decrease hydrogen bonding relative to the substrate are e.g.

S145L, and Q148N.

Mutations which remove hydrogen bonds from subsites D, E, F and H of the substrate are e.g.:

N193G, R375G, D371G, and D371N.

A mutation which remove hydrogen bonds and hydrophobic stacking from subsites D, E, F and H of the substrate e.g. Y89G.

Mutations which change the binding properties at subsites I and J of the substrate are e.g.:

X145aI or *145aI (via insertion), S145A, and Q148E, in particular S145A/X145aI or A145A/*145aI, and X145aI/Q148E or *145aI/Q148E.

Mutations which reduce the coupling activity at subsites A, D and E are e.g.:

R375G, D371G, K232Q, and E264Q.

Mutations reducing the coupling activity by changing specific binding of cyclodextrins is e.g. R47Q.

In particular, when considering CGTase variants derived from a strain of Thermoanaerobacter, mutations which lead to less hydrolysis, obtained by removing water molecules close to the active site, are e.g.:

V21F or V21Y.

Less coupling and disproportionating activity is achieved by removing interactions between the enzyme and the donor/acceptor, i.e. between the CGTase and subsites A, B, C and D. Mutations which remove hydrogen bonds are e.g.:

Y259F, H233Q, and D135L.

In a preferred embodiment, a γ-cyclodextrin forming CGTase variant of the invention may be a variant, which at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAEADPNF (SEQ ID NO:6).

In another preferred embodiment, a γ-cyclodextrin forming CGTase variant of the invention may be a variant, which at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAEADPNF (SEQ ID NO:6), and which variant at position 195 holds a leucine residue (X195W).

In a third preferred embodiment, in order to obtain linear oligosaccharides of a desired length, the variants of the invention may be combined with a substitution at the central amino acid residue forming the cyclization axis, corresponding to position 195, CGTase numbering. At this position, tyrosine and phenylalanine are predominant in wild-type CGTases (cf. Table 1). By changing this residue, the cyclization properties are affected, and cyclization may be prohibited. In a preferred embodiment, glycine is introduced at this position (X195G).

In yet another preferred embodiment, a CGTase variant of the invention is an enzyme which has been modified by substitution, insertion and/or deletion at one or more of the amino acid positions corresponding to the positions stated in Table 9, below. As indicated in this table, the introduction of one or more of these substitutions/insertions/deletions lead to CGTase variants of increased product selectivity in respect of α-, β- or γ-cyclodextrins, respectively.

have been found on each enzyme molecule on contact points between these molecules (maltose binding sites, MBS). Two of these maltoses are bound to specific sites on the E domain (MBS1 and MBS2, near 616 and 662), the third site is located on the C domain (MBS3, near 413). Thus, the binding sites on the E domain are required for the conversion of raw starch into cyclodextrins. Experiments, as conducted below, indicate that the enzyme binds to the raw starch granule via MBS1, while MBS2 guides a starch chain protruding from the granule to the active site.

In another preferred embodiment, a CGTase variant of the invention is an enzyme which has been modified by substitution, insertion and/or deletion at one or more of the amino acid positions corresponding to the positions stated in

TABLE 9

CGTase Variants of Increased Product Selectivity
Positions Identified by CGTase Numbering

| Position | α-cyclodextrin | β-cyclodextrin | γ-cyclodextrin |
| --- | --- | --- | --- |
| 21 | F,Y | F,Y | F,Y |
| 47 | Q,L | A,Q,H,R,L | A,Q,H,R,L |
| 87 | I,H | I,H | I,H |
| 88 | P,N,K,H | P,N,K,H | P,N,K,H |
| 89 | D,G,A,Y,E,* | D,G,A,E,K,R,Y,P,* | D,G,A,Y,P,* |
| 90 | S | G,A,S | G,A,S |
| 91 | A,V,D,G,T | A,V,G,S,T | A,V,G,S |
| 91a | A,V,G,Y,* | A,V,G,Y,F,* | A,V,G,Y,F,* |
| 92 | G,V,* | G,V,* | G,V,* |
| 93 | G,N,* | G,N,H,T,* | G,N,H,T,* |
| 94 | Q,K,R,W,F,N,S,* | Q,K,R,W, F, N,S,* | Q,K,R,W,F,N,S,* |
| 98 | H | G,A | G,A |
| 101 | W | G,A | G,A,F,Y |
| 135 | L,D | L,D | L,D |
| 140 | A,R,N | A,R,N | A,R,N |
| 143 | G,S,A | P | P |
| 144 | K,R,D,A,N,E,Q | A | A |
| 145 | A,E,W,P,G,F,Y,P,R,K | A,E,L,W | A,E,L,W |
| 145a | P,A,F,Q,S,W,I,R,* | P,A,I,Q,S | I,A,Q,P,S |
| 146 | P,A,F,Q,S,W,I,R,G,E,* | P,A,I,Q,S,E,K,D,N,R,F,W,* | I,A,Q,P,S,E |
| 147 | A,L,I,F,T,* | A,L,I,F,W,G,Y,R,D,T,* | S,T,A,D |
| 147a | * | * | D,N,E,Q,T |
| 148 | G,A,N | G,A,N,Q | D,E,R,K,Y,F,N,Q |
| 149 | P | W,P | L,I,F,W,P |
| 150 | A,G | A,S | A,S,N |
| 167 | P,F,Y | A,F,Y | A,F,P,Y |
| 168 | S,T | S,T | S,T |
| 178 | N,Y | N,Y | N,Y |
| 179 | S,N,D | G,S,N,D | G,S,N,D |
| 180 | S,N,D | G,S,N,D | G,S,N,D |
| 183 | F,W,Y,A | F,W,Y,A | F,W,Y,A |
| 185 | P,H,R,E,D | P,H,R,E,D | P,H,R,E,D |
| 192 | K,R | K,R | K,R |
| 193 | G,D,E,N,Q | G,A,N | G,A,N |
| 195 | Y,F | L,I,W,Y,F | L,I,W,F,Y |
| 196 | A,D,N,S | A,D,N,S | A,D,N,S |
| 197 | D,E,L | D,E,L | D,E,L |
| 232 | K,Q,L | K,Q,L | K,Q,L |
| 233 | H,Q,N,I | H,Q,N,I | H,Q,N,I |
| 259 | F,W,Y,A | F,W,Y,A | F,W,Y,A |
| 264 | Q | Q | Q |
| 326 | Q,F,L | Q,F,L | Q,F,L |
| 370 | G | T,N | T,N |
| 371 | A,D,S,N,G,E,Q | A,G,N,D,S | A,G,N,V,L,I,D,S |
| 373 | D,N,Y | D,E,Y | D,E,Y |
| 375 | R,K | A,P,G,R,K | A,P,G,R,K |
| 600 | X | X | X |

X = any natural amino acid residue
*deleted or absent residue

In respect to product binding and product inhibition, the E domain of the *Bacillus circulans* Strain 251 CGTase has now been identified as a raw starch binding domain. In the maltose dependent crystal structure, three maltose molecules Table 10, below. Such modifications lead to CGTase variants of reduced product inhibition.

For instance, in the context of this invention, the following mutations, starting from an Bacillus CGTase, are contemplated, separately or in combination, in order to reduce product inhibition.

Mutations which reduces non-competitive product inhibition are e.g.:

Y633A (takes place on MBS2, this mutation completely removes non-competitive product inhibition), 599aP or 599aR or 599aH, and L600R.

Residues 595–605 form a loop next to MBS2. Insertion enlarges the loop, thereby preventing binding of a cyclodextrin to MBS2 by sterical hindrance, while the role of MBS2 in guidance of the substrate chain is preserved. Mutations at position 600 and adjacent residues could reduce the binding of cyclic products to MBS2, while the binding of linear substrates remains unaffected. Substitution of leucine at position 600 with aspartate, alanine or glycine has minor effects on product inhibition. Substitution with arginine, due to its large size and charged nature, affect binding of cyclodextrins, thereby reducing product inhibition.

Mutations that decrease electrostatic interactions around MBS1, leading to decreased product affinity are e.g. W616A and/or W662A.

Mutations that decrease electrostatic interactions around MBS2, leading to decreased product affinity are e.g. L600A or L600S, and/or Y663A.

A mutations that decreases electrostatic interactions around MBS3, leading to decreased product affinity is e.g. W413A.

Competitive product inhibition is contemplated caused by coupling reactions. Reduction of this coupling reaction may be achieved by reducing the binding of the first (cyclodextrin) and second (malto-oligosaccharide) substrate.

Mutations reducing competitive product inhibition by reducing cyclodextrin binding are e.g.:

R47A or R47Q or R47L, Y89G, D196A or D196L, D371G or D371N or D371A or D371L, and R375G or R375Q or R375N or R375A or R375L.

Mutations reducing competitive product inhibition by reducing binding of the second substrate are e.g.:

K232Q or K232N or K232A or K232L, E264A or E264N or E264L, T186A, and E268A.

TABLE 10

CGTase Variants of Reduced Product Inhibition
Positions Identified by CGTase Numbering

| | |
|---|---|
| 47 | A,Q,L |
| 89 | G |
| 100 | A,I,L,F,Y |
| 185 | R,E,D |

TABLE 10-continued

CGTase Variants of Reduced Product Inhibition
Positions Identified by CGTase Numbering

| | |
|---|---|
| 186 | A |
| 196 | A,L,D |
| 232 | K,Q,N,A,L |
| 264 | A,N,L |
| 268 | A |
| 339 | A |
| 371 | G,N,A,L,D,S,E,Q |
| 375 | G,Q,N,A,L,R,K |
| 382 | A,L,V |
| 384 | A,L,V |
| 413 | A,V,G,W |
| 598 | A,V,G,P,T |
| 599a | P,R,H |
| 600 | X |
| 603 | A,V,L,G,N |
| 616 | A,I,L,G,W |
| 626 | A,I,V,L,G |
| 627 | A,V,L,G,N |
| 628 | A,V,L,G,Q |
| 633 | A,V,L,I,G,Y |
| 636 | I,L,A,G,W |
| 649 | A,G |
| 651 | A,G,V,K |
| 662 | A,L,I,G,W |
| 667 | A,N |

X = any natural amino acid residue

In a preferred embodiment, the CGTase variant of the invention is a CGTase variant derived from an enzyme obtainable from a strain of Bacillus, which enzyme has been modified by substitution, insertion and/or deletion at one or more of the amino acid positions corresponding to the positions stated in Table 11, below. Such modifications lead to CGTase variants of increased product selectivity, as indicated in the table.

More preferred, the CGTase variant is derived from a strain of a strain of *Bacillus autolyticus,* a strain of *Bacillus cereus,* a strain of *Bacillus circulans,* a strain of *Bacillus circulans var. alkalophilus,* a strain of *Bacillus coagulans,* a strain of *Bacillus firmus,* a strain of *Bacillus halophilus,* a strain of *Bacillus macerans,* a strain of *Bacillus megaterium,* a strain of *Bacillus ohbensis,* a strain of *Bacillus stearothermophilus,* or a strain of *Bacillus subtilis.*

Most preferred, the CGTase variant is derived from the strain Bacillus sp. Strain 1011, the strain Bacillus sp. Strain 38-2, the strain Bacillus sp. Strain 17-1, the strain Bacillus sp. 1-1, the strain Bacillus sp. Strain B1018, the strain *Bacillus circulans* Strain 8, or the strain *Bacillus circulans* Strain 251, or a mutant or a variant thereof.

TABLE 11

Bacillus Derived CGTase Variants of Increased Product Selectivity
Positions Identified by CGTase Numbering

| Position | α-cyclodextrin | β-cyclodextrin | γ-cyclodextrin |
|---|---|---|---|
| 21 | F,Y | F,Y | F,Y |
| 47 | Q,L | A,Q,H,R,L | A,Q,H,R,L |
| 87 | H | H | H |
| 88 | P,N,K,H | P,N,K,H | P,N,K,H |
| 89 | D,G,A,E,* | D,G,A,E,K,R,P,* | D,G,A,P,* |
| 90 | — | G,A | G,A |
| 91 | A,V,D,T | A,V,S,T | A,V,S |
| 91a | A,V,G,Y,* | A,V,G,Y,F,* | A,V,G,Y,F,* |

TABLE 11-continued

Bacillus Derived CGTase Variants of Increased Product Selectivity
Positions Identified by CGTase Numbering

| Position | α-cyclodextrin | β-cyclodextrin | γ-cyclodextrin |
|---|---|---|---|
| 92 | G,* | G,* | G,* |
| 93 | G,* | G,H,T,* | G,H,T,* |
| 94 | Q,K,R,W,F,S,* | Q,K,R,W,F,S,* | Q,K,R,W,F,S,* |
| 98 | — | G,A | G,A |
| 101 | — | G,A | G,A,F,Y |
| 135 | L | L | L |
| 140 | A,R,N | A,R,N | A,R,N |
| 143 | G,S | P | P |
| 144 | K,R,D,A,N,E,Q | A | A |
| 145 | A,E,W,P,G,F,Y,P,R,K | A,E,L,W | A,E,L,W |
| 145a | P,A,F,Q,S,W,I,R,* | P,A,I,Q,S | I,A,Q,P,S |
| 146 | P,A,F,Q,S,W,I,R,G,E,* | P,A,I,Q,S,E,K,D,N,R,F,W,* | I,A,Q,P,S,E |
| 147 | A,L,I,F,* | A,L,I,F,W,G,Y,R,D,T,* | S,T,A,D |
| 147a | * | * | D,N,E,Q,T |
| 148 | G,A,N | G,A,N | D,E,R,K,Y,F,N |
| 149 | — | W | L,I,F,W |
| 150 | A,G | A | A,S,N |
| 167 | P,F | A,F | A,F,P |
| 168 | S,T | S,T | S,T |
| 178 | N,Y | N,Y | N,Y |
| 179 | S,N,D | S,N,D | S,N,D |
| 180 | S,N,D | S,N,D | S,N,D |
| 183 | W,Y,A | W,Y,A | W,Y,A |
| 185 | P,H,R,E,D | P,H,R,E,D | P,H,R,E,D |
| 192 | K,R | K,R | K,R |
| 193 | G,D,E,Q | G,A | G,A |
| 195 | F | L,I,W,F | L,I,W,F |
| 196 | A,S,N,G | A,S,N,G | A,S,N,G |
| 197 | D,E | D,E | D,E |
| 232 | Q,L | Q,L | Q,L |
| 233 | Q,N,I | Q,N,I | Q,N,I |
| 259 | F,W,A | F,W,A | F,W,A |
| 264 | Q | Q | Q |
| 326 | Q,F,L | Q,F,L | Q,F,L |
| 370 | G | T,N | T,N |
| 371 | A,S,N,G,E,Q | A,G,N,S | A,G,N,V,L,I,S |
| 373 | D,N,Y | D,E,Y | D,E,Y |
| 375 | — | A,P,G,K | A,P,G,K |
| 600 | X | X | X |

X = any natural amino acid residue
— conserved residue
* deleted or absent residue In another preferred embodiment, the CGTase variant of the invention is a CGTase variant derived from an enzyme obtainable from a strain of Bacillus, which enzyme has been modified by substitution, insertion and/or deletion at one or more of the amino acid positions corresponding to the positions stated in Table 12, below. Such modifications lead to CGTase variants of reduced product inhibition.

TABLE 12

Bacillus Derived CGTase Variants of Reduced Product Inhibition
Positions Identified by CGTase Numbering

| 47 | A,Q,L |
| 89 | G |
| 100 | A,I,L,F |
| 185 | R,E,D |
| 186 | A |
| 196 | A,L |
| 232 | Q,N,A,L |
| 264 | A,N,L |
| 268 | A |
| 339 | A |
| 371 | G,N,A,L,S,E,Q |
| 375 | G,Q,N,A,L,K |
| 382 | A,L,V |

TABLE 12-continued

Bacillus Derived CGTase Variants of Reduced Product Inhibition
Positions Identified by CGTase Numbering

| 384 | A,L,V |
| 413 | A,V,G |
| 598 | A,V,G,P |
| 599a | P,R,H |
| 600 | X |
| 603 | A,V,L,G |
| 616 | A,I,L,G |
| 626 | A,I,V,L,G |
| 627 | A,V,L,G |
| 628 | A,V,L,G |
| 633 | A,V,L,I,G |
| 636 | I,L,A,G |
| 649 | A,G |
| 651 | A,G,V |
| 662 | A,L,I,G |
| 667 | A |

X = any natural amino acid residue

As its most preferred embodiments, the invention provides the following CGTase variants:

A CGTase variant, which variant at position 21 holds a tyrosine residue (F21Y).

A CGTase variant, which variant at position 47 holds a glutamine residue (R47Q), or an alanine residue (R47A), or a leucine residue (R47L), or a histidine residue (R47H).

A CGTase variant, which variant at position 88 holds a proline residue (N88P) or a lysine residue (N88K).

A CGTase variant, which variant at position 89 holds an aspartic acid residue (Y89D), or an alanine residue (Y89A), or a glycine residue (Y89G).

A CGTase variant, which variant at position 91a (via insertion) holds an alanine residue (*91aA), or a tyrosine residue (*91aY).

A CGTase variant, in which variant position 92 has been deleted (V92*).

A CGTase variant, which variant at position 94 holds a glutamine residue (N94Q), or a lysine residue (N94K), or an arginine residue (N94R), or a tryptophan residue (N94W), or a phenylalanine residue (N94F), or in which variant position 94 has been deleted (N94*).

A CGTase variant, which variant at position 135 holds a leucine residue (D135L).

A CGTase variant, which variant at position 143 holds a natural amino acid residue different from that of the wild-type enzyme (P143X).

A CGTase variant, which variant at position 143 holds an alanine residue (P143A), or a glycine residue (P143G).

A CGTase variant, which variant at position 144 holds a natural amino acid residue different from that of the wild-type enzyme (A144X).

A CGTase variant, which variant at position 144 holds an arginine residue (A144R), or a lysine residue (A144K), or an aspartic acid residue (A144D).

A CGTase variant, which variant at position 145 holds a natural amino acid residue different from that of the wild-type enzyme (S145X).

A CGTase variant, which variant at position 145 holds an alanine residue (S145A), or a glutamic acid (S145E), or a tryptophan residue (S145W), or a glycine residue (S145G), or a phenylalanine residue (S145F), or a tyrosine residue (S145Y), or a leucine residue (S145L).

A CGTase variant, which variant at position 145a (via insertion) holds a natural amino acid residue (*145aX).

A CGTase variant, which variant at position 145a (via insertion) holds an isoleucine residue (*145aI).

A CGTase variant, which variant at position 146 holds a natural amino acid residue different from that of the wild-type enzyme (S146X).

A CGTase variant, which variant at position 146 holds a proline residue (S146P), or an isoleucine residue (S146I), or a glutamine residue (S146Q), or a tryptophan residue (S146W), or an arginine residue (S146R), or a glutamic acid residue (S146E).

A CGTase variant, which variant at position 147 holds a natural amino acid residue different from that of the wild-type enzyme (D147X).

A CGTase variant, which variant at position 147 holds an isoleucine residue (D147I), or a leucine residue (D147L), or an alanine residue (D147A), or a serine residue (D147S), or a tryptophan residue (D147W).

A CGTase variant, which variant at position 147a (via insertion) holds an alanine residue (*147aA).

A CGTase variant, which variant at position 147a (via insertion) holds a natural amino acid residue (*147aX).

A CGTase variant, which variant at position 148 holds a natural amino acid residue different from that of the wild-type enzyme (Q148X).

A CGTase variant, which variant at position 148 holds an alanine residue (Q148A), or a glycine residue (Q148G), or a glutamic acid residue (Q148E), or an asparagine residue (Q148N).

A CGTase variant, which variant at position 149 holds a natural amino acid residue different from that of the wild-type enzyme (P149X).

A CGTase variant, which variant at position 149 holds an isoleucine residue (P149I).

A CGTase variant, which variant at position 167 holds a phenylalanine residue (Y167F).

A CGTase variant, which variant at position 179 holds a serine residue (G179S), an asparagine residue (G179N), or an aspartic acid residue (G179D).

A CGTase variant, which variant at position 180 holds a serine residue (G180S), an asparagine residue (G180N), or an aspartic acid residue (G180D).

A CGTase variant, which variant at position 185 holds an arginine residue (T185R), or a glutamic acid residue (T185E), or an aspartic acid residue (T185D).

A CGTase variant, which variant at position 186 holds an alanine residue (T186A).

A CGTase variant, which variant at position 193 holds a natural amino acid residue different from that of the wild-type enzyme (N193X).

A CGTase variant, which variant at position 193 holds a glycine residue (N193G), or an alanine residue (N193A), or an aspartic acid residue (N193D), or a glutamic acid residue (N193E).

A CGTase variant, which variant at position 195 holds a natural amino acid residue different from that of the wild-type enzyme (Y195X).

A CGTase variant, which variant at position 196 holds a natural amino acid residue different from that of the wild-type enzyme (D196X).

A CGTase variant, which variant at position 196 holds an alanine residue (D196A), a serine residue (D196S), or a leucine residue (D196L).

A CGTase variant, which variant at position 197 holds an aspartic acid residue (L197D), or a glutamic acid residue (L197E).

A CGTase variant, which variant at position 232 holds a glutamine residue (K232Q), or an asparagine residue (K232N), or an alanine residue (K232A), or a leucine residue (K232L).

A CGTase variant, which variant at position 233 holds a glutamine residue (H233Q).

A CGTase variant, which variant at position 264 holds a glutamine residue (E264Q), or an alanine residue (E264A), or an asparagine residue (E264N), or a leucine residue (E264L).

A CGTase variant, which variant at position 268 holds an alanine residue (E268A).

A CGTase variant, which variant at position 371 holds a natural amino acid residue different from that of the wild-type enzyme (D371X).

A CGTase variant, which variant at position 371 holds a glycine residue (D371G), or an asparagine residue (D371N), or an alanine residue (D371A), or a leucine residue (D371L).

A CGTase variant, which variant at position 375 holds a natural amino acid residue different from that of the wild-type enzyme (R375X).

A CGTase variant, which variant at position 375 holds a proline residue (R375P), or a glycine residue (R375G), or a glutamine residue (R375Q), or an asparagine residue (R375N), or an alanine residue (R375A), or a leucine residue (R375L).

A CGTase variant, which variant at position 599a (via insertion) holds a proline residue (*599aP), or an arginine residue (*599aR), or a histidine residue (*599aH).

A CGTase variant, which variant position 600 has been substituted for a different naturally occurring amino acid residue, in particular a tryptophan residue (L600W), a phenylalanine residue (L600F), a tyrosine residue (L600Y), an arginine residue (L600R), a proline residue (L600P), or an asparagine residue (L600N).

A CGTase variant, which variant at position 616 holds an alanine residue (W616A).

A CGTase variant, which variant at position 633 holds an alanine residue (Y633A).

A CGTase variant, which variant at position 662 holds an alanine residue (W662A).

A CGTase variant, which variant at position 47 holds a histidine residue, and at position 135 holds a leucine residue (R47H/D135L).

A CGTase variant, which variant at position 88 holds a proline residue, and at position 143 holds a glycine residue (N88P/P143G).

A CGTase variant, which variant at position 89 holds an aspartic acid residue, and at position 146 holds a proline residue (Y89D/S146P).

A CGTase variant, which variant at position 89 holds a glycine residue, and at position 193 holds a glycine residue (Y89G/N193G).

A CGTase variant, in which variant positions 92 and 94 have been deleted (V92*/N94*).

A CGTase variant, which variant at position 143 holds an alanine residue, and at position 144 holds an arginine residue (P143A/A144R).

A CGTase variant, which variant at position 143 holds a glycine residue, and at position 144 holds an arginine residue, and at position 145 holds a tryptophan residue (P143G/A144R/S145W).

A CGTase variant, which variant at position 143 holds a glycine residue, and at position 144 holds an arginine residue, and at position 145 holds a tryptophan residue (P143G/A144R/S145W), and which variant at position 179 holds a serine residue (G179S), an asparagine residue (G179N), or an aspartic acid residue (G179D).

A CGTase variant, which variant at positions 143–148 comprises the partial amino acid sequence GRA**A (SEQ ID NO:7), the partial amino acid sequence GRAAAA (SEQ ID NO:8), the partial amino acid sequence GRAPAA (SEQ ID NO:9), or the partial amino acid sequence GRGPAA (SEQ ID NO:10).

A CGTase variant, which variant at position 144 holds an arginine residue, at position 145 holds an alanine residue, and at position 146 holds a proline residue (A144R/S145A/S146P).

A CGTase variant, which variant at position 145 holds an alanine residue, and at position 145a (via insertion) holds an isoleucine residue (S145A/*145aI).

A CGTase variant, which variant at position 145 holds an alanine residue, and at position 146 holds a glycine residue (S145A/S146G).

A CGTase variant, which variant at position 145 holds a leucine residue, and at position 148 holds an asparagine residue (S145L/Q148N).

A CGTase variant, which variant at position 145 holds a glutamic acid residue, and in position 146 holds a proline residue or a glutamine residue (S145E/S146P or S145E/S146Q).

A CGTase variant, which variant at position 145 holds a tryptophan residue, and in position 146 holds a tryptophan residue, or an isoleucine residue, or an arginine residue (S145W/S146W or S145W/S146I or S145W/S146R).

A CGTase variant, which variant at position 145 holds an alanine residue, at position 145a (via insertion) holds an isoleucine residue, and at position 148 holds a glutamic acid residue (S145A/*145aI/Q148E).

A CGTase variant, which variant at position 145a (via insertion) holds an isoleucine residue, and at position 148 holds a glutamic acid residue (*145aI/Q148E).

A CGTase variant, which variant at position 148 holds a glutamic acid residue, and at position 193 holds a glutamine residue.

A CGTase variant, which variant at position 616 holds an alanine residue, and at position 662 holds an alanine residue (W616A/W662A).

A CGTase variant, which variant at positions 87–94 comprises the partial amino acid sequence IKYSGVNN (SEQ ID NO:11), and/or at positions 143–151 comprises the partial amino acid sequence GRAGTNPGF (SEQ ID NO:12), or at positions 143–145 comprises the partial amino acid sequence GRW.

A CGTase variant, which variant at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAETWPAF (SEQ ID NO:5).

A CGTase variant, which variant at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAETWPAF (SEQ ID NO:5), and which variant at position 195 holds a leucine residue (Y195L).

A CGTase variant, which variant at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAEADPNF (SEQ ID NO:6).

A CGTase variant, which variant at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAEADPNF (SEQ ID NO:6), and which variant at position 195 holds a leucine residue (Y195W).

Preferably, the above CGTase variants are derived from a strain of *Bacillus autolyticus,* a strain of *Bacillus cereus*, a strain of *Bacillus circulans*, a strain of *Bacillus circulans var. alkalophilus,* a strain of *Bacillus coagulans*, a strain of *Bacillus firmus*, a strain of *Bacillus halophilus*, a strain of *Bacillus macerans,* a strain of *Bacillus megaterium,* a strain of *Bacillus ohbensis*, a strain of *Bacillus stearothermophilus,* or a strain of *Bacillus subtilis.*

Most preferred, the above CGTase variants are derived from the strain Bacillus sp. Strain 1011, the strain Bacillus sp. Strain 38-2, the strain Bacillus sp. Strain 17-1, the strain Bacillus sp. 1-1, the strain Bacillus sp. Strain B1018, the strain *Bacillus circulans* Strain 8, or the strain *Bacillus circulans* Strain 251, or a mutant or a variant thereof.

In yet another preferred embodiment, the CGTase variant of the invention is a CGTase variant derived from an enzyme obtainable from a strain of Thermoanaerobacter, which enzyme has been modified by substitution, insertion and/or deletion at one or more of the amino acid positions corresponding to the positions stated in Table 13, below. Such modification lead to CGTase variants of increased product selectivity, as indicated in the table.

Preferably the CGTase variant is derived from a strain of Thermoanaerobacter sp. ATCC 53627, or a mutant or a variant thereof.

TABLE 13

Thermoanaerobacter Derived CGTase Variants of Increased Product Selectivity Positions Identified by CGTase Numbering

| Position | α-cyclodextrin | β-cyclodextrin | γ-cyclodextrin |
|---|---|---|---|
| 21 | F,Y | F,Y | F,Y |
| 47 | Q,L | A,Q,H,R,L | A,Q,H,R,L |
| 87 | I,H | I,H | I,H |
| 88 | N,K,H | N,K,H | N,K,H |
| 89 | G,A,Y,E,* | G,A,E,K,R,Y,P,* | G,A,Y,P,* |
| 90 | — | G,A | G,A |
| 91 | A,V,D,G | A,V,G,S | A,V,G,S |
| 91a | A,V,G,Y,* | A,V,G,Y,* | A,V,G,Y,* |
| 92 | V,* | V,* | V,* |
| 93 | N,* | N,H,T,* | N,H,T,* |
| 94 | Q,K,R,W,F,N,* | Q,K,R,W,F,N,* | Q,K,R,W,F,N,* |
| 98 | — | G,A | G,A |
| 101 | — | G,A | G,A,F,Y |
| 135 | L | L | L |
| 140 | A,R,N | A,R,N | A,R,N |
| 143 | G,S | — | — |
| 144 | K,R,D,N,E,Q | — | — |
| 145 | A,E,W,P,G,F,Y,P,R,K | A,E,L,W | A,E,L,W |
| 145a | P,A,F,Q,S,W,I,R,* | P,A,I,Q,S | I,A,Q,P,S |
| 146 | P,A,F,Q,S,W,I,R,G,* | P,A,I,Q,S,K,D,N,R,F,W,* | I,A,Q,P,S |
| 147 | A,L,I,F,* | A,L,I,F,W,G,Y,R,D,* | S,A,D |
| 147a | * | * | D,N,E,Q,T |
| 148 | G,A,N | G,A,N,Q | E,R,K,Y,F,N,Q |
| 149 | — | W | L,I,F,W |
| 150 | A,G | A,S | A,S,N |
| 167 | P,F | A,F | A,F,P |
| 168 | S | S | S |
| 178 | N | N | N |
| 179 | S,N,D | S,N,D | S,N,D |
| 180 | S,N,D | S,N,D | S,N,D |
| 183 | W,Y,A | W,Y,A | W,Y,A |
| 185 | P,H,R,E,D | P,H,R,E,D | P,H,R,E,D |
| 192 | K | K | K |
| 193 | G,D,E,Q | G,A | G,A |
| 195 | Y | L,I,W,Y | L,I,W,Y |
| 196 | A,S,N,G | A,S,N,G | A,S,N,G |
| 197 | D,E | D,E | D,E |
| 232 | Q,L | Q,L | Q,L |
| 233 | Q,N,I | Q,N,I | Q,N,I |
| 259 | F,W,A | F,W,A | F,W,A |
| 264 | Q | Q | Q |
| 326 | Q,F,L | Q,F,L | Q,F,L |
| 370 | — | T,N | T,N |
| 371 | A,S,N,G,E,Q | A,G,N,S | A,G,N,V,L,I,S |
| 373 | D,N | D,E | D,E |
| 375 | — | A,P,G,K | A,P,G,K |
| 600 | X | X | X |

X = any natural amino acid residue
— conserved residue
* deleted or absent residue In yet another preferred embodiment, the CGTase variant of the invention is a CGTase variant derived from an enzyme obtainable from a strain of Thermoanaerobacter, which enzyme has been modified by substitution, insertion and/or deletion at one or more of the amino acid residues corresponding to the positions stated in Table 14, below. Such modifications lead to CGTase variants of reduced product inhibition.

Preferably the CGTase variant is derived from a strain of Thermoanaerobacter sp. ATCC 53627, or a mutant or a variant thereof.

TABLE 14

Thermoanaerobacter Derived CGTase Variants of Reduced Product Inhibition Positions Identified by CGTase Numbering

| | |
|---|---|
| 47 | A,Q,L |
| 89 | G |
| 100 | A,I,L,F |
| 185 | R,E,D |
| 186 | A |
| 196 | A,L |
| 232 | Q,N,A,L |
| 264 | A,N,L |
| 268 | A |
| 339 | A |
| 371 | G,N,A,L,S,E,Q |
| 375 | G,Q,N,A,L,K |
| 382 | A,L,V |
| 384 | A,L,V |

TABLE 14-continued

Thermoanaerobacter Derived CGTase Variants of Reduced
Product Inhibition Positions Identified by CGTase Numbering

| | |
|---|---|
| 413 | A,V,G |
| 598 | A,V,G,P |
| 599a | P,R,H |
| 600 | X |
| 603 | A,V,L,G |
| 616 | A,I,L,G |
| 626 | A,I,V,L,G |
| 627 | A,V,L,G |
| 628 | A,V,L,G |
| 633 | A,V,L,I,G |
| 636 | I,L,A,G |
| 649 | A,G |
| 651 | A,G,V |
| 662 | A,L,I,G |
| 667 | A |

X = any natural amino acid residue

As its most preferred embodiments, the invention provides the following CGTase variants, derived from a strain of Thermoanaerobacter sp., preferably the strain of Thermoanaerobacter ATCC 53627, or a mutant or a variant thereof:

A CGTase variant, which variant at position 21 holds a phenylalanine residue (V21F) or a tyrosine residue (V21Y).

A CGTase variant, which variant at position 47 holds a glutamine residue (K47Q), or an alanine residue (K47A), or a leucine residue (K47L), or a histidine residue (K47H), or an arginine residue (K47R).

A CGTase variant, which variant at position 88 holds a lysine residue (P88K).

A CGTase variant, which variant at position 89 holds an alanine residue (D89A), or a glycine residue (D89G).

A CGTase variant, which variant at position 91a holds an alanine residue (F91aA) or a tyrosine residue (F91aY), or in which variant position 91a has been deleted (F91a*).

A CGTase variant, in which variant position 92 has been deleted (G92*).

A CGTase variant, which variant at position 94 holds a glutamine residue (S94Q), or a lysine residue (S94K), or an arginine residue (S94R), or a tryptophan residue (S94W), or a phenylalanine residue (S94F), or in which variant position 94 has been deleted (S94*).

A CGTase variant, which variant at position 135 holds a leucine residue (D135L).

A CGTase variant, which variant at position 143 holds a natural amino acid residue different from that of the wild-type enzyme (p143X).

A CGTase variant, which variant at position 143 holds an alanine residue (P143A), or holds a glycine residue (P143G).

A CGTase variant, which variant at position 144 holds a natural amino acid residue different from that of the wild-type enzyme (A145X).

A CGTase variant, which variant at position 144 holds an arginine residue (A144R), or a lysine residue (A144K), or an aspartic acid residue (A144D).

A CGTase variant, which variant at position 145 holds a natural amino acid residue different from that of the wild-type enzyme (S145X).

A CGTase variant, which variant at position 145 holds an alanine residue (S145A), or a glutamic acid (S145E), or a tryptophan residue (S145W), or a glycine residue (S145G), or a phenylalanine residue (S145F), or a tyrosine residue (S145Y), or a leucine residue (S145L).

A CGTase variant, which variant at position 145a (via insertion) holds a natural amino acid residue (*145aX).

A CGTase variant, which variant at position 145a (via insertion) holds an isoleucine residue (*145aI).

A CGTase variant, which variant at position 146 holds a natural amino acid residue different from that of the wild-type enzyme (E145X).

A CGTase variant, which variant at position 146 holds a proline residue (E146P), or a serine residue (E146S), or an isoleucine residue (E146I), or a glutamine residue (E146Q), or a tryptophan residue (E146W), or an arginine residue (E146R).

A CGTase variant, which variant at position 147 holds a natural amino acid residue different from that of the wild-type enzyme (T147X).

A CGTase variant, which variant at position 147 holds an isoleucine residue (T147I), or a leucine residue (T147L), or an alanine residue (T147A), or a serine residue (T147S), or a tryptophan residue (T147W).

A CGTase variant, which variant at position 147a (via insertion) holds a natural amino acid residue (*147aX).

A CGTase variant, which variant at position 147a (via insertion) holds an alanine residue (*147aA).

A CGTase variant, which variant at position 148 holds a natural amino acid residue different from that of the wild-type enzyme (D148X).

A CGTase variant, which variant at position 148 holds an alanine residue (D148A), or a glycine residue (D148G), or a glutamic acid residue (D148E), or an asparagine residue (D148N).

A CGTase variant, which variant at position 149 holds a natural amino acid residue different from that of the wild-type enzyme (P149X).

A CGTase variant, which variant at position 149 holds an isoleucine residue (P149I).

A CGTase variant, which variant at position 167 holds a phenylalanine residue (Y167F).

A CGTase variant, which variant at position 179 holds a serine residue (G179S), an asparagine residue (G179N), or an aspartic acid residue (G179D).

A CGTase variant, which variant at position 180 holds a serine residue (G180S), an asparagine residue (G180N), or an aspartic acid residue (G180D).

A CGTase variant, which variant at position 185 holds an arginine residue (S185R), or a glutamic acid residue (S185E), or an aspartic acid residue (S185D).

A CGTase variant, which variant at position 186 holds an alanine residue (Y186A).

A CGTase variant, which variant at position 193 holds a natural amino acid residue different from that of the wild-type enzyme (N193X).

A CGTase variant, which variant at position 193 holds a glycine residue (N193G), or an alanine residue (N193A), or an aspartic acid residue (N193D), or a glutamic acid residue (N193E).

A CGTase variant, which variant at position 195 holds a natural amino acid residue different from that of the wild-type enzyme (F195X).

A CGTase variant, which variant at position 196 holds a natural amino acid residue different from that of the wild-type enzyme (D196X).

A CGTase variant, which variant at position 196 holds an alanine residue (D196A), a serine residue (D196S), or a leucine residue (D196L).

A CGTase variant, which variant at position 197 holds an aspartic acid residue (L197D), or a glutamic acid residue (L197E).

A CGTase variant, which variant at position 232 holds a glutamine residue (K232Q), or an asparagine residue (K232N), or an alanine residue (K232A), or a leucine residue (K232L).

A CGTase variant, which variant at position 233 holds a glutamine residue (H233Q).

A CGTase variant, which variant at position 259 holds a phenylalanine residue (Y259F).

A CGTase variant, which variant at position 264 holds a glutamine residue (E264Q), or an alanine residue (E264A), or an asparagine residue (E264N), or a leucine residue (E264L).

A CGTase variant, which variant at position 268 holds an alanine residue (N268A).

A CGTase variant, which variant at position 371 holds a natural amino acid residue different from that of the wild-type enzyme (D371X).

A CGTase variant, which variant at position 371 holds a glycine residue (D371G), or an asparagine residue (D371N), or an alanine residue (D371A), or a leucine residue (D371L), or a glutamic acid residue (D371E).

A CGTase variant, which variant at position 375 holds a natural amino acid residue different from that of the wild-type enzyme (R375X).

A CGTase variant, which variant at position 375 holds a proline residue (R375P), or a glycine residue (R375G), or a glutamine residue (R375Q), or an asparagine residue (R375N), or an alanine residue (R375A), or a leucine residue (R375L).

A CGTase variant, which variant at position 599a (via insertion) holds a proline residue (*599aP), or an arginine residue (*599aR), or a histidine residue (*599aH).

A CGTase variant, which variant position 600 has been substituted for a different amino acid residue, in particular a phenylalanine residue (W600F), a tyrosine residue (W600Y), an arginine residue (W600R), a proline residue (W600P), a leucine residue (W600L), or an asparagine residue (W600N).

A CGTase variant, which variant at position 616 holds an alanine residue (W616A).

A CGTase variant, which variant at position 633 holds an alanine residue (Y633A).

A CGTase variant, which variant at position 662 holds an alanine residue (W662A).

A CGTase variant, which variant at position 47 holds a histidine residue or an arginine residue, and/or at position 135 holds a leucine residue (K47H/D135L or K47R/D135L).

A CGTase variant, which variant at positions 87–94 comprises the partial amino acid sequence IKYSGVNN (SEQ ID NO:11), or the partial amino acid sequence INDS-GVNN (SEQ ID NO:58), and/or at positions 143–151 comprises the partial amino acid sequence GRAGTNPGF (SEQ ID NO:12), or at positions 143–145 comprises the partial amino acid sequence GRW, and/or at position 195 holds a tyrosine residue (F195Y).

A CGTase variant, which variant at positions 87–94 comprises the partial amino acid sequence INDSGVNN (SEQ ID NO:58), and/or at positions 146–150 comprises the partial amino acid sequence SDQPS (SEQ ID NO:59).

A CGTase variant, which variant at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAETWPAF (SEQ ID NO:5).

A CGTase variant, which variant at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAETWPAF (SEQ ID NO:5), and which variant at position 195 holds a leucine residue (F195L).

A CGTase variant, which variant at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAEADPNF (SEQ ID NO:6).

A CGTase variant, which variant at positions 87–94 comprises the partial amino acid sequence HP*SGY** (SEQ ID NO:3), and/or at positions 143–151 comprises the partial amino acid sequence PALETNPNF (SEQ ID NO:4), or at positions 143–151 comprises the partial amino acid sequence PAAEADPNF (SEQ ID NO:6), and which variant at position 195 holds a leucine residue (F195W).

A CGTase variant, in which variant positions 92 and 94 have been deleted (G92*/S94*).

A CGTase variant, which variant at position 143 holds an alanine residue, and at position 144 holds an arginine residue (P143A/A144R).

A CGTase variant, which variant at position 143 holds a glycine residue, and at position 144 holds an arginine residue, and at position 145 holds a tryptophan residue (P143G/A144R/S145W).

A CGTase variant, which variant at position 143 holds a glycine residue, and at position 144 holds an arginine residue, and at position 145 holds a tryptophan residue (P143G/A144R/S145W), and which variant at position 179 holds a serine residue (G179S), an asparagine residue (G179N), or an aspartic acid residue (G179D), and/or at position 180 holds an asparagine residue (G180N), or an aspartic acid residue (G180D).

A CGTase variant, which variant at positions 143–148 comprises the partial amino acid sequence GRA**A (SEQ ID NO:7), the partial amino acid sequence GRAAAA (SEQ ID NO:8), the partial amino acid sequence GRPAAA (SEQ ID NO:64), the partial amino acid sequence GRAPAA (SEQ ID NO:9), or the partial amino acid sequence GRGPAA (SEQ ID NO:10).

A CGTase variant, which variant at positions 143–151 comprises the partial amino acid sequence GRAGTNPG (SEQ ID NO:12).

A CGTase variant, which variant at positions 143–151 comprises the partial amino acid sequence GRAGTNPG (SEQ ID NO:12), and at position 195 holds a tyrosine residue (F195Y).

A CGTase variant, which variant at position 144 holds an arginine residue, at position 145 holds an alanine residue, and at position 146 holds a proline residue (A144R/S145A/E146P).

A CGTase variant, which variant at position 145 holds an alanine residue, and at position 145a (via insertion) holds an isoleucine residue (S145A/*145aI).

A CGTase variant, which variant at position 145 holds an alanine residue, and at position 146 holds a glycine residue (S145A/E146G).

A CGTase variant, which variant at position 145 holds a leucine residue, and at position 148 holds an asparagine residue (S145L/D148N).

A CGTase variant, which variant at position 145 holds a glutamic acid residue, and in position 146 holds a proline residue or a glutamine residue (S145E/E146P or S145E/E146Q).

A CGTase variant, which variant at position 145 holds a tryptophan residue, and in position 146 holds a tryptophan residue, or an isoleucine residue, or an arginine residue (S145W/E146W or S145W/E146I or S145W/E146R).

A CGTase variant, which variant at position 145 holds an alanine residue, at position 145a (via insertion) holds an isoleucine residue, and at position 148 holds a glutamic acid residue (S145A/*145aI/D148E).

A CGTase variant, which variant at position 145a (via insertion) holds an isoleucine residue, and at position 148 holds a glutamic acid residue (*145aI/D148E).

A CGTase variant, which variant at position 616 holds an alanine residue, and at position 662 holds an alanine residue (W616A/W662A).

Methods of Producing CGTase Variants

The production of the CGTase variants of the invention follows the general principles of recombinant DNA technology, e.g. as described by Sambrook et al. [Sambrook J, Fritsch E F, Maniatis T; *Molecular Cloning: A Laboratory Manual,* Cold Spring Harbor Laboratory Press, 1989, New York], and known to the person skilled in the art.

Formally, the production takes rise in the provision of a DNA construct encoding CGTase variant of the invention.

DNA Constructs

In another aspect, the invention provides a DNA construct encoding a CGTase variant of the invention. As defined herein, the term "DNA construct" is intended to indicate any nucleic acid molecule of cDNA, genomic DNA, synthetic DNA or RNA origin. The term "construct" is intended to indicate a nucleic acid segment which may be single- or double-stranded, and which may be based on a complete or partial naturally occurring nucleotide sequence encoding the CGTase variant of interest. The construct may optionally contain other nucleic acid segments.

The DNA construct of the invention may be prepared by suitably modifying a DNA sequence encoding the precursor CGTase, which modification may bring about:

(i) introduction of one or more amino acid residues at one or more different sites in the amino acid sequence; and/or (ii) substitution of one or more amino acid residues at one or more different sites in the amino acid sequence; and/or (iii) deletion of one or more amino acid residues at one or more sites in the amino acid sequence.

The modification of the DNA sequence may be performed by site-directed mutagenesis or by random mutagenesis, or by a combination of these techniques in accordance with well-known procedures, e.g. as described by Sambrook et al., op cit.

In more preferred embodiments, the DNA construct of the invention comprises one or more of the partial oligonucleotide sequences (primers) described in the examples below. These partial oligonucleotide sequences are in particular 5'-G GTC GTT TAC CA<u>G GCG CCG</u> AAC TGG-3' (Y633A) (SEQ ID NO: 13);
5'-GC <u>GAG CTC</u> GGG AAC GCG GAC CCG-3' (W616A:) (SEQ ID NO: 14);
5'-CC GTC A<u>CC GCG G</u>AA GGC GGC-3' (W662A) (SEQ ID NO: 15);
5'-GC ATC TAC A<u>AG GGC CT</u>G TACGAT CTC G-3' (N193G) (SEQ ID NO: 16);
5'-GCA TCA TCA AT<u>G GAT CC</u>G GCG TAA AC-3' (Y89G) (SEQ ID NO: 17);
5'-CAT ACG TCG CCC <u>GCT AGC</u> ATT TCC GAC CAG CCT TCC-3' (145aI) (SEQ ID NO: 18);
5'-CG GGC GGG <u>ACC GGT</u> CCG GAC AAC CG-3' (D371G) (SEQ ID NO: 19);
5'-G TCG GGC <u>GGT ACC</u> AAT CCG GAC AAC C-3' (D371N) (SEQ ID NO: 20);
5'-CG TTC <u>ATC GAT</u> CAG CAT GAC ATG G-3' (N326Q) (SEQ ID NO: 21);
5'-GC ATC ATC AAT GAT <u>TCC GGA</u> GTA AAC AAC ACG GC-3' (Y89D); (SEQ ID NO: 65) and
5'-G CCC GCC TC<u>T CCG GA</u>C CAG CCT TC-3' (S146P) (SEQ ID NO: 22);
and the the partial oligonucleotide sequences (primers) described as primers A1-A24, primers B1-B15, and C1-C9, of Examples 5, 6 and 7.

Expression Vectors

Subsequent to modification, the CGTase variant may be obtained by combining the DNA construct encoding the CGTase variant of the invention with an appropriate expression signal in an appropriate expression vector.

The expression vector of the invention may be any expression vector that is conveniently subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the expression vector of the invention, the DNA sequence encoding the CGTase variant preferably is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the CGTase variant.

Thus, in the expression vector of the invention, the DNA sequence encoding the CGTase variant preferably should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the CGTase variant, the promoter and the terminator, respectively, and to insert them into suitable vectors are well known to persons skilled in the art (cf., for instance, Sambrook et al., op cit)

The promoter may be any DNA sequence which shows transcriptional activity in the host cell of choice and may be derived from genes encoding proteins either homologous or heterologous to the host cell.

Examples of suitable promoters for directing the transcription of the DNA encoding the CGTase variant of the invention in bacterial host cells include the promoter of the *Bacillus stearothermophilus* maltogenic amylase gene, the *Bacillus licheniformis* alpha-amylase gene, the *Bacillus amyloliquefaciens* BAN amylase gene, the *Bacillus subtilis* alkaline protease gen, or the *Bacillus pumilus* xylanase or xylosidase gene, or by the phage Lambda $P_R$ or $P_L$ promoters or the *E. coli* lac, trp or tac promoters.

Examples of suitable promoters for use in yeast host cells include promoters from yeast glycolytic genes [Hitzeman et al., *J. Biol. Chem.* 1980 255 12073–12080; Alber and Kawasaki, *J. Mol Appl. Gen.* 1982 1 419–434] or alcohol dehydrogenase genes [Young et al., in *Genetic Engineering of Microorganisms for Chemicals* (Hollaender et al, Eds.), Plenum Press, New York, 1982], or the TPI1 [U.S. Pat. No. 4,599,311] or ADH2-4c [Russell et al., *Nature* 1983 304 652–654] promoters.

Examples of suitable promoters for use in filamentous fungus host cells are, for instance, the ADH3 promoter [McKnight et al., *EMBO J.* 1985 4 2093–2099] or the tpiA promoter. Examples of other useful promoters are those derived from the gene encoding A. oryzae TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters.

The expression vector of the invention may further comprise a DNA sequence enabling the vector to replicate in the host cell in question. The expression vector may also comprise a selectable marker, e.g. a gene the product of which complements a defect in the host cell, such as the gene coding for dihydrofolate reductase (DHFR) or the *Schizosaccharomyces pombe* TPI gene [Russell P R; *Gene* 1985 40 125–130], or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD and sC.

To direct the CGTase into the secretory pathway of the host cells, a secretory signal sequence (also known as a leader sequence, prepro sequence or pre sequence) may be provided in the expression vector. The secretory signal sequence is joined to the DNA sequence encoding the CGTase in the correct reading frame. Secretory signal sequences are commonly positioned 5' to the DNA sequence encoding the CGTase variant. The secretory signal sequence may be that normally associated with the CGTase or may be from a gene encoding another secreted protein.

In a preferred embodiment, the expression vector of the invention may comprise a secretory signal sequence substantially identical to the secretory signal encoding sequence of the *Bacillus licheniformis* α-amylase gene, e.g. as described in WO 86/05812.

Also, measures for amplification of the expression may be taken, e.g. by tandem amplification techniques, involving single or double crossing-over, or by multicopy techniques, e.g. as described in U.S. Pat. No. 4,959,316 or WO 91/09129. Alternatively the expression vector may include a temperature sensitive origin of replication, e.g. as described in EP 283,075.

Procedures for ligating DNA sequences encoding the CGTase variant, the promoter and optionally the terminator and/or secretory signal sequence, respectively, and to insert them into suitable vectors containing the information necessary for replication, are well known to persons skilled in the art (cf., for instance, Sambrook et al., op cit).

Host Cells

In yet another aspect the invention provides a host cell comprising the DNA construct of the invention and/or the recombinant expression vector of the invention.

The host cell of the invention, into which the DNA construct or the recombinant expression vector of the invention is to be introduced, may be any cell, preferably a non-pathogenic cell, which is capable of producing the CGTase variant and includes bacteria, yeast, fungi and higher eukaryotic cells.

Examples of bacterial host cells which, on cultivation, are capable of producing the CGTase variant of the invention are grampositive bacteria such as strains of Bacillus, in particular a strain of *B. subtilis, B. licheniformis, B. lentus, B. brevis, B. stearothermophilus, B. alkalophilus, B. amyloliquefaciens, B. coagulans, B. circulans, B. lautus, B. megatherium, B. pumilus, B. thuringiensis* or *B. agaradherens,* or strains of Streptomyces, in particular a strain of *S. lividans* or *S. murinus,* or gramnegative bacteria such as *Echerichia coli.* The transformation of the bacteria may be effected by protoplast transformation or by using competent cells in a manner known per se (cf. Sambrook et al., op cit).

When expressing the CGTase variant in bacteria such as *E. coli,* the CGTase may be retained in the cytoplasm, typically as insoluble granules (known as inclusion bodies), or may be directed to the periplasmic space by a bacterial secretion sequence. In the former case, the cells are lysed and the granules are recovered and denatured after which the CGTase is refolded by diluting the denaturing agent. In the latter case, the CGTase may be recovered from the periplasmic space by disrupting the cells, e.g. by sonication or osmotic shock, to release the contents of the periplasmic space and recovering the CGTase variant.

Examples of suitable yeasts cells include cells of Saccharomyces spp. or Schizosaccharomyces spp., in particular strains of *Saccharomyces cerevisiae* or *Saccharomyces kluyveri.* Methods for transforming yeast cells with heterologous DNA and producing heterologous polypeptides therefrom are described, e.g. in U.S. Pat. No. 4,599,311, U.S. Pat. No. 4,931,373, U.S. Pat. No. 4,870,008, 5,037,743, and U.S. Pat. No. 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequence encoding the CGTase variant of the invention may be preceded by a signal sequence and optionally a leader sequence , e.g. as described above. Further examples of suitable yeast cells are strains of Kluyveromyces, such as *K. lactis,* Hansenula, e.g. *H. polymorpha,* or Pichia, e.g. *P. pastoris* [Gleeson et al., *J. Gen. Microbiol.* 1986 132 3459–3465; U.S. Pat. No. 4,882, 279].

Examples of other fungal cells are cells of filamentous fungi, e.g. Aspergillus spp., Neurospora spp., Fusarium spp. or Trichoderna spp., in particular strains of *A. oryzae, A. nidulans* or *A. niger.* The use of Aspergillus spp. for the expression of proteins have been described in e.g., EP 272,277 and EP 230,023. The transformation of F. oxysporum may, for instance, be carried out as described by Malardier et al., *Gene* 1989 78 147–156.

The transformed or transfected host cell described above is then cultured in a suitable nutrient medium under conditions permitting the expression of the CGTase, after which the resulting CGTase variant is recovered from the culture.

The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The CGTase variant produced by the cells may then be recovered from the culture medium by conventional procedures including separating the host cells from the medium by centrifugation or filtration, precipitating the proteinaceous components of the supernatant or filtrate by means of a salt, e.g. ammonium sulphate, purification by a variety of chromatographic procedures, e. g. ion exchange chromatography, gelfiltration chromatography, affinity chromatography, or the like, dependent on the type of CGTase in question.

Method of Producing CGTase Variants

In a still further aspect, the present invention provides a method of producing the CGTase variant of the invention, wherein a suitable host cell, which has been transformed with a DNA sequence encoding the CGTase, is cultured under conditions permitting the production of the enzyme, and the resulting enzyme is recovered from the culture.

The medium used to culture the transformed host cells may be any conventional medium suitable for growing the host cells in question. The expressed CGTase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

Industrial Applications

The CGTase variant of the invention find application in processes for the manufacture of cyclodextrins for various industrial applications, particularly in the food, cosmetic, chemical, agrochemical and pharmaceutical industries.

Therefore, in another aspect, the invention provides CGTase variants for use in a process for the manufacture of cyclodextrins, in particular $\alpha$-, $\beta$-, $\gamma$-, $\delta$-, $\epsilon$-, and/or $\zeta$-cyclodextrins. In a more preferred embodiment, the invention provides CGTase variants for use in a process for the manufacture of $\alpha$-, $\beta$- and $\gamma$-cyclodextrins, or mixtures hereof. In another preferred embodiment, the invention provides CGTase variants for use in a process for the manufacture of $\delta$-, $\epsilon$-, and $\Lambda$-cyclodextrins, or mixtures hereof.

The CGTase variants of the invention may also be used in a process for the manufacture of linear oligosaccharides, in particular linear oligosaccharides of 2 to 12 glucose units, preferably linear oligosaccharides of 2 to 9 glucose units.

In yet another preferred embodiment, the CGTase variants of the invention may be used for in situ generation of cyclodextrins. In this way the CGTase variants of the invention may be added to a substrate containing medium in which the enzyme variants are capable of forming the desired cyclodextrins. This application is particularly well suited for being implemented in methods of producing baked products, in methods for stabilizing chemical products during their manufacture, and in detergent compositions.

Certain cyclodextrins are known to improve the quality of baked products. The CGTase variants of the invention therefore also may be used for implementation into bread-improving additives, e.g. dough compositions, dough additives, dough conditioners, pre-mixes, and similar preparations conventionally used for adding to the flour and/or the dough during processes for making bread or other baked products.

Cyclodextrins have an inclusion ability useful for stabilization, solubilization, etc. Thus cyclodextrins can make oxidizing and photolytic substances stable, volatile substances non-volatile, poorly-soluble substances soluble, and odoriferous substances odorless, etc. and thus are useful to encapsulate perfumes, vitamins, dyes, pharmaceuticals, pesticides and fungicides. Cyclodextrins are also capable of binding lipophilic substances such as cholesterol, to remove them from egg yolk, butter, etc.

Cyclodextrins also find utilization in products and processes relating to plastics and rubber, where they have been used for different purposes in plastic laminates, films, membranes, etc. Also cyclodextrins have been used for the manufacture of biodegradable plastics.

EXAMPLES

The invention is further illustrated with reference to the following examples which are not intended to be in any way limiting to the scope of the invention as claimed.

Example 1

Crystal Structure and Molecular Modelling of a CGTase Enzymes

The CGTase from *Bacillus circulans* Strain 251 [cf. Lawson C L, van Montfort R, Strokopytov B, Rozeboom H J, Kalk K H, de Vries G E, Penninga D, Dijkhuizen L, and Dijkstra B W; *J. Mol. Biol.* 1994 236 590–600] was soaked in a buffer solution containing the non-hydrolyzable tetrasaccharide acarbose, and an X-ray structure of the CGTase including the pseudo-tetrasaccharide located in the catalytic site was obtained, cf. Strokopytov et al. [Strokopytov B, Penninga D, Rozeboom H J, Kalk K H, Dijkhuizen L and Dijkstra B W; *Biochemistry* 1995 34 2234–2240]. Coordinates of this structure have been deposited with the Protein Data Bank, Biology Department, Bldg. 463, Brookhaven National Laboratory, P.O. Box 5000, Upton, N.Y. 11973-5000, USA, under the entry code 1CXG.

By additional soaking in a buffer containing maltoheptaose, a nonasaccharide (A-I) was formed in an enzyme-substrate-complex structure. Coordinates of this structure have been deposited with the Protein Data Bank, Biology Department, Bldg. 463, Brookhaven National Laboratory, P.O. Box 5000, Upton, N.Y. 11973-5000, USA, under the entry code 1DIJ. By further adding a trisaccharide (J-L) to the non-reducing end of the nonasaccharide by computer modelling, the substrate binding cleft and the residues involved herein in the A and B domain have been located.

By aid of a computer program, Insight™ Software Package from Biosym, using subset-zone function, positions within selected distances could be identified. In this way Tables 1–4 were generated.

The residues listed in FIG. 1 are referring to *Bacillus circulans* Strain 251 CGTase and comprise only the closest contacts between the substrate and the enzyme. By changing the number of hydrogen-bonds and other interactions between the enzyme and the substrate, the product selectivity can be altered. Normally, cleavage of the starch takes place between glucose unit B and C in the model.

By computer modelling, a trisaccharide has been added to the reducing end of the acarbose (A) and to the non-reducing end of a pentasaccharide located in the E-domain, and hereby linking together the substrate binding sites in the A–B and E-domains. In total a substrate of 20 glucose-units has been located in the enzyme.

The structure of a Thermoanaerobacter CGTase was modelled based on the known structure of *Bacillus circulans* CGTase. Again the computer program Insight™ from Biosym was employed, using the homology module, according to the manufacturers instructions. The substrate found in *Bacillus circulans* was docked into the Thermoanaerobacter model, and the positions stated in Tables 5–7 identified.

Example 2

Construction of $\alpha$-cyclodextrin Producing CGTase Variants from Bacillus

This example describes the construction of three $\alpha$-cyclodextrin producing CGTase variants, in which site-directed mutagenesis have lead to an altered number of hydrogen bonds in the subsites of the active site cleft. The variants are derived from a *Bacillus circulans* Strain 251 CGTase (i.e. the wild-type enzyme), obtained as described by Lawson et al. [Lawson C L, van Montfort R, Strokopytov B, Rozeboom H J, Kalk K H, de Vries G E, Penninga D, Dijkhuizen L, and Dijkstra B W; *J. Mol. Biol.* 1994 236 590–600].

For construction of the variants a method based on PCR for site-directed mutagenesis. The following oligonucleotides (primers) were used to produce the mutations:

Y89G: 5'-GCA TCA TCA ATG GAT CCG GCG TAA AC-3' (Bam HI) (SEQ ID NO: 17); and
S146P: 5'-G CCC GCC TCT CCG GAC CAG CCT TC-3' (BspE I) (SEQ ID NO: 22).

Successful mutagenesis resulted in appearance of the underlined restriction sites, allowing rapid screening of potential mutants.

The mutations were confirmed by restriction analysis and sequencing. Mutant proteins were produced by the use of an amylase and protease negative *Bacillus subtilis* strain, and purified using affinity chromatography.

CGTase activity was determined by incubating appropriately diluted enzyme solutions with substrate in 10 mM sodium citrate, pH 6.0, for 5–10 minutes at 50° C.

Cyclodextrin forming activity (transglycosylation activity) was determined using 5% Paselli™ SA2 (i.e. partially hydrolysed potato starch with an average degree of polymerization of 50, available from AVEBE, Foxhol, The Netherlands) as substrate. The β-cyclodextrin formed was determined with phenolphthalein. One unit of activity is defined as the amount of enzyme able to produce 1 µmol of β-cyclodextrin per minute. α- and β-cyclodextrin formation was subsequently determined by use of HPLC (cf. below).

Cyclodextrin formation was also determined under industrial production process conditions. For this purpose 0.1 U/ml CGTase was incubated with 10% Paselli™ WA4 (i.e. jet-cooked, pre-gelatinized drum-dried starch) in a 10 mM sodium citrate buffer (pH 6.0) at 50° C. for 45 hours. Samples were collected at regular intervals of time, boiled for 5 minutes, and the products formed analyzed by HPLC using a 25 cm Econosil-NH$_2$ 10 micron column (Alltech Associates Inc., USA) eluted with acetonitril/water (60/40% v/v) at a flow rate of 1 ml per minute.

Results

Figure 2A:
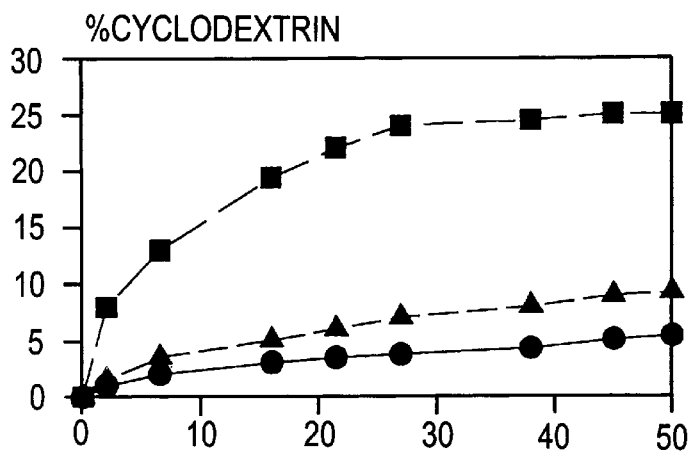
FIG. 2 shows the formation (% cyclodextrin) of α- (●), β- (■), and γ-cyclodextrin (▲) from 10% Paselli™ WA4 (pre-gelatinized drum-dried starch) during a 50 hour incubation at 50° C. catalyzed by (A) wild-type enzyme (*Bacillus circulans* Strain 251 CGTase), (B) the Y89D CGTase variant, (C) the S146P CGTase variant, and (D) the Y89D/S146P CGTase variant.
Figure 2B:
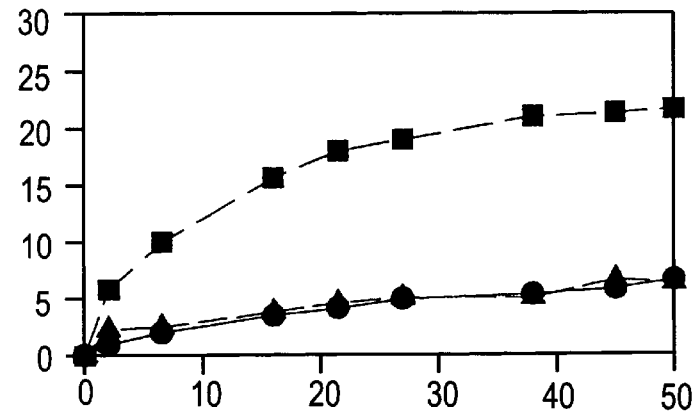

Variants were designed in order to increase α-cyclodextrin formation. In the first experiment, a tyrosine residue at position 89 was changed into an aspartic acid residue (Y89D), which introduces an additional hydrogen bond with subsite F of the substrate, cf. FIG. 1. This gives rise to stronger binding of the amylose chain in the active site cleft, with the formation of smaller cyclodextrins. In result an increase in β-cyclodextrin forming activities was detected, with a simultaneous decrease in the β-cyclodextrin forming activity, as seen from the ratio of cyclodextrins produced from Paselli™ WA4, cf. Table 16, below, and in the cyclodextrin formation profiles, cf. FIG. 2B.

Figure 2C:
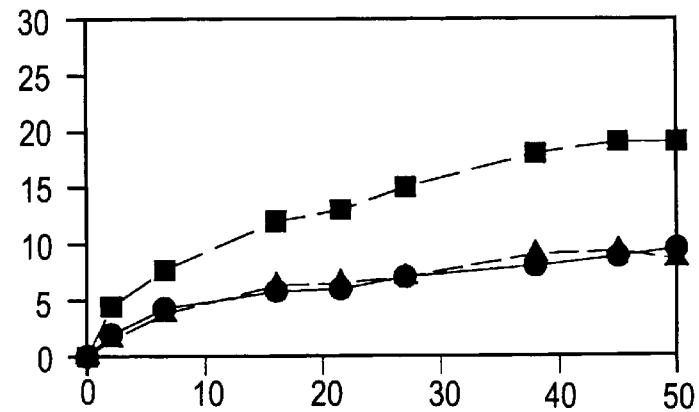

In a second experiment, serine at position 146 was changed into a proline residue (S146P). This gives rise to a dramatic change in the hydrogen network at subsite I of the substrate, cf. FIG. 1. As seen from Table 15 below, this mutation has a substantial impact on the cyclodextrin forming activities. The α-cyclodextrin forming activity increased drastically at the expense of the β-cyclodextrin forming activity. There was little effect on the γ-cyclodextrin forming activity. This also corresponds with the ratio of cyclodextrins determined and presented in Table 16 and in FIG. 2C.

Figure 2D:
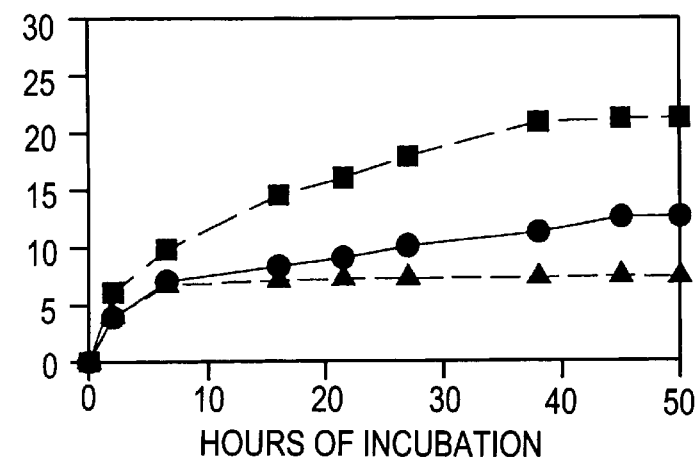

In a third experiment, a double mutation was accomplished. In this experiment tyrosine at position 89 was changed into an aspartic acid residue, and serine at position 146 was changed into a proline residue (Y89D/S146P). These mutations results in a combination of the effects seen from the two single mutations carried out as described above. This variant possesses the largest α-cyclodextrin forming activity, cf. Table 15, and the largest formation of α-cyclodextrin, cf. Table 16 and FIG. 2D.

TABLE 15

Specific Activities of α- β- AND γ-CD Forming CGTases

| Enzyme | Cyclization Activity (U/mg) | | |
|---|---|---|---|
|  | α | β | γ |
| Wild-type | 2 | 280 | 80 |
| Y89D | 5 | 270 | 47 |
| S146P | 25 | 104 | 82 |
| Y89D/S146P | 35 | 109 | 79 |

TABLE 16

Ratio of Cyclodextrin Formation from 10% Paselli ™ WA4 (at 50° C. and for 50 hours)

| Enzyme | Cyclodextrin Produced (%) | | |
|---|---|---|---|
|  | α | β | γ |
| Wild-type | 14 | 63 | 23 |
| Y89D | 17 | 63 | 20 |
| S146P | 26 | 55 | 19 |
| Y89D/S146P | 31 | 51 | 18 |

Example 3
Mutations in the E-domain of a Bacillus CGTase

This example describes the construction of two CGTase variants, holding mutations in the E domain cleft. The variants are derived from a *Bacillus circulans* Strain 251 CGTase (i.e. the wild-type enzyme), obtained as described by Lawson et al. [Lawson C L, van Montfort R, Strokopytov B, Rozeboom H J, Kalk K H, de Vries G E, Penninga D, Dijkhuizen L, and Dijkstra B W; *J. Mol. Biol.* 1994 236 590–600].

Two maltose binding sites (MBS) have been identified in the E domain and in this experiment it is found that these sites are of particular importance for the raw starch binding properties of the enzyme. The first site (MBS1) includes tryptophan at positions 616 and 662, which bind a maltose unit through van der Waals contacts of their indole groups with the glucose rings of the substrate. In the second site (MBS2), the in most cases conserved tyrosine at position 633, forms van der Waals contacts with a glucose residue of the substrate. Hydrogen bonds with surrounding residues enhance binding at these sites. MBS2 is located near the groove leading to the active site.

Mutations were introduced by a method based on two PCR reactions using VENT-DNA polymerase. For each mutation specific oligonucleotides were developed. The mutations were confirmed by restriction analysis and sequencing. Variants were obtained from an amylase and protease negative *Bacillus subtilis* strain and were purified using affinity chromatography.

Figure 3:
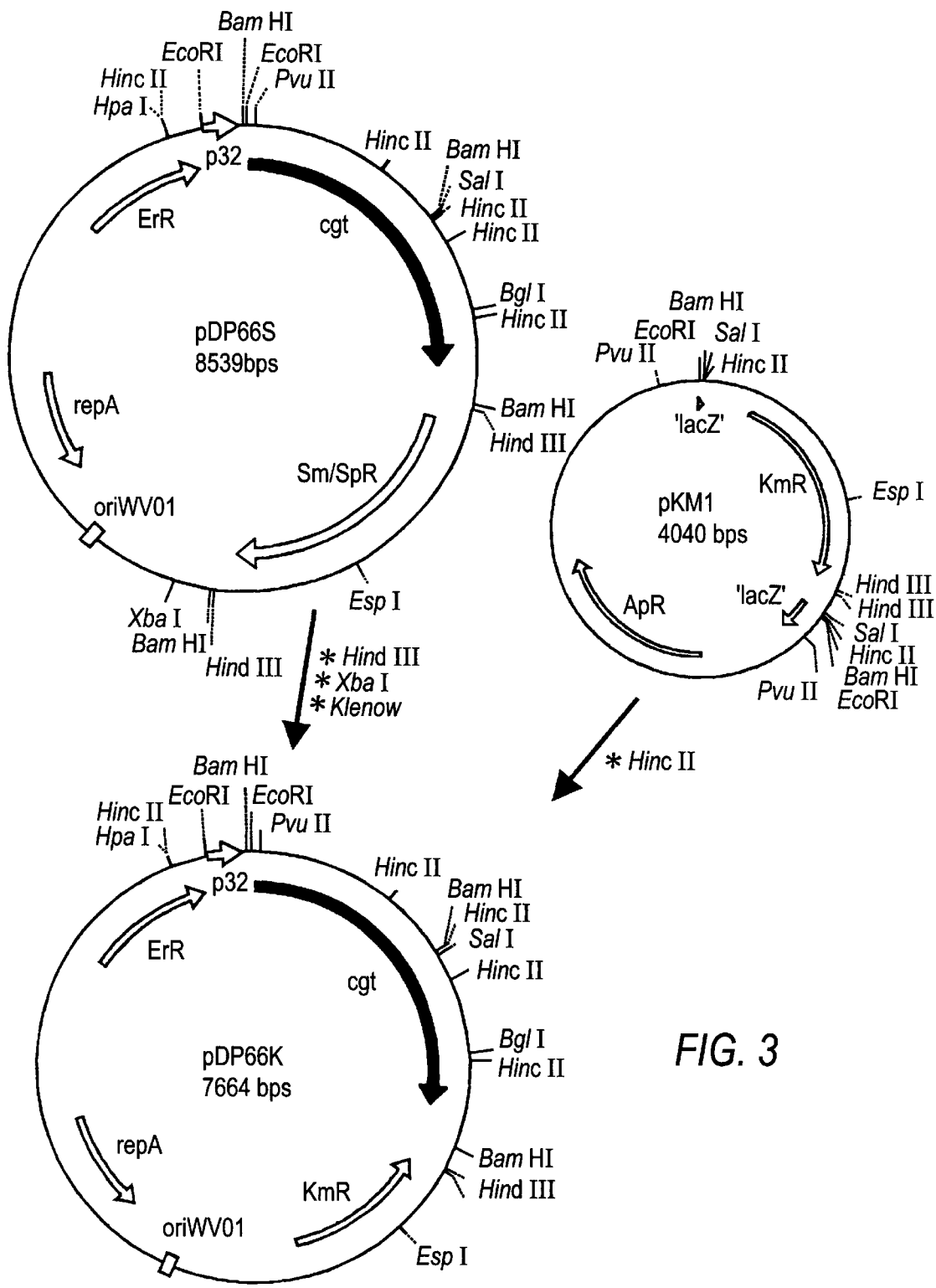
FIG. 3 shows the construction of plasmid pDP66K, subcloning steps are indicated adjacent to the arrows.

Bacterial Strains and Plasmids: *Escherichia coli* MC1061 [Meissner P S, Sisk W P, Berman M L; *Proc. Natl. Acad. Sci. USA* 1987 84 4171–4175] was used for recombinant DNA manipulations and site-directed mutagenesis. *E. coli* DH5α [Hanahan D; *J. Mol Biol.* 1983 166 557] was used for the production of monomeric supercoiled plasmid DNA for sequencing. CGTases variants were produced with the α-amylase and protease negative *Bacillus subtilis* Strain DB104A [Smith H, de Jong A, Bron S, Venema G; *Gene* 1988 70 351–361]. The fragment containing the kanamycin-resistance marker was ligated with the largest fragment from plasmid pDP66S [Penninga D, Strokopytov B, Rozeboom H J, Lawson C L, Dijkstra B W, Bergsma J, Dijkhuizen L; *Biochemistry* 1995 34 3368–3376] containing the *Bacillus circulans* CGTase gene, digested with HIndIII and XbaI (made blunt with Klenow polymerase). The resulting CGTase protein expression shuttle vector pDP66K, with the CGTase gene under control of the erthromycin-inducible p32 promotor [van der Vossen J M B M, Kodde J, Haandrikman A J, Venema G, Kok J; *Appl. Environ. Microbiol.* 1992 58 3142–3149], was transformed to *E. coli* MC1061 under selection for erythromycin and kanamycin resistance, cf. FIG. 3.

Construction of CGTase Variants: As only relatively low stability with plasmid pDP66S (8.5 kb) [Saenger W; *Angew. Chem.* 1980 19 344–362] was found, pDP66K (7.7 kb) was constructed, cf. FIG. 3, with the CGTase gene under the control of the strong p32 promotor [van der Vossen J M B M, Kodde J, Haandrikman A J, Venema G, Kok J; *Appl. Environ. Microbiol.* 1992 58 3142–3149]. Plasmid pDP66K containing the additional antibiotic resistance marker for kanamycin appeared to be considerably more stable in *E. coli* as well as in *B. subtilis* cells than plasmid pDP66S containing the streptomycin/spectinomycin resistance cassette. Using this shuttle vector, a high extracellular production of wild-type enzyme and CGTase variants was obtained reproducibly in batch fermentations with the α-amylase and protease negative *B. subtilis* Strain DB104A. A single 51 erlenmeyer flask with 11 *B. subtilis* Strain DB104A culture allowed purification to homogeneity of up to 25 mg of the CGTase variants. Mutations were constructed via site-directed (PCR) mutagenesis. Using specific oligonucleotide primers a mutation frequency close to 70% was observed. All mutations were confirmed by restriction analysis and DNA sequencing.

Growth Conditions: Plasmid carrying bacterial strains were grown on LB medium in presence of the antibiotics erythromycin and kanamycin, at concentrations of 100 and 5 µg/ml for *E. coli* and *Bacillus subtilis*, respectively [Sambrook et al., op cit]. When appropriate, agar plates contained 1% starch to screen for halo formation. *Bacillus subtilis* Strain DB 104A was grown in a 51 flask, containing 11 medium with 2% tryptone, 0.5% yeast extract, 1% sodium chloride and 1% casamino acids (pH 7.0) with 10 µg/ml erythromycin and 5 µg/ml kanamycin.

DNA Manipulations: Restriction endonucleases and Klenow enzyme were purchased from Pharmacia LKB Biotechnology, Sweden, and used according to the manufacturers instructions. DNA manipulations and calcium chloride transformation of *E. coli* strains were accomplished as described [Sambrook et al., op cit]. Transformation of *Bacillus subtilis* was performed as described by Bron [Harwood C R and Cutting S M, Eds.; *Modern Microbiological Methods for Bacillus*, 1990, Wiley & Sons, New York/Chichester; "Plasmids", pp. 146–147].

Site-directed Mutagenesis: To introduce mutations we used a method based on two PCR reactions using VENT-DNA polymerase (New-England Biolabs, Beverly, Mass., USA), in which a first PCR was carried out using a mutagenesis primer on the coding strand plus a primer 910–1050 bp downstream on the template strand. The product of this reaction (910–1050 bp) was subsequently used as primer in the second PCR together with a primer 760–900 bp upstream on the coding strand. The product of the last reaction (1800 bp) was cut with BglI and HindIII and exchanged with the corresponding fragment (600 bp) from the vector pDP66K. The resulting (mutant) plasmid was transformed to *E. coli* MC 1061 cells. The following oligonucleotides (primers) were used to produce the mutations:

| | |
|---|---|
| Y633A: | 5'-G GTC GTT TAC CA<u>G GCG CC</u>G AAC TGG-3' (SEQ ID NO: 13) |
| W616A: | 5'-GC <u>GAG CT</u>C GGG AAC GCG GAC CCG-3' (SEQ ID NO: 14) |
| W662A: | 5'-CC GTC A<u>CC GCG G</u>AA GGC GGC-3' (SEQ ID NO: 15) |

Successful mutagenesis resulted in the appearance of the underlined restriction sites, allowing rapid screening of potential mutations. For Y633A this restriction site was NarI, for W616A SacI, and for W662A SacII.

DNA Sequencing: Plasmid pDP66K carrying the right restriction site was transformed to *E. coli* DH5α cells. DNA sequence determination was performed on supercoiled plasmid DNA using the dideoxy-chain termination method [Sanger F, Coulson A R; *J. Mol Biol.* 1975 94 441–448] and the T7-sequencing kit from Pharmacia LKB Biotechnology, Sweden.

Production and Purification of CGTase Variants: Plasmid pDP66K, carrying positively characterized mutant CGtase genes, was transformed to *Bacillus subtilis* Strain DB104A. The organism was grown to an optical density of 4.5 determined at 600 nm in a 51 flask (for approx. 36 hours). Under these conditions high extracellular CGTase levels were produced. The culture was centrifuged (×10,000 g) at 4° C. for 30 minutes. The (mutant) CGTases were further purified to homogeneity by affinity chromatography using a 30 ML α-cyclodextrin-Sepharose-6FF column (Pharmacia, Sweden) [Sundberg L, Porath J; *J. Chromatogr.* 1974 90 87–98] with a maximal capacity of 3.5 mg protein per ml. After washing with 10 mM sodium acetate buffer (pH 5.5), bound CGTase was eluted with the same buffer containing 10 mg/ml α-cyclodextrin.

Enzyme Assays

β-cyclodextrin Forming Activity: β-cyclodextrin forming activity was determined using 5% Paselli™ SA2 (i.e. partially hydrolysed potato starch with an average degree of polymerization of 50, available from AVEBE, Foxhol, The Netherlands) as substrate and after incubation for 3 minutes at 50° C. 0.1–0.1 units of activity were used. The β-cyclodextrin formed was determined based on its ability to form a stable colorless inclusion complex with phenolphthalein. One unit of activity is defined as the amount of enzyme able to form 1 µmol of β-cyclodextrin per minute.

Raw Starch Binding Properties: Raw starch binding properties were studied by incubating 6 µg/ml of enzyme with increasing amounts (0–10%) of granular potato starch (Paselli™ SA2, available from AVEBE, Foxhol, The Netherlands) for 1 hour at 4° C., with and without 0.1 mM of β-cyclodextrin (equilibrium was reached within 10 minutes). After incubation, protein bound to the starch granules was spun down for 1 minute at 4° C. and at 10,000×g, and the remaining β-cyclodextrin forming activity of the supernatant was determined as described above.

Kinetic Studies: Kinetic studies on Paselli™ SA2 (AVEBE, Foxhol, The Netherlands) were performed by determination of the β-cyclodextrin forming activity of the enzyme on Paselli™ concentrations ranging from 0 to 5%, with and without addition of 0.1 or 0.2 mM of β-cyclodextrin. In these experiments approx. 0.6 μg/ml (0.15–0.18 units) of enzyme was used.

Kinetic Studies: Alternatively, kinetic studies on raw starch were performed by incubating 6 μg/ml of enzyme for 10 minutes with raw starch concentrations in the range of from 0 to 50%. β-cyclodextrin formation was determined as described above.

The data collected from these kinetic and binding studies were fitted using the Hill equation, yielding $Y_{max}$ and $K_{50}$ values for the binding studies, and $V_{max}$ and $K_{50}$ values for the kinetic studies. $K_i$ values were calculated as follows.

$$\text{For non-competitive inhibition: } K_i = \frac{[I]}{\frac{V_{max}}{V_{maxi}} - 1}$$

$$\text{For competitive inhibition: } K_i = \frac{[I]}{\frac{K_{50}}{K_{50}} - 1}$$

Results

Since maltose binding site 1 (MBS1) includes two tryptophan residues, the double mutation W616A/W662A was constructed. In this way we created comparable changes in the two binding sites, which were designed to completely remove the hydrophobic interactions of the aromatic residues with the glucose units of the substrate. The two separate CGTase variants, W616A and W662A, gave intermediate results compared to the double mutant, W616A/W662A.

Figure 4A:
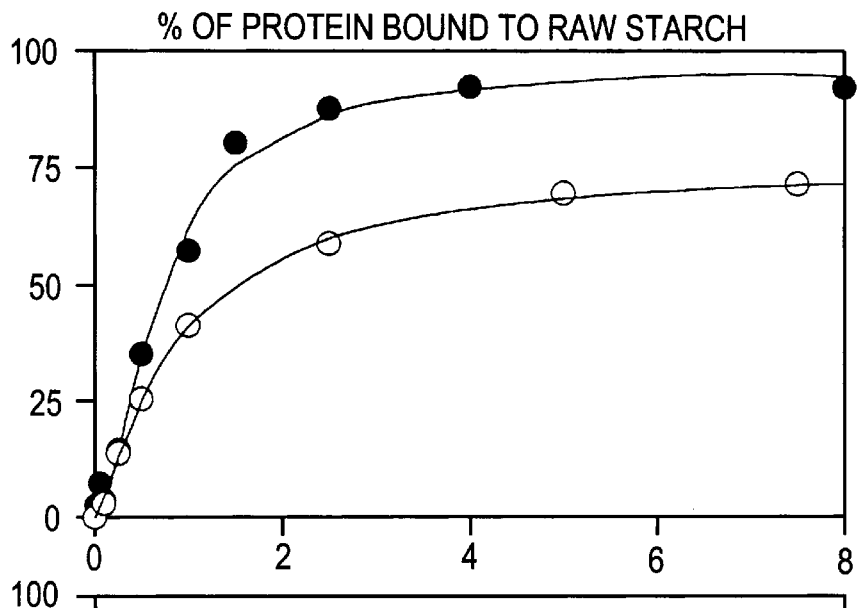
FIG. 4 shows the results of starch binding experiments (% of protein bound to raw starch) at starch concentrations of from 0 to 8% raw starch, (●) without β-cyclodextrin, and (○) with 0.1 mM β-cyclodextrin; (a) wild-type enzyme (*Bacillus circulans* Strain 251 CGTase), (b) the W616A/W662A variant, and (c) the Y633A variant.
Figure 4B:
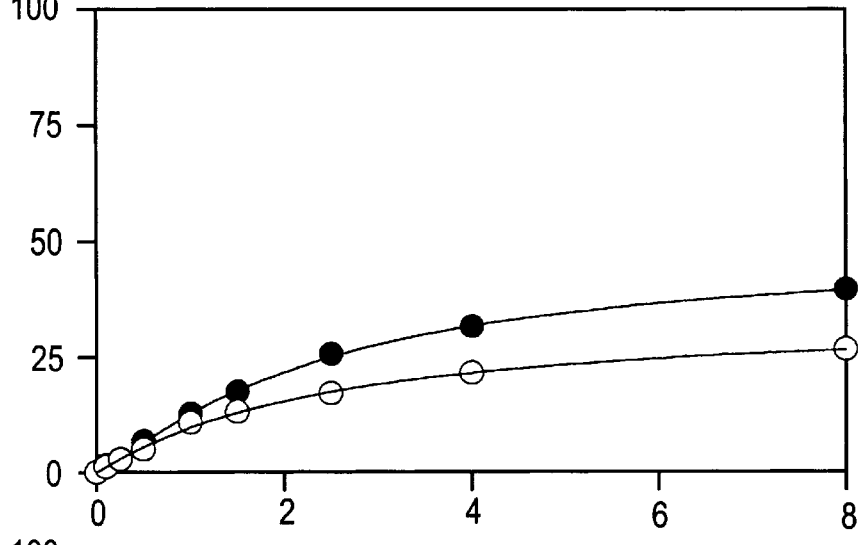
Figure 4C:
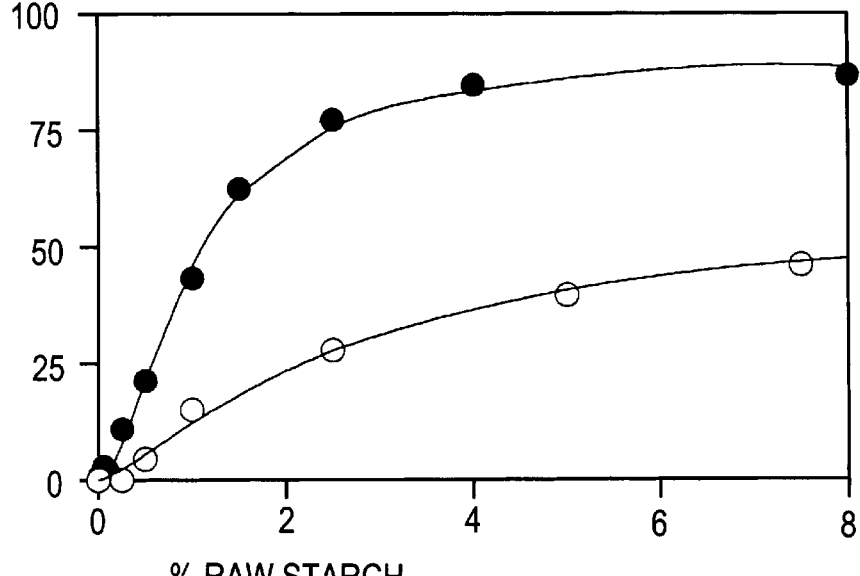
Figure 5A:
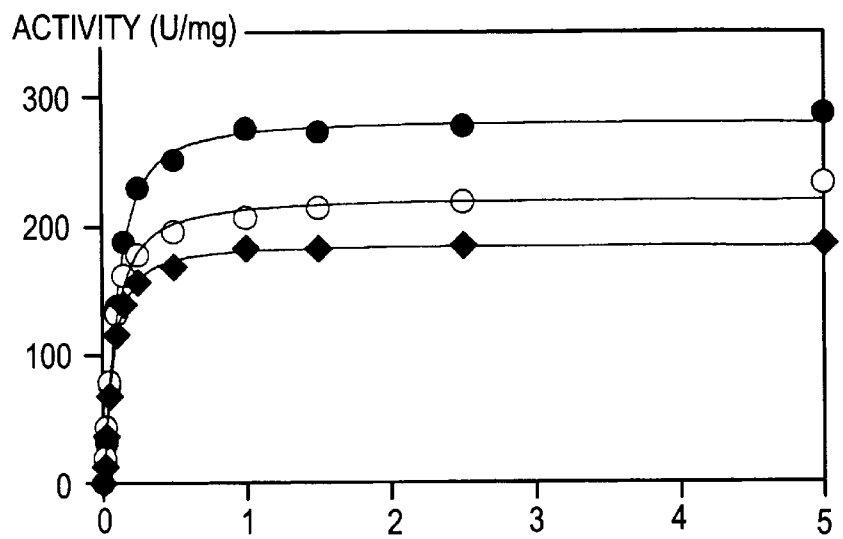
FIG. 5 shows the results of reaction kinetic experiments (activity, U/mg) on Paselli™ SA2 (i.e. partially hydrolysed potato starch) at concentrations of from 0 to 5% Paselli™, (●) without β-cyclodextrin, (○) with 0.1 mM β-cyclodextrin, and (♦) with 0.2 mM β-cyclodextrin; (a) wild-type enzyme (*Bacillus circulans* Strain 251 CGTase), (b) the W616A/W662A variant, and (c) the Y633A variant.
Figure 5B:
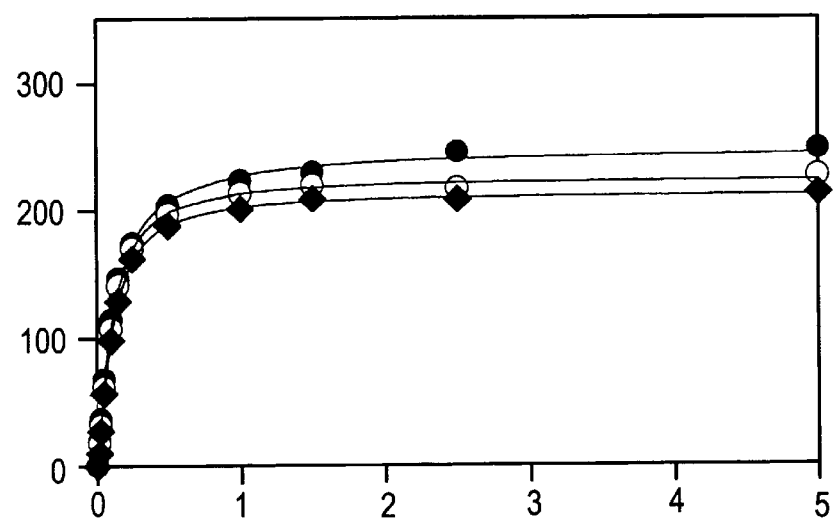
Figure 5C:
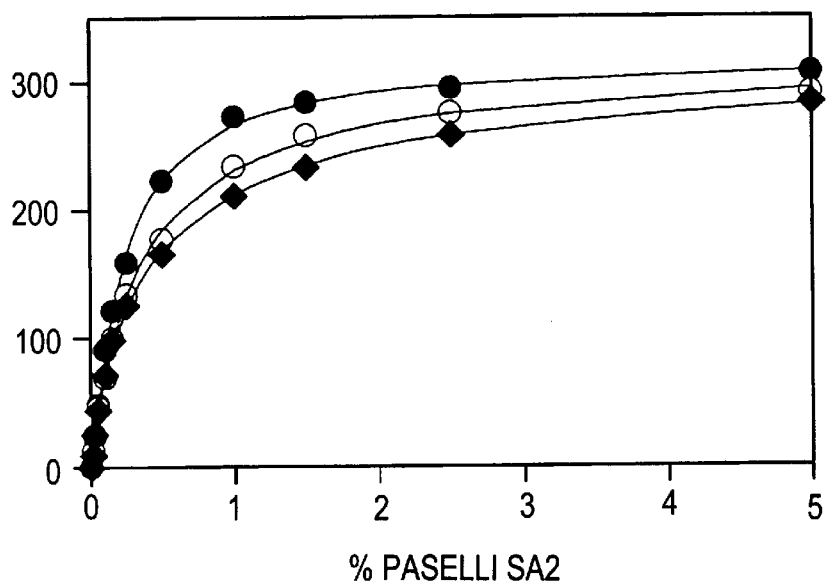
Figure 6:
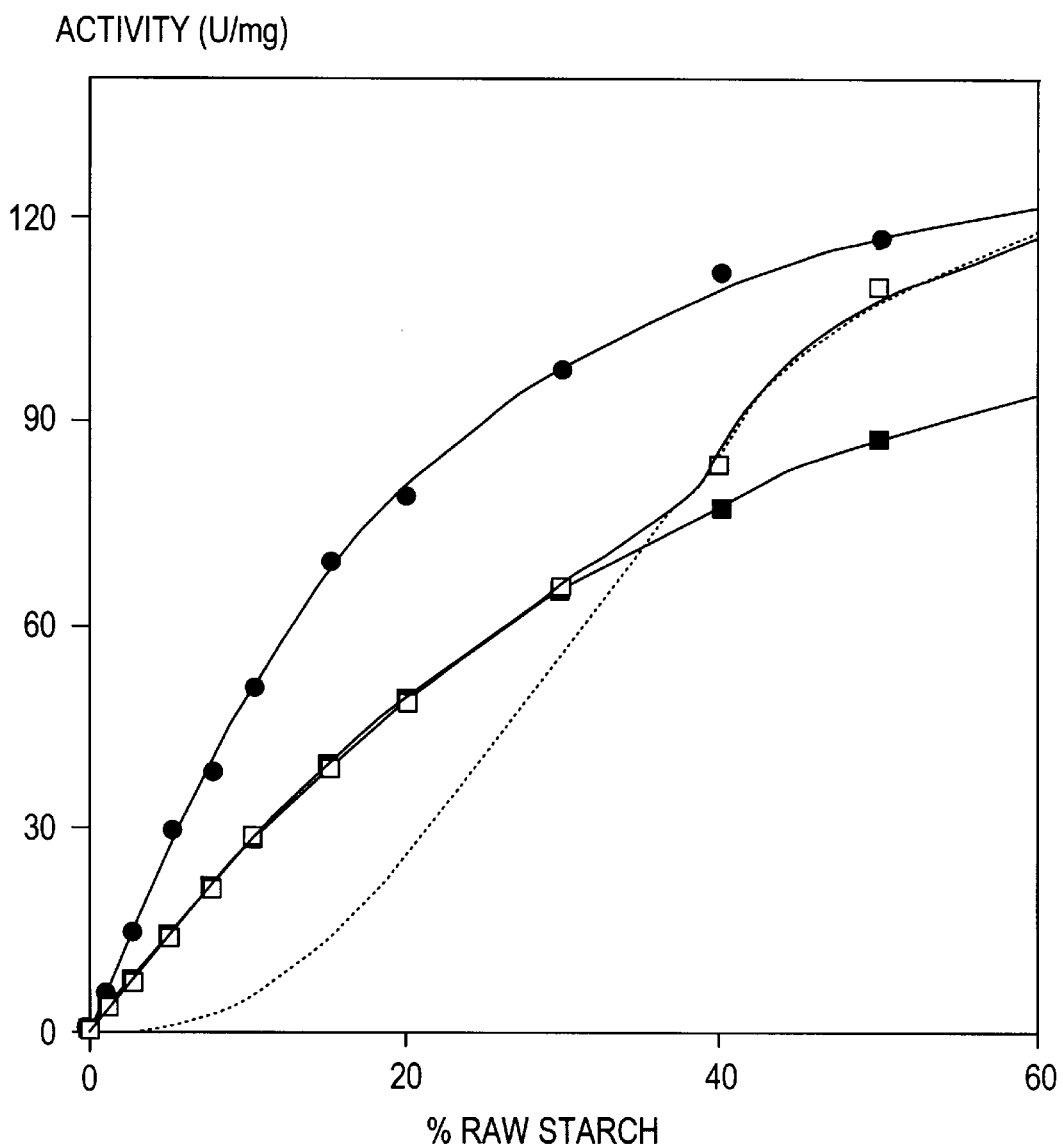
FIG. 6 shows the results of reaction kinetic experiments (activity, U/mg) on raw starch at starch concentration of from 0 to 60% raw starch, (●) wild-type enzyme (*Bacillus circulans* Strain 251 CGTase), (□) the W616A/W662A variant, and (■) the Y633A variant; the dotted line indicates the modelled curve resulting from the supposed interaction between MBS2 on the E domain and MBS3 on the C domain.

From the results presented in FIGS. 4–6, in which the curves are better fitted to a Hill equation than to a Michaelis-Menten equation, indicates that there is a form of cooperativity involved in the reaction and binding kinetics.

The results of the raw starch binding experiments are presented in Table 17 and FIG. 4. Determination of raw starch binding revealed a sharp decrease for the W616A/W662A variant, indicating that MBS1 is required and has the highest affinity for substrate binding. The Y633A variant shows only small decreases in affinity and $Y_{max}$, which suggests that MBS2 has only little contribution to raw starch binding.

The effect of β-cyclodextrin on raw starch binding indicates that it can inhibit the binding by competition with a starch chain for the binding sites of the enzyme. This effect is more pronounced for the variants produced as compared to the wild-type, indicating that when one MBS is deleted, competition of β-cyclodextrin with raw starch for the remaining site is stronger. This also indicates a form of cooperativity between MBS's.

The Hill factor "n", indicating the degree of cooperativity involved in raw starch binding is strongly decreased in the W616A/W662A variant, showing that MBS1 contributes highly to cooperative binding. The Y633A variant has the same "n" value as the wild-type enzyme. This suggests that sites other than MBS2 cooperate with MBS1 in binding.

The results of the reaction kinetics on hydrolysed potato starch (Paselli™ SA2) are presented in Table 18 and FIG. 5. These results show another role for MBS2 in the wild-type enzyme. The lower affinity for Paselli™ of the Y633A variant suggests that the substrate might be less efficiently guided to the active site in the absence of this binding site. This is also supported by the decrease of factor "n" to approx. 1, which shows that the cooperativity observed in reaction kinetics has been lost in this variant. The shift from non-competitive to competitive inhibition by β-cyclodextrin implies that MBS2 is responsible for the non-competitive product inhibition. The results with the W616A/W662A variant show that MBS1 is only slightly involved in degradation of Paselli™.

The results of the reaction kinetics on raw starch are presented in Table 19 and FIG. 6. These results show a high decrease in affinity when either of the MBS's are deleted, indicating that for activity on raw starch both MBS's are equally important. At high raw starch concentrations, however, the curve representing the W616A/W662A variant aligns to that of the wild-type enzyme, suggesting that a binding site other than MBS1 takes over its function. This site might be MBS3 on the C domain.

From these experiments it is concluded that the E domain with its binding sites is required for the conversion of raw starch into cyclodextrins. The enzyme binds to the raw starch granule via MBS1, while MBS2 guides the starch chain protruding from the granule to the active site.

TABLE 17

Binding Properties on Raw Starch

| Enzyme | $Y_{max}$ | | $K_{50}$ (% RS) | | n | |
|---|---|---|---|---|---|---|
| | 0 mM β-CD | 0.1 mM β-CD | 0 mM β-CD | 0.1 mM β-CD | 0 mM β-CD | 0.1 mM β-CD |
| Wild-type | 96.2 ± 3.3 | 76.4 ± 1.3 | 0.70 ± 0.05 | 0.89 ± 0.04 | 1.71 ± 0.19 | 1.25 ± 0.06 |
| W616A/W662A | 48.7 ± 1.3 | 33.4 ± 2.0 | 2.36 ± 0.13 | 2.27 ± 0.30 | 1.19 ± 0.06 | 1.07 ± 0.07 |
| Y633A | 90.8 ± 2.2 | 58.4 ± 5.9 | 0.99 ± 0.05 | 2.70 ± 0.58 | 1.73 ± 0.12 | 1.34 ± 0.20 |

TABLE 18

Kinetic Properties Determined on Paselli ™ SA2

| Enzyme | $V_{max}$ (units/mg) | | | $K_{50}$ (% Paselli ™ SA2) | | | n | $K_i$ (nM) |
|---|---|---|---|---|---|---|---|---|
| | 0 mM β-CD | 0.1 mM β-CD | 0.2 mM β-CD | 0 mM β-CD | 0.1 mM β-CD | 0.2 mM β-CD | | |
| Wild type | 280.4 ±2.6 | 221.0 ±3.7 | 184.5 ±1.6 | 0.098 ±0.003 | 0.077 ±0.005 | 0.071 ±0.002 | 1.40 ±0.12 | 0.38 ±0.02 |
| W616A/W662A | 247.2 ±3.0 | 224.5 ±1.6 | 212.6 ±1.2 | 0.115 ±0.005 | 0.104 ±0.002 | 0.109 ±0.002 | 1.26 ±0.12 | 1.11 ±0.14 |
| Y633A | 316.2 ±3.6 | 316.5 ±6.1 | 317.2 ±5.5 | 0.23 ±0.01 | 0.35 ±0.02 | 0.44 ±0.03 | 0.98 ±0.15 | 0.21 ±0.04 |

TABLE 19

Kinetic Properties Determined on Raw Starch

| Enzyme | $V_{max}$ (units/mg) | $K_{50}$ (% RS) |
|---|---|---|
| Wild-type | 153.1 ± 4.8 | 18.4 ± 1.3 |
| W616A/W662A | (153.1) | (42.5) |
| Y633A | 159.5 ± 5.0 | 42.5 ± 2.7 |

Example 4
Construction of β-and γ-cyclodextrin Producing CGTase Variants from Bacillus This example describes the construction of several β-and γ-cyclodextrin producing CGTase variants, in which site directed mutagenesis has lead to an altered number of hydrogen bonds in the active site cleft. The variants are derived from a *Bacillus circulans* Strain 251 CGTase (i.e. the wild-type enzyme), obtained as described by Lawson et al. [Lawson C L, van MOntfort R, Strokopytov B, Rozeboom H J, Kalk K H, de Vries G E, Penninga D, Dijkhuizen L and Dijkstra B W; *J. Mol Biol.* 1994 236 590–600].

Mutations were introduced with a PCR method using VENT-DNA polymerase (New-England Biolabs, Beverly, Mass., USA). A first PCR reaction was carried out with a mutagenesis primer for the coding strand, plus a primer downstream on the template strand. The reaction product was subsequently used as primer in a second PCR reaction together with a primer upstream on the coding strand. The product of the last reaction was cut with PvuII and SalI and exchanged with the corresponding fragment (1200 bp) from the vector pDP66K (cf. FIG. 3). The resulting (mutant) plasmid was transformed to *E. coli* MC1061 cells [Meissner P S, Sisk W P, Berman M L; *Proc. Natl. Acad. Sci. USA* 1987 84 4171–4175].

The following oligonucleotides (primers) were used to produce the mutations:

N193G:   5'-GC ATC TAC AAG GGC CTG TACGAT CTC G-3'           (Dra II) (SEQ ID NO: 16);

Y89G:    5'-GCA TCA TCA ATG GAT CCG GCG TAA AC-3'            (Bam HI) (SEQ ID NO: 17);

*145aI:  5'-CAT ACG TCG CCC GCT AGC ATT TCC GAC CAG CCT TCC-3'  (Nhe I) (SEQ ID NO: 18);

D371G:   5'-CG GGC GGG ACC GGT CCG GAC AAC CG-3'              (Pin AI) (SEQ ID NO: 19);

D371N:   5'-G TCG GGC GGT ACC AAT CCG GAC AAC C-3'            (Kpn I) (SEQ ID NO: 20); and N326Q:   5'-CG TTC ATC GAT CAG CAT GAC ATG G-3'               (Cla I) (SEQ ID NO: 21).

Successful mutagenesis resulted in appearance of the underlined restriction sites, allowing rapid screening of potential mutants.

Plasmid pDP66K carrying the right restriction site was transformed to *E. coli* DH5αcells [Hanahan D; *J. Mol Biol.* 1983 166 557]. DNA sequence determination was performed on supercoiled plasmid DNA using the dideoxy-chain termination method [Sanger F, Coulson A R; *J. Mol Biol.* 1975 94 441–448] and the T7-sequencing kit from Pharmacia-LKB Biotechnology, Sweden.

Plasmid pDP66K, carrying positively characterized mutant cgt genes, was transformed to *B. subtilis* strain DB104A [Smith H, de Jong A, Bron S, Venema G; *Gene* 1988 70 351–361]. The organism was grown to an optical density at 600 nm of 4.5 in a 51 flask (for approx. 36 hours). Under these conditions high extracellular CGTase levels were produced.

The culture was centrifuged at 4° C. for 30 minutes at 10,000×g. The CGTases variant in the culture supernatants were further purified to homogeneity by affinity chromatography, using a 30 ml α-cyclodextrin-Sepharose-6FF column (Pharmacia, Sweden) [Sundberg L, Porath J; *J. Chromatogr.* 1974 90 87–98] with a maximal capacity of 3.5 mg protein per ml. After washing with 10 mM sodium acetate buffer (pH 5.5), bound CGTase was eluted with the same buffer containing 10 mg/ml α-cyclodextrin.

β-cyclodextrin forming activity was determined by incubating an appropriately diluted enzyme sample (0.1–0.2 units of activity) for 3 minutes at 50° C. Paselli™ SA2 (5% solution partially hydrolysed potato starch with an average degree of polymerization of 50 (AVEBE, Foxhol, The Netherlands), was used as a substrate. The β-cyclodextrin formed was determined based on its ability to form a stable colorless inclusion complex with phenolphthalein. One unit of activity is defined as the amount of enzyme able to produce 1 μmol of β-cyclodextrin per minute.

Cyclodextrin forming activity was also measured under production process conditions. For this purpose 0.1 U/ml CGTase was incubated with 10% Paselli™ WA4 (i.e. jet-cooked, pregelatinized drum-dried starch) in a 10 mM sodium citrate buffer (pH 6.0) at 50° C. for 45 hours. Samples were collected at regular time intervals, diluted 10 times, boiled for 8 min. and the products formed analyzed by HPLC using a 25 cm Econosphere-NH$_2$ 5 micron column (Alltech Associates Inc., USA) eluted with acetonitrile/water (60/40 v/v) at 1 ml per min.

Results

The variants of this example were designed in order to increase β-and γ-cyclodextrin formation. The N193G, Y89G, D371G, D371N and the Y89G/N193G CGTase variants were all designed with the intention to decrease the interactions between the amylose chain and the first part of the active site cleft (Subsites C-G). As a result, the amylose chain would be able to move further into the active site cleft, thereby changing the ratio of cyclodextrins towards the β-and γ-cyclodextrins.

The N193G CGTase variant demonstrates a rapid increase in β-cyclodextrin (FIGS. 7 and 9). As a result, the ratio is changed already dramatically after 5 hours of incubation (Table 20) towards α-and β-cyclodextrin. However, after 45 hours (Table 21) the ratio has changed towards α-cyclodextrin formation only. This mutation seems particularly well suited for combination with other mutations, e.g. D371G or D371N.

The Y89G CGTase variant results in a small change towards β-cyclodextrin after 45 hours of incubation at the expense of α-cyclodextrin (cf. FIG. 7 and Table 21).

Figures 8A, 8B, 8C:
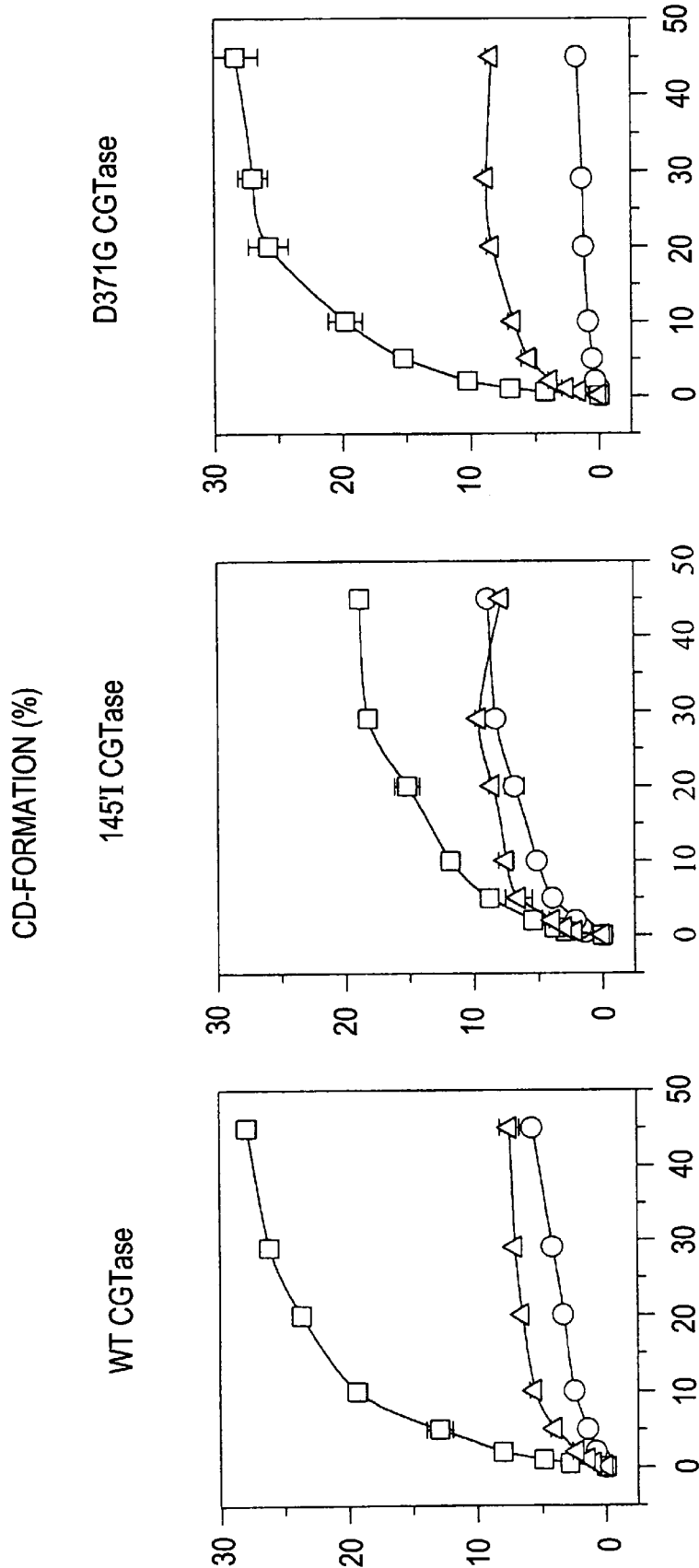
FIG. 8 shows the product formation (○ α-cyclodextrin formation; □ β-cyclodextrin formation, and Δ γ-cyclodextrin formation) of two CGTase variants of the invention (*145aI, FIG. 8B, and D371G, FIG. 8C) compared to the wild-type enzyme (from *Bacillus circulans* Strain 251, FIG. 8A) during incubation for 0 to 45 hours.

The D371N and D371G CGTase variants both show a shift towards formation of the larger cyclodextrins (cf. FIG. 8 and Table 21). Both β-and γ-cyclodextrin increased at the expense of α-cyclodextrin. This shift is more pronounced at early incubation times (cf. Table 20 and FIG. 10).

The Y89G/N193G CGTase double mutant resulted in a shift from β-cyclodextrin to both α-and γ-cyclodextrin (cf.

Table 21). In combination with other mutations, in particular D371G or D371N, this mutation could give rise to a single shift to β-cyclodextrin.

The *145aI CGTase variant was constructed on the basis of alignment studies. This insertion mutation seems especially advantageous for obtaining β-cyclodextrin producing CGTase variants. Both short incubation times (cf. FIG. 10 and Table 20) and long incubation times (cf. FIG. 8 and Table 21) gave a shift from β-cyclodextrin to both α-and γ-cyclodextrin. Also, in order to obtain a single shift to β-cyclodextrin, this mutation seems particularly well suited for combination with other mutations, e.g. D371G or D371N.

The N326Q CGTase variant was constructed and shown to cause a shift from α-cyclodextrin to β- and γ-cyclodextrin formation (cf. Table 21).

Finally, combinations of the above mutations seems straightforward in order to obtain CGTase variants with increased β- and/or γ-cyclodextrin formation.

TABLE 20

Ratio of Cyclodextrin Formation from 10% Paselli ™ WA4 (at 50° C. for 5 hours)

| Enzyme | Cyclodextrins Produced (%) | | |
|---|---|---|---|
| | α | β | γ |
| Wild-type | 7.4 ± 1.4 | 70.8 ± 1.8 | 21.8 ± 0.5 |
| N193G | 13.5 ± 0.2 | 57.5 ± 0.7 | 29.0 ± 0.8 |
| Y89G | 9.5 ± 1.2 | 72.4 ± 2.1 | 18.0 ± 1.0 |
| *145aI | 18.8 ± 1.2 | 46.3 ± 1.3 | 34.3 ± 1.5 |
| D371G | 2.4 ± 0.2 | 71.8 ± 1.6 | 25.9 ± 1.4 |

TABLE 21

Ratio of Cyclodextrin Formation from 10% Paselli ™ WA4 (at 50° C. for 45 hours)

| Enzyme | Cyclodextrins Produced (%) | | |
|---|---|---|---|
| | α | β | γ |
| Wild-type | 14.4 ± 1.0 | 67.7 ± 0.7 | 18.0 ± 0.8 |
| N193G | 25.5 ± 0.1 | 60.4 ± 0.2 | 14.1 ± 0.4 |
| Y89G | 12.7 ± 0.3 | 69.3 ± 0.6 | 18.0 ± 0.3 |
| *145aI | 24.6 ± 0.5 | 53.5 ± 0.8 | 21.9 ± 0.7 |
| D371G | 4.4 ± 0.1 | 73.9 ± 0.1 | 21.7 ± 0.1 |
| D371N | 6.5 ± 0.5 | 73.4 ± 0.5 | 20.1 ± 0.4 |
| N326Q | 5.0 ± 0.1 | 75.4 ± 0.1 | 19.6 ± 0.2 |
| Y89G/N193G | 18.8 ± 0.6 | 53.8 ± 0.7 | 27.4 ± 0.3 |
| N193G/Q148E | 17.5 ± 0.5 | 60.9 ± 0.7 | 21.6 ± 0.8 |

TABLE 22

Specific Activities of Initial Cyclization

| Enzyme | Cyclization Activity (U/mg) | | |
|---|---|---|---|
| | α | β | γ |
| Wild-type | 2 | 280 | 53 |
| *145aI | | 111 | 59 |
| N193G | | 132 | 66 |
| N326Q | 3 | 63 | 14 |
| D371N | 25 | 108 | 30 |
| D371G | 7 | 81 | 29 |

Example 5

Construction of α-cyclodextrin Producing CGTase Variants from Thermoanaerobacter This example describes the construction of 24 α-cyclodextrin producing CGTase variants (A1–A24), in which site-directed mutagenesis either has lead to an altered number of hydrogen bonds in the subsites of the active cleft or, alternatively, to sterical hindrance in parts of the substrate binding left.

The variants are derived from a Thermoanaerobacter sp. CGTase obtained according to WO 89/03421, and having the nucleotide and amino acid sequences presented as SEQ ID NOS:1–2 (i.e. the wild-type enzyme).

Mutations were introduced by a method based on PCR by the use of PWO polymerase. For each mutation, specific oligonucleotides (primers) were developed. The mutations were confirmed by restriction analysis whenever possible, and by sequencing. Mutant proteins were expressed in either *Escherichia coli* MC1061 [Meissner P S, Sisk W P, Berman M L; *Proc. Natl. Acad. Sci. USA* 1987 84 4171–4175], or in the α-amylase and protease negative *Bacillus subtilis* Strain DB104A [Smith H, de Jong A, Bron S, Venema G; Gene 1988 70 351–361]. Proteins were purified from the media using affinity chromatography (AfC) and/or anion-exchange chromatography (AEC).

Enzyme Assays

Enzymatic activity was measured by a slightly modified procedure of the Phadebas amylase test (Pharmacia). Phadebas tablets (Phadebas™ Amylase Test, Pharmacia) are used as substrate. This substrate is a cross-linked insoluble blue-colored starch polymer, which is mixed with bovine serum albumin and a buffer substance. After suspension in water, starch is hydrolyzed by the enzyme, thereby yielding blue fragments. The determination is carried out after incubation at 60° C., pH 6.2, in 0.15 nM calcium for 15 minutes. The absorbance of the resulting blue solution, determined at 620 nm, corresponds the enzymatic activity.

The enzyme activity is compared to that of an enzyme standard, and the activity is expressed in the same unit as that of the enzyme standard. The enzyme standard was Termamyl™ (Novo Nordisk A/D, Denmark), the amylolytic activity of which has been be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alfa Amylase Unit (KNU) is defined as the amount of enzyme which, under standard conditions (i.e. at 37° C. +/−0.05; 0.0003 M $Ca^{2+}$; and pH 5.6) dextrinizes 5.26 g starch dry substance Merck Amylum solubile. Below the activity is expressed in Novo Units (NU) per ml.

CGTase activity was determined by incubating diluted enzyme with substrate in 10 mM sodium citrate, pH 6.0 for 4–10 minutes at 60° C.

Cyclodextrin forming activity was determined using 5% Paselli™ SA2 (i.e. partially hydrolysed potato starch with an average degree of polymerization of 50, available from AVEBE, Foxhol, The Netherlands) as substrate. The α-cyclodextrin formed was determined with Methyl-orange, the β-cyclodextrin formed was determined with phenolphthalein, and the γ-cyclodextrin formed was determined with bromo cresol green. The activity is expressed in units per mg (U/mg). One unit of enzyme activity is defined as the amount of enzyme able to produce one μmol of the specific cyclodextrin per minute.

Cyclodextrin formation was also determined under conventional industrial production process conditions. A precooked 10% amylopectin solution in 0.5 mM CaCl$_2$ at pH 5.5 was incubated with 50 NU of CGTase per gram of substrate, at 60° C. and for 24 hours. Samples are regularly withdrawn and boiled for 10 minutes at a pH of 2.5–3 prior to analysis by HPLC.

The results of these experiments are discussed and presented in tables 23–25, below. In Table 25, the figures are the ratio at maximum total level of cyclodextrin.

Oligonucleotide Primers

The following oligonucleotides were synthesized in order to initiate the site-directed mutagenesis (the numbers indicate positions according to the CGTase numbering):

```
A1: 143-151(GRAGTNPG) (SEQ ID NO: 12);
    5'-AATCATACATCTGGACGAGCAGGTACCAACCCGACTTTGGGGAAAA
    TGGTAC-3'                                           (SEQ ID NO: 23);
A2: 87-94(IKYSG-VNN) (SEQ ID NO: 11) + 143-151
    (GRAGTNPG) (SEQ ID NO: 12);
```

Using the B9 variant (87–94(IKYSG-VNN) (SEQ ID NO:11), described in Example 6 below, as starting point, the 143–151(GRAGTNPG) (SEQ ID NO:12) mutations was introduced using the A1 primer;

A3: F195Y+143–151(GRAGTNPG) (SEQ ID NO:12);

5'-TTACCGTAATTTATATGACTTAGCAG-3' (SEQ ID NO:67) was used to introduce the F195Y mutation and using this variant as starting point, the 87–94(IKYSG-VNN) (SEQ ID NO:11) mutations was introduced using the A1 primer;

A4: F195Y+87–94(IKYSG-VNN) (SEQ ID NO:11)+ 143–151(GRAGTNPG) (SEQ ID NO:12);

The Spe I—Bst X I fragment of A2 was ligated into the CGTase gene holding the F195Y mutation. The F195Y was introduced by the use of the A3 primer;

NO:59) mutations were introduced using the primer 5'-CTCCTGCATCATCTGATCAACCGTCCTTTGGGGA AAATGG-3' (SEQ ID NO:52);

```
A5: P143G-A144R-S145W;

5'-ATCATACATCCGGACGATGGGAGACAGACCCTACC-3' (SEQ ID NO:24);

A6: 87-94 (INDSG-VNN) (SEQ ID NO:58);

5'-CATTTACGCAGTTATCAATGATTCCGGAGTTAACAATACATCCTATCATGG-3' (SEQ ID NO:25);

A7: 87-94 (INDSG-VNN) (SEQ ID NO:58) + 146-150 (SDQPS) (SEQ ID NO:59);
```

Using the A6 variant (87–94(INDSG-VNN)) (SEQ ID NO:58) as starting point, the 146–150(SDQPS) (SEQ ID

```
A8:   143-148 (GRGPAA) (SEQ ID NO:10);

5'-CAAATCATACATCTGGACGAGGACCGGCCGCACCTACCTATGGGG-3' (SEQ ID NO:26);

A9:   143-148 (GRAPAA) (SEQ ID NO:9);

5'-CAAATCATACATCTGGACGAGCACCGGCCGCACCTACCTATGGGG-3' (SEQ ID NO:27);

A10:  143-148 (GRA**A) (SEQ ID NO:7);

5'-CAAATCATACATCTGGACGAGCAGCACCTACCTATGGGG-3' (SEQ ID NO:28);

A11:  143-148 (GRPAAA) (SEQ ID NO:64);

5'-CAAATCATACATCTGGACGACCTGCAGCAGCTCCTACCTATGGGG-3' (SEQ ID NO:29);

A12:  G180S;
```

```
     5'-CCATCATTACGGATCCACTAATTTTTCATC-3' (SEQ ID NO:30);

A13: A144R;

5'-CATACATCTCCTCGATCGGAGACAGACCC-3' (SEQ ID NO:31);

A14: P143A-A144R;

5'-CATACATCTGCTCGATCGGAGACAGACCC-3' (SEQ ID NO:32);

A15: G180N;

5'-CCATCATTACGGAAACACTAATTTTTCATC-3' (SEQ ID NO:33);

A16: G180D;

5'-CCATCATTACGGAGACACTAATTTTTCATC-3' (SEQ ID NO:34);

A17: G180N + P143G-A144R-S145W;
```

Using the A5 variant (P143G-A144R-S145W) as starting point, the G180N mutation was introduced using the primer 5'-CCATCATTACGGAAACACTAATTTTTCATC-3' (SEQ ID NO:33);
A18: G180D+P143G-A144R-S145W;
Using the A5 variant (P143G-A144R-S145W) as starting point, the G180D mutation was introduced using the primer 5'-CCATCATTACGGAGACACTAATTTTTCATC-3' (SEQ ID NO:34);

In experiment A2, the loop at positions 87 to 94 was replaced by (IKYSG*VNN (SEQ ID NO:11)), and simultaneously the loop at positions 143 to 151 was replaced by (GRAGTNPG (SEQ ID NO:12)) in order to increase the interactions between the enzyme and glucose units E, F and H, and in order to decrease the interactions between the enzyme and glucose units I and J (cf. FIG. 1). The initial rate of both β-CD formation and of γ-CD formation has decreased.

```
A19:  G179N;

5'-CCATCATTATAATGGAACTAATTTTTCATC-3' (SEQ ID NO:35);

A20:  G179S;

5'-CCATCATTATAGTGGAACTAATTTTTCATC-3' (SEQ ID NO:36);

A21:  G179D;

5'-CCATCATTATGATGGAACTAATTTTTCATC-3' (SEQ ID NO:37);

A22:  G179N + P143G-A144R-S145W;
```

Using the A5 variant (P143G-A144R-S145W) as starting point, the G179N mutation was introduced using the primer 5'-CCATCATTATAATGGAACTAATTTTTCATC-3' (SEQ ID NO:35);
A23: G179S+P143G-A144R-S145W;
Using the A5 variant (P143G-A144R-S145W) as starting point, the G179S mutation was introduced using the primer 5'-CCATCATTATAGTGGAACTAATTTTTCATC-3'(SEQ ID NO:36); and
A24: G179D+P143G-A144R-S145W;
Using the A5 variant (P143G-A144R-S145W) as starting point, the G179D mutation was introduced using the primer 5'-CCATCATTATGATGGAACTAATTTTTCATC-3'(SEQ ID NO:37).
Results The variants of this example were designed in order to increase α-cyclodextrin formation.

In experiment A1, the loop at positions 143 to 151 was replaced by (GRAGTNPG (SEQ ID NO:12)) in order to increase the interactions between the enzyme and glucose unit H, and in order to decrease the interactions between the enzyme and glucose units I and J (cf. FIG. 1). The initial rate of both β-CD formation and of γ-CD formation has decreased. In the CD-production assay, the ratio of α-CD has increased, whereas the β-CD ratio has decreased.

In experiment A3, the loop at positions 143 to 151 was replaced by (GRAGTNPG (SEQ ID NO:12)) in order to increase the interactions between the enzyme and glucose unit H, and in order to decrease the interactions between the enzyme and glucose units I and J (cf. FIG. 1). Simultaneously, the F195 was replaced by 195Y in order to decrease the contact between enzyme and substrate. The initial rate of both β-CD formation and of γ-CD formation has decreased. In the CD-production assay, the ratio of α-CD has increased whereas the β-CD ratio has decreased.

In experiment A4, the loop at positions 87–94 was replaced by (IKYSG*VNN (SEQ ID NO:11)), and simultaneously the loop at positions 143 to 151 was replaced by (GRAGTNPG (SEQ ID NO:12)) in order to increase the interactions between the enzyme and glucose units E, F and H, and in order to decrease the interactions between the enzyme and glucose units I and J (cf. FIG. 1). Simultaneously, the F195 was replaced by 195Y in order to decrease the contact between enzyme and substrate. The initial rate of β-CD formation has decreased. In the CD-production assay, the β-CD ratio has decreased.

In experiment A5, the region at positions 143 to 145 was replaced by (GRW) in order to increase the interactions between the enzyme and glucose unit H, and in order to decrease the interactions between the enzyme and glucose units I and J by making a sterical hindrance (cf. FIG. 1). The initial rate of α-CD formation has increased, whereas the initial rate of both β-CD formation and of γ-CD formation has decreased. In the CD-production assay, the ratio of α-CD has increased whereas the β-CD ratio has decreased.

In experiment A6, the loop at positions 87–94 was replaced by (IKDSG*VNN (SEQ ID NO:66)) in order to increase the interactions between the enzyme and glucose units E and F (cf. FIG. 1).

In experiment A7, the loop at positions 87–94 was replaced by (IKDSG*VNN (SEQ ID NO:66)), and simultaneously the loop at positions 146 to 150 was replaced by (SDQPS (SEQ ID NO:59)) in order to increase the interactions between the enzyme and glucose units E and F, and in order to decrease the interactions between the enzyme and glucose units I and J (cf. FIG. 1).

In experiment A8, the loop at positions 143 to 148 was replaced by (GRGPAA (SEQ ID NO:10)) in order to increase the interactions between the enzyme and glucose unit H, and in order to decrease the interactions between the enzyme and glucose units I and J (cf. FIG. 1).

In experiment A9, the loop at positions 143 to 148 was replaced by (GRAPAA (SEQ ID NO:9)) in order to increase the interactions between the enzyme and glucose unit H, and in order to decrease the interactions between the enzyme and glucose units I and J (cf. FIG. 1).

In experiment A10, the loop at positions 143 to 148 was replaced by (GRA**A (SEQ ID NO:7)) in order to increase the interactions between the enzyme and glucose unit H, and in order to decrease the interactions between the enzyme and glucose units I and J (cf. FIG. 1).

In experiment A11, the region at positions 143 to 148 was replaced by (GRW) in order to increase the interactions between the enzyme and glucose unit H, and in order to decrease the interactions between the enzyme and glucose units I and J (cf. FIG. 1). The initial rate of both β-CD formation and of γ-CD formation has decreased more significantly than the initial rate of α-CD formation, which results in an increased ration between α-cd formation and β-CD formation.

In experiment A12, G180 was replaced by 180S in order to increase the interactions between the enzyme and glucose unit H (cf. FIG. 1).

In experiment A13, A144 was replaced by 144R in order to increase the interactions between the enzyme and glucose unit H (cf. FIG. 1).

In experiment A14, P143-A144 was replaced by 143A-144R in order to increase the interactions between the enzyme and glucose unit H (cf. FIG. 1).

In experiment A15, G180 was replaced by 180N in order to increase the interactions between the enzyme and glucose unit H (cf. FIG. 1).

In experiment A16, G180 was replaced by 180D in order to increase the interactions between the enzyme and glucose unit H (cf. FIG. 1).

In experiment A17, G180 was replaced by 180N in order to increase the interactions between the enzyme and glucose unit H (cf. FIG. 1). Simultaneously, the region at positions 143 to 145 was replaced by (GRW) in order to increase the interactions between the enzyme and glucose unit H, and in order to decrease the interactions between the enzyme and glucose units I and J by making a sterical hindrance (cf. FIG. 1).

In experiment A18, G180 was replaced by 180D in order to increase the interactions between the enzyme and glucose unit H (cf. FIG. 1). Simultaneously, the region at positions 143 to 145 was replaced by (GRW) in order to increase the interactions between the enzyme and glucose unit H, and in order to decrease the interactions between the enzyme and glucose units I and J by making a sterical hindrance (cf. FIG. 1).

In experiment A19, G179 was replaced by 179N in order to increase the interactions between the enzyme and glucose unit H (cf. FIG. 1).

In experiment A20, G179 was replaced by 179S in order to increase the interactions between the enzyme and glucose unit H (cf. FIG. 1).

In experiment A21, G179 was replaced by 179D in order to increase the interactions between the enzyme and glucose unit H (cf. FIG. 1).

In experiment A22, G179 was replaced by 179N in order to increase the interactions between the enzyme and glucose unit H (cf. FIG. 1). Simultaneously, the region at positions 143 to 145 was replaced by (GRW) in order to increase the interactions between the enzyme and glucose unit H, and in order to decrease the interactions between the enzyme and glucose units I and J by making a sterical hindrance (cf. FIG. 1).

In experiment ABBE, G179 was replaced by 179S in order to increase the interactions between the enzyme and glucose unit H (cf. FIG. 1). Simultaneously, the region at positions 143 to 145 was replaced by (GRW) in order to increase the interactions between the enzyme and glucose unit H, and in order to decrease the interactions between the enzyme and glucose units I and J by making a sterical hindrance (cf. FIG. 1).

In experiment A24, G179 was replaced by 179D in order to increase the interactions between the enzyme and glucose unit H (cf. FIG. 1). Simultaneously, the region at positions 143 to 145 was replaced by (GRW) in order to increase the interactions between the enzyme and glucose unit H, and in order to decrease the interactions between the enzyme and glucose units I and J by making a sterical hindrance (cf. FIG. 1).

TABLE 23

Production, Purification and Enzyme Activities of CGTases

| Enzyme | Host | Purification method | Enzyme activity (NU/mg) |
|---|---|---|---|
| Wild-type | E. coli | AfC | 1513 |
| A1 | E. coli | AfC | 432 |
| A2 | E. coli | AfC | 1009 |
| A | E. coli | AfC | 1404 |
| A4 | E. coli | AfC | 1082 |
| A5 | E. coli | AfC + AEC | 2100 |
| A9 | E. coli | | |
| A10 | E. coli | | |
| A11 | E. coli | AfC + AEC | 2200 |

TABLE 24

Specific Activities of α-, β- and γ-CD Forming CGTases

| | Cyclization Activity (U/mg) | | |
|---|---|---|---|
| Enzyme | α | β | γ |
| Wild-type | 39 | 49 | 40 |
| A1 | | 26 | 29 |
| A2 | | 32 | 36 |
| A | | 24 | 26 |
| A4 | | 32 | 39 |

TABLE 24-continued

Specific Activities of α-, β- and γ-CD Forming CGTases

| | Cyclization Activity (U/mg) | | |
|---|---|---|---|
| Enzyme | α | β | γ |
| A5 | 43 | 27 | 27 |
| A11 | 20 | 6 | 13 |

TABLE 25

Ratio of Cyclodextrin Formation at Optimum CD Formation

| | Cyclodextrin produced (%) | | |
|---|---|---|---|
| Enzyme | α | β | γ |
| Wild-type | 39 | 45 | 17 |
| A1 | 42 | 38 | 20 |
| A2 | 38 | 45 | 17 |
| A | 42 | 38 | 20 |
| A4 | 39 | 41 | 20 |
| A5 | 42 | 37 | 20 |

Example 6
Construction of β-cyclodextrin Producing CGTase Variants from Thermoanaerobacter This example describes the construction of 15 β-cyclodextrin producing CGTase variants (B1–B9), in which site-directed mutagenesis either has lead to an altered number of hydrogen bonds in the subsites of the active cleft or, alternatively, to sterical hindrance in parts of the substrate binding left.

The variants are derived from a Thermoanaerobacter sp. CGTase obtained according to WO 89/03421, and having the nucleotide and amino acid sequences presented as SEQ ID NOS:1–2 (i.e. the wild-type enzyme).

Mutations were introduced by a method based on PCR by the use of PWO polymerase. For each mutation, specific oligonucleotides (primers) were developed. The mutations were confirmed by restriction analysis whenever possible, and by sequencing. Mutant proteins were expressed in either *Escherichia coli* MC1061 [Meissner P S, Sisk W P, Berman M L; *Proc. Natl. Acad. Sci. USA* 1987 84 4171–4175], or in the α-amylase and protease negative *Bacillus subtilis* Strain DB104A [Smith H, de Jong A, Bron S, Venema G; *Gene* 1988 70 351–361]. Proteins were purified from the media using affinity chromatography (AfC) and/or anion-exchange chromatography (AEC).

Enzyme Assays

Enzymatic activity was measured by a slightly modified procedure of the Phadebas amylase test (Pharmacia). Phadebas tablets (Phadebas™ Amylase Test, Pharmacia) are used as substrate. This substrate is a cross-linked insoluble blue-colored starch polymer, which is mixed with bovine serum albumin and a buffer substance. After suspension in water, starch is hydrolyzed by the enzyme, thereby yielding blue fragments. The determination is carried out after incubation at 60° C., pH 6.2, in 0.15 nM calcium for 15 minutes. The absorbance of the resulting blue solution, determined at 620 nm, corresponds the enzymatic activity.

The enzyme activity is compared to that of an enzyme standard, and the activity is expressed in the same unit as that of the enzyme standard. The enzyme standard was Termamyl™ (Novo Nordisk A/D, Denmark), the amylolytic activity of which has been be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alfa Amylase Unit (KNU) is defined as the amount of enzyme which, under standard conditions (i.e. at 37° C. +/−0.05; 0.0003 M $Ca^{2+}$; and pH 5.6) dextrinizes 5.26 g starch dry substance Merck Amylum solubile. Below the activity is expressed in Novo Units (NU) per ml.

CGTase activity was determined by incubating diluted enzyme with substrate in 10 mM sodium citrate, pH 6.0 for 4–10 minutes at 85° C.

Cyclodextrin forming activity was determined using 5% Paselli™ SA2 (i.e. partially hydrolysed potato starch with an average degree of polymerization of 50, available from AVEBE, Foxhol, The Netherlands) as substrate. The α-cyclodextrin formed was determined with Methyl-orange, the β-cyclodextrin formed was determined with phenolphthalein, and the γ-cyclodextrin formed was determined with bromo cresol green. The activity is expressed in units per mg (U/mg). One unit of enzyme activity is defined as the amount of enzyme able to produce one μmol of the specific cyclodextrin per minute.

Cyclodextrin formation was also determined under conventional industrial production process conditions. A pre-cooked 10% amylopectin solution in 0.5 mM $CaCl_2$ at pH 5.5 was incubated with 50 NU of CGTase per gram of substrate, at 85° C. and for 24 hours. Samples are regularly withdrawn and boiled for 10 minutes at a pH of 2.5-3 prior to analysis by HPLC.

The results of these experiments are discussed and presented in tables 26–28, below. In Table 28, the figures are the ratio at maximum total level of cyclodextrin.

Oligonucleotide Primers

The following oligonucleotides were synthesized in order to initiate the site-directed mutagenesis (the numbers indicate positions according to the CGTase numbering):

B1: S145A;

5'-CTCCTGCAGCTGAGACAGACCC-3' (SEQ ID NO:38);

B2: E146S;

5'-CTCCTGCATCGTCGACAGACCC-3' (SEQ ID NO:39);

B3: T147A;

5'-TCAGAGGCGGATCCTACCTATGG-3' (SEQ ID NO:40);

-continued

B4: T147L;

5'-TCAGAGCTCGACCCTACCTATGG-3' (SEQ ID NO:41);

B5: D148A;

5'-CAGAGACGGCGCCTACCTATGGGG-3' (SEQ ID NO:42);

B6: D89A;

5'-CGCAGTTTTGCCGGCTTCCAC-3' (SEQ ID NO:43);

B7: F91aA;

5'-TCCACTGCCGGCGGAAGCAC-3' (SEQ ID NO:44);

B8: F91a*;

5'-AGATTCTACCGGTGGAAGCAC-3' (SEQ ID NO:45);

B9: 87–94 (IKYSG-VNN) (SEQ ID NO:11);

5'-TTTACGCAGTTATTAAATATTCCGGCGTTAACAACACATCCTATCATGG-3'

(SEQ ID NO:46). This variant is also used in the construction of A2 of Example 5, above;

B10: F195Y+87–94(IKYSG-VNN) (SEQ ID NO:11);

5'-TTACCGTAATTTATATGACTTAGCAG-3' (SEQ ID NO:67) was used to introduce the F195Y mutation. Using this variant as starting point, the 87–94(IKYSG-VNN) (SEQ ID NO:11) mutations was introduced using primer B9. Simultaneously, the F195 was replaced by 195Y in order to decrease the contact between enzyme and substrate;

B11: D196S;

5'-CGTAATTTATTCTCGCTAGCAGATTTAG-3' (SEQ ID NO:68);

B12: D196A;

5'-CGTAATTTATTCGCGCTAGCAGATTTAG-3' (SEQ ID NO:47);

B13: D371N;

5'-CAGGTAATGGTAACCCTTATAATAGAGC-3' (SBQ ID NO:48);

B14: D371G;

5'-CAGGTAATGGAGGGCCTTATAATAGAGC-3' (SEQ ID NO:49); and

B15: D371A;

5'-CAGGTAATGGAGCGCCTTATAATAGAGC-3' (SEQ ID NO:50).

Results

The variants of this example were designed in order to increase β-cyclodextrin formation.

In experiment B1, S145 was replaced by 145A in order to decrease the interactions between the enzyme and glucose unit J (cf. FIG. 1). The initial rate of both β-CD formation and of γ-CD formation has increased. In the CD-production assay, the ratio of α-CD has decreased whereas the β-CD ratio has increased.

In experiment B2, E146 was replaced by 146S in order to increase the interactions between the enzyme and glucose unit I (cf. FIG. 1). The initial rate of both β-CD formation and of γ-CD formation has increased. In the CD-production assay, the ratio of α-CD has decreased.

In experiment B3, T147 was replaced by 147A in order to decrease the interactions between the enzyme and glucose unit J (cf. FIG. 1). In the CD-production assay, the ratio of α-CD has decreased, whereas the β-CD ratio has increased.

In experiment B4, T147 was replaced by 147L in order to decrease the interactions between the enzyme and glucose unit J (cf. FIG. 1). In the CD-production assay, the ratio of α-CD has decreased, whereas the β-CD ratio has increased.

In experiment B5, D148 was replaced by 148A in order to decrease the interactions between the enzyme and glucose unit J. In the CD-production assay, the ratio of α-CD has decreased, whereas the β-CD ratio has increased.

In experiment B6, D89 was replaced by 89A in order to decrease the interactions between the enzyme and glucose unit F. The initial rate of both β-CD formation and of γ-CD formation has decreased.

In experiment B7, Y91a was replaced by 91aA in order to decrease the interactions between the enzyme and glucose unit F. The initial rate of both β-CD formation and of γ-CD formation has decreased.

In experiment B8, Y91a was replaced by Y91a* (deleted) in order to decrease the interactions between the enzyme and glucose unit F. The initial rate of β-CD formation has decreased.

In experiment B9, the loop at positions 87 to 94 was replaced by (IKYSG*VNN) (SEQ ID NO:11) in order to increase the contacts between the enzyme and glucose units E and F (cf. FIG. 1).

In experiment B 10, 5'-TTACCGTAATTTATATGACTTAGCAG-3' (SEQ ID NO:67) was used to introduce the F195Y mutation. Using this variant as starting point, the 87–94(IKYSG-VNN) (SEQ ID NO:11) mutations was introduced using primer B9. Simultaneously, the F195 was replaced by 195Y in order to decrease the contact between enzyme and substrate.

In experiment B11, D196 was replaced by 196S in order to decrease the interactions between the enzyme and glucose unit E and glucose unit F.

In experiment B12, D196 was replaced by 196A in order to decrease the interactions between the enzyme and glucose unit E and glucose unit F.

In experiment BBB, D371 was replaced by 371N in order to decrease the interactions between the enzyme and glucose unit E and glucose unit F.

In experiment B14, D371 was replaced by 371G in order to decrease the interactions between the enzyme and glucose unit E and glucose unit F.

In experiment B15, D371 was replaced by 371A in order to decrease the interactions between the enzyme and glucose unit E and glucose unit F.

TABLE 26

Production, Purification and Enzyme Activities of CGTases

| Enzyme | Host | Purification method | Enzyme activity (NU/ml) |
|---|---|---|---|
| Wild-type | Bacillus | AfC | 1513 |
| B1 | Bacillus | AfC | 1925 |
| B2 | Bacillus | AfC | 2290 |
| B3 | Bacillus | AfC | 1636 |
| B4 | Bacillus | AfC | 1949 |
| B5 | Bacillus | AfC | 1839 |
| B6 | E. coli | AfC | 1908 |
| B7 | E. coli | AfC | 1686 |
| B8 | E. coli | AfC | 1212 |
| B9 | E. coli | AfC | 1862 |

TABLE 27

Specific Activities of α-, β- and γ-CD Forming CGTases

| | Cyclization Activity (U/mg) | | |
|---|---|---|---|
| Enzyme | α | β | γ |
| Wild-type | 39 | 131 | 96 |
| B1 | | 150 | 140 |
| B2 | | 140 | 120 |
| B3 | | 120 | 84 |
| B4 | | 110 | 97 |
| B5 | | 120 | 82 |
| B6 | | 101 | 84 |
| B7 | | 107 | 80 |
| B8 | | 118 | 97 |
| B9 | | 131 | 63 |

TABLE 28

Ratio of Cyclodextrin Formation at Optimum CD Formation

| | Cyclodextrin produced (%) | | |
|---|---|---|---|
| Enzyme | α | β | γ |
| Wild-type | 39 | 45 | 17 |
| B1 | 35 | 49 | 16 |
| B2 | 35 | 46 | 18 |
| B3 | 35 | 48 | 16 |
| B4 | 35 | 49 | 16 |
| B5 | 35 | 49 | 16 |
| B9 | 35 | 48 | 17 |

Example 7

Construction of β-cyclodextrin Producing CGTase Variants from Thermoanaerobacter This example describes the construction of 9 β-cyclodextrin producing CGTase variants (C1–C9), in which site-directed mutagenesis either has lead to an altered number of hydrogen bonds in the subsites of the active cleft or, alternatively, to sterical hindrance in parts of the substrate binding left.

The variants are derived from a Thermoanaerobacter sp. CGTase obtained according to WO 89/03421, and having the nucleotide and amino acid sequences presented as SEQ ID NOS:1–2 (i.e. the wild-type enzyme).

Variants were introduced by a method based on Unique Site Elimination (USE), following the protocol from the supplier (Stratagene®). The unique restriction site BsaMI at the plasmid opposite to the CGTase gene was removed by the use of the 5'P-CACTGTTCCTTCGAACGCGTAACCTTAAATACC-3' (SEQ ID NO:69) oligonucleotide. In this oligonucleotide, "P" indicates a 5' phosphorylation necessary for the procedure. For each mutation specific oligonucleotides were developed. The mutations were confirmed by restriction analysis whenever possible, and by sequencing. Mutant proteins were expressed in either Escherichia coli MC1061 [Meissner P S, Sisk W P, Berman M L; Proc. Natl. Acad. Sci. USA 1987 84 4171–4175]. Proteins were purified from the media using affinity chromatography (AfC).

Enzyme Assays

Enzymatic activity was measured by a slightly modified procedure of the Phadebas amylase test (Pharmacia). Phadebas tablets (Phadebas™ Amylase Test, Pharmacia) are used as substrate. This substrate is a cross-linked insoluble blue-colored starch polymer, which is mixed with bovine serum albumin and a buffer substance, After suspension in water, starch is hydrolyzed by the enzyme, thereby yielding blue fragments. The determination is carried out after incubation at 60° C., pH 6.2, in 0.15 nM calcium for 15 minutes. The absorbance of the resulting blue solution, determined at 620 nm, corresponds the enzymatic activity.

The enzyme activity is compared to that of an enzyme standard, and the activity is expressed in the same unit as that of the enzyme standard. The enzyme standard was Termamyl™ (Novo Nordisk A/D, Denmark), the amylolytic activity of which has been be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alfa Amylase Unit (KNU) is defined as the amount of enzyme which, under standard conditions (i.e. at 37° C. +/−0.05; 0.0003 M $Ca^{2+}$; and pH 5.6) dextrinizes 5.26 g starch dry substance Merck Amylum solubile. Below the activity is expressed in Novo Units (NU) per ml.

CGTase activity was determined by incubating diluted enzyme with substrate in 10 mM sodium citrate, pH 6.0 for 4–10 minutes at 85° C.

Cyclodextrin forming activity was determined using 5% Paselli™ SA2 (i.e. partially hydrolysed potato starch with an average degree of polymerization of 50, available from AVEBE, Foxhol, The Netherlands) as substrate. The α-cyclodextrin formed was determined with Methyl-orange, the β-cyclodextrin formed was determined with phenolphthalein and the γ-cyclodextrin formed was determined with bromo cresol green. The activity is expressed in units per mg (U/mg). One unit of enzyme activity is defined as the amount of enzyme able to produce one βmol of the specific cyclodextrin per minute.

Cyclodextrin formation was also determined under conventional industrial production process conditions. A precooked 10% amylopectin solution in 0.5 mM $CaCl_2$ at pH 5.5 was incubated with 50 NU of CGTase per gram of substrate, at 60° C. and for 24 hours. Samples are regularly withdrawn and boiled for 10 minutes at a pH of 2.5-3 prior to analysis by HPLC.

The results of these experiments are discussed and presented in tables 29–31, below. In Table 31, the figures are the ratio at maximum total level of cyclodextrin.

Oligonucleotide Primers

The following oligonucleotides were synthesized in order to initiate the site-directed mutagenesis (the numbers indicate positions according to the CGTase numbering):

unit H. In the CD-production assay, the ratio of α-CD has decreased, and the ratio of β-CD has increased.

In experiment C2, the region at positions 146–150 was replaced by (SDQPS) (SEQ ID NO:59) in order to decrease the interactions between the enzyme and glucose unit J, and in order to increase the interactions between the enzyme and glucose unit I.

In experiment C3, the region at positions 145–148 was replaced by (AELA) (SEQ ID NO:60) in order to decrease the interactions between the enzyme and glucose unit J, and in order to increase the interactions between the enzyme and glucose unit I.

In experiment C4, the region at positions 145–148 was replaced by (AEWA) (SEQ ID NO:61) in order to decrease the interactions between the enzyme and glucose unit J, and in order to increase the interactions between the enzyme and glucose unit I.

In experiment C5, the loop at positions 87–94 was replaced by (INYSG*VNN) (SEQ ID NO:62) in order to decrease the interactions between the enzyme and glucose unit E and glucose unit F.

In experiment C6, the loop at positions 87–94 was replaced by (HP*SGY***) (SEQ ID NO:3) in order to decrease the interactions between the enzyme and glucose unit E and glucose unit F.

In experiment C7, the region at positions 145–148 was replaced by (LETN) (SEQ ID NO:63) in order to decrease the interactions between the enzyme and glucose unit J, and in order to increase the interactions between the enzyme and glucose unit I.

```
C1: N193A;

5'P-TTACCGTGCACTATTTGACTTAGC-3' (SEQ ID NO:51);

C2: 146-150(SDQPS) (SEQ ID NO:59);

5'P-CTCCTGCATCATCTGATCAACCGTCCTTTGGGGAAAATGG-3' (SEQ ID NO:52);

C3: 145-148 (AELA) (SEQ ID NO:60);

5'P-CATCTCCTGCAGCAGAGCTCGCACCTACCTATGGG-3' (SEQ ID NO:53);

C4: 145-148(AEWA) (SEQ ID NO:61);

5'P-CATCTCCTGCAGCAGAGTGGGCACCTACCTATGGG-3' (SEQ ID NO:54);

C5: 87-94 (INYSG*VNN) (SEQ ID NO:62);

5'P-CATTTACGCAGTTATCAATTATTCCGGAGTTAACAATACATCCTATCATGG-3' (SEQ ID NO:55);

C6: 87-94(HP*SGY***) (SEQ ID NO:3);

5'P-CATTTACGCAGTTCATCCTTCCGGGTATACATCCTATCATGG-3' (SEQ ID NO:56);

C7: 145-148 (LETN) (SEQ ID NO:63);

5'P-TACATCTCCTGCACTCGAGACAAATCCTACCTATGG-3' (SEQ ID NO:57);

C8: 87-94(HP*SGY***) (SEQ ID NO:3) + 145-148(LETN) (SEQ ID NO:63);
    Both primers listed as C6 and C7 were used simultaneously;

C9: 87-94(INYSG*VNN) (SEQ ID NO:62) + 146-150(SDQPS) (SEQ ID NO:59);
    Both primers listed C2 and C5 were used simultaneously.
```

Results

The variants of this example were designed in order to increase β-cyclodextrin formation.

In experiment C1, N193 were replaced by 193A in order to decrease the interactions between the enzyme and glucose In experiment C8, the loop at positions 87–94 was replaced by (HP*SGY***) (SEQ ID NO:3) in order to decrease the interactions between the enzyme and glucose unit E and glucose unit F. Simultaneously, the region at positions 145–148 was replaced by (LETN) (SEQ ID NO:63) in order to decrease the interactions between the enzyme and glucose unit J, and in order to increase the interactions between the enzyme and glucose unit I.

In experiment C9, the loop at positions 87–94 was replaced by (INYSG*VNN) (SEQ ID NO:62) in order to decrease the interactions between the enzyme and glucose unit E and glucose unit F. Simultaneously, the region at positions 145–148 was replaced by (SDQPS) (SEQ ID NO:59) in order to decrease the interactions between the enzyme and glucose unit J, and in order to increase the interactions between the enzyme and glucose unit I.

TABLE 29

Production, Purification and Enzyme Activities of CGTases

| Enzyme | Host | Purification method | Enzyme activity (NU/ml) |
|---|---|---|---|
| Wild-type | E. coli | AfC | 1513 |
| C1 | E. coli | AfC | 1643 |

TABLE 30

Specific Activities of α-, β- and γ-CD Forming CGTases

| | Cyclization Activity (U/mg) | | |
|---|---|---|---|
| Enzyme | α | β | γ |
| Wild-type | 39 | 131 | 96 |
| C1 | | 102 | 90 |

TABLE 31

Ratio of Cyclodextrin Formation at Optimum CD Formation

| | Cyclodextrin produced (%) | | |
|---|---|---|---|
| Enzyme | α | β | γ |
| Wild-type | 39 | 45 | 17 |
| C1 | 35 | 49 | 16 |

We claim:

1. A variant of a cyclodextrin glycosyl transferase, comprising one or more alterations selected from the group consisting of insertions, deletions and substitations, wherein each alteration independently results in:

(a) the amino acid at position 89 being alanine, aspartic acid or glycine, (b) the amino acid at position 94 being arginine, glutamine, lysine, tryptophan, or phenylalanine, or deleted, (c) the amino acid at position 145a being isoleucine, (d) the amino acid at position 147 being alanine, isoleucine, leucine, serine, or tryptophan, (e) the amino acid at position 147a being alanine, (f) the amino acid at position 149 being isoleucine, (g) the amino acid at position 167 being phenylalanine, (h) the amino acid at position 185 being arginine, aspartic acid, or glutamic acid, (i) the amino acid at position 186 being alanine, (j) die amino acid at position 193 being alanine, aspartic acid, glutamic acid, or glycine, (k) the amino acid at position 196 being alanine or leucine, (l) the amino acid at position 197 being aspartic acid or glutamic acid, (m) the amino acid at position 232 being alanine, asparagine, glutamine, or leucine, (n) the amino acid at position 268 being alanine, (o) the amino acid at position 371 being alanine, asparagine, glutamic acid, glycine, or leucine, (p) the amino acid at position 375 being alanine, asparagine, glutamine, glycine, leucine, or proline, (q) the amino acid at position 599a being arginine, histidine, or proline, (r) the amino acid at position 616 being alanine, (s) the amino acid at position 633 being alanine, (t) the amino acid at position 662 being alanine, (u) the amino acid at position 47 being histidine or arginine and at position 135 being leucine, (v) the amino acid at position 88 being proline and at position 143 being glycine, (w) the amino acid at position 89 being aspartic acid and at position 146 being proline, (y) the amino acid at position 143 being alanine and at position 144 being arginine, (z) the amino acid at position 143 being glycine, at position 144 being arginine, and at position 145 being tryptophan, (aa) the amino acids at positions 143–148 being GRA**A (SEQ ID NO:7), GRAAAA (SEQ ID NO:8), GRAPAA (SEQ ID NO:9), or GRGPAA (SEQ ID NO:10), (ab) the amino acid at position 144 being arginine, at position 145 being alanine, and at position 146 being proline, (ac) the amino acid at position 145 being alanine and at position 145a being isoleucine, (ad) the amino acid at position 145 being leucine and at position 148 being asparagine, (ae) the amino acid at position 145 being glutamic acid and at position 146 being glutamine or proline, (af) the amino acid at position 145 being tryptophan and at position 146 being arginine, isoleucine, or tryptophan, (ag) the amino acid at position 145 being alanine, at position 145a being isoleucine, and at position 148 being glutamic acid, (ah) the amino acids at position 616 being alanine and at position 662 being alanine, (ai) the amino acids at positions 87–94 being HP*SGY** (SEQ ID NO:3), and/or at positions 143–151 being PALETNPNF (SEQ ID NO:4) or PAAETWPAF (SEQ ID NO:5), (aj) the amino acids at positions 87–94 being HP*SGY** (SEQ ID NO:3), and/or at positions 143–151 being PALETNPNF (SEQ ID NO:4), or PAAEADPNF (SEQ ID NO:6), wherein each position corresponds to the position of the amino acid sequence of the mature cyclodexrin glycosyl transferase obtained from *Bacillus circulans* strain 251 and wherein the variant has cyclodextrin glycosyl transferase activity.

2. The variant of claim 1, wherein the cyclodextrin glycosyl transferase is obtained from *Bacillus circulans* 251, Bacillus sp. 1-1, Bacillus sp. 38-2, Bacillus sp. 1011, *Bacillus licheniformis, Bacillus macerans, Bacillus ohbensis, Bacillus stearothermophilus, Klebsiella pneumoniae,* or Thermoanaerobacter ATCC 53627.

3. The variant of claim 2, wherein the cyclodextrin glycosyl transferase is obtained from *Bacillus circulans* 251.

4. The variant of claim 2, wherein the cyclodextrin glycosyl transferase is obtained from Thermoanaerobacter ATCC 53627.

5. The variant of claim 2, wherein an alteration results in the amino acid at position 89 being alanine, aspartic acid or glycine.

6. The variant of claim 2, wherein an alteration results in the amino acid at position 94 being arginine, glutamine, lysine, tryptophan, phenylalanine, or deleted.

7. The variant of claim 2, wherein an alteration results in the amino acid at position 145a being isoleucine.

8. The variant of claim 2, wherein an alteration results in the amino acid at position 147 being alanine, isoleucine, leucine, serine, or tryptophan.

9. The variant of claim 2, wherein an alteration results in the amino acid at position 147a being alanine.

10. The variant of claim 2, wherein an alteration results in the amino acid at position 149 being isoleucine.

11. The variant of claim 2, wherein an alteration results in the amino acid at position 167 being phenylalanine.

12. The variant of claim 2, wherein an alteration results in the amino acid at position 185 being arginine, aspartic acid, or glutamic acid.

13. The variant of claim 2, wherein an alteration results in the amino acid at position 186 being alanine.

14. The variant of claim 2, wherein an alteration results in the amino acid at position 193 being alanine, aspartic acid, glutamic acid, or glycine.

15. The variant of claim 2, wherein an alteration results in the amino acid at position 196 being alanine or leucine.

16. The variant of claim 2, wherein an alteration results in the amino acid at position 197 being aspartic acid or glutamic acid.

17. The variant of claim 2, wherein an alteration results in the amino acid at position 232 being alanine, asparagine, glutamine, or leucine.

18. The variant of claim 2, wherein an alteration results in the amino acid at position 268 being alanine.

19. The variant of claim 2, wherein an alteration results in the amino acid at position 371 being alanine, asparagine, glutamic acid, glycine, or leucine.

20. The variant of claim 2, wherein an alteration results in the amino acid at position 375 being alanine, asparagine, glutamine, glycine, leucine, or proline.

21. The variant of claim 2, wherein an alteration results in the amino acid at position 599a being arginine, histidine, or proline.

22. The variant of claim 2, wherein an alteration results in the amino acid at position 616 being alanine.

23. The variant of claim 2, wherein an alteration results in the amino acid at position 633 being alanine.

24. The variant of claim 2, wherein an alteration results in the amino acid at position 662 being alanine.

25. A variant of claim 2, wherein an alteration results in the amino acid at position 47 being histidine or arginine, and at position 135 being leucine.

26. A variant of claim 2, wherein an alteration results in the amino acid at position 88 being proline, and at position 143 being glycine.

27. A variant of claim 2, wherein an alteration results in the amino acid at position 89 being aspartic acid, and at position 146 being proline.

28. A variant of claim 2, wherein an alteration results in the amino acid at position 143 being alanine, and at position 144 being arginine.

29. A variant of claim 2, wherein an alteration results in the amino acid at position 143 being glycine, at position 144 being arginine, and at position 145 being tryptophan.

30. A variant of claim 2, wherein an alteration results in the amino acids at positions 143–148 being GRA**A (SEQ ID NO:7), GRAAAA (SEQ ID NO:8), GRAPAA (SEQ ID NO:9), or GRGPAA (SEQ ID NO:10).

31. A variant of claim 2, wherein an alteration results in the amino acid at position 144 being arginine, at position 145 being alanine, and at position 146 being proline.

32. A variant of claim 2, wherein an alteration results in the amino acid at position 145 being alanine, and at position 145a being isoleucine.

33. A variant of claim 2, wherein an alteration results in the amino acid at position 145 being leucine, and at position 148 being asparagine.

34. A variant of claim 2, wherein an alteration results in the amino acid at position 145 being glutamic acid, and at position 146 being proline or glutamine.

35. A variant of claim 2, wherein an alteration results in the amino acid at position 145 being tryptophan, and at position 146 being tryptophan, isoleucine, or arginine.

36. A variant of claim 2, wherein an alteration results in the amino acid at position 145 being alanine, at position 145a being isoleucine, and at position 148 being glutamic acid.

37. A variant of claim 2, wherein an alteration results in the amino acid at position 145a being isoleucine, and at position 148 being glutamic acid.

38. A variant of claim 2, wherein an alteration results in the amino acid at position 616 being alanine, and at position 662 being alanine.

39. A variant of claim 2, wherein an alteration results in the amino acids at positions 87–94 being HP*SGY** (SEQ ID NO:3), and/or at positions 143–151 being PALETNPNF (SEQ ID NO:4) or PAAETWPAF (SEQ ID NO:5).

40. A variant of claim 2, wherein an alteration in the amino acids at positions 87–94 being HP*SGY** (SEQ ID NO:3), and/or at positions 143–151 being PALETNPNF (SEQ ID NO:4) or PAAETWPAF (SEQ ID NO:5), and the amino acid at position 195 being leucine.

41. A variant of claim 2, wherein an alteration results in the amino acids at positions 87–94 being HP*SGY** (SEQ ID NO:3), and/or at positions 143–151 being PALETNPNF (SEQ ID NO:4), or PAAEADPNF (SEQ ID NO:6).

42. A variant of claim 2, wherein an alteration results in the amino acids at positions 87–94 being HP*SGY** (SEQ ID NO:3), and/or at positions 143–151 being PALETNPNF (SEQ ID NO:4), or PAAEADPNF (SEQ ID NO:6), and at position 195 being leucine.

43. A DNA construct encoding a cyclodextrin glycosyl transferase variant of claim 1.

44. A DNA construct encoding a cyclodextrin glycosyl transferase variant of claim 2.

45. A variant of a cyclodextrin glycosyl transferase, comprising one or more alterations selected from the group consisting of insertions, deletions and substitutions, wherein each alteration independently results in:
   (a) the amino acid at position 21 being tyrosine,
   (b) the amino acid at position 47 being glutamine, alanine, or leucine,
   (c) the amino acid at position 88 being proline,
   (d) the amino acid at position 91a being alanine,
   (e) the amino acid at position 143 being alanine,
   (f) the amino acid at position 144 being lysine or aspartic acid,
   (g) the amino acid at position 145 being glutamic acid, tryptophan, glycine, phenylalanine, tyrosine, or proline,
   (h) the amino acid at position 146 being proline, serine, isoleucine, glutamine, tryptophan, or arginine,
   (i) the amino acid at position 148 being alanine, glycine, or glutamic acid,
   (j) the amino acid at position 264 being alanine, asparagine, or leucine,
   (k) the amino acid at position 600 being tryptophan, phenylalanine, arginine, or asparagine,
   (l) the amino acids at positions 87–94 being IKYSGVNN (SEQ ID NO:11), and at positions 143–151 being GRAGTNPGF (SEQ ID NO:12), or at positions 143–145 being GRW,
   wherein each position corresponds to the position of the amino acid sequence of the mature cyclodextrin glycosyl transferase obtained from *Bacillus circulans* strain 251 and wherein the variant has cyclodextrin glycosyl transferase activity.

46. The variant of claim 45, wherein the cyclodextrin glycosyl transferase is obtained from *Bacillus circulans* 251, Bacillus sp. 1- 1, Bacillus sp. 38-2, Bacillus sp. 1011, *Bacillus lichenifonnis, Bacillus macerans, Bacillus ohbensis, Bacillus stearothermophilus, Klebsiella pneumoniae,* or Thermoanaerobacter ATCC 53627.

47. The variant of claim 46, wherein the cyclodextrin glycosyl transferase is obtained from *Bacillus circulans* 251.

48. The variant of claim 46, wherein the cyclodextrin glycosyl transferase is obtained from Thermoanaerobacter ATCC 53627.

49. A variant of claim 46, wherein an alteration results in the amino acid at position 21 being tyrosine.

50. A variant of claim 46, wherein an alteration results in the amino acid at position 47 being glutamine, alanine, or leucine.

51. A variant of claim 46, wherein an alteration results in the amino acid at position 88 being proline.

52. A variant of claim 46, wherein an alteration results in the amino acid at position 91a being alanine.

53. A variant of claim 46, wherein an alteration results in the amino acid at position 143 being alanine.

54. A variant of claim 46, wherein an alteration results in the amino acid at position 144 being lysine or aspartic acid.

55. A variant of claim 46, wherein an alteration results in the amino acid at position 145 being glutamic acid, tryptophan, glycine, phenylalanine, tyrosine, or proline.

56. A variant of claim 46, wherein an alteration results in the amino acid at position 146 being proline, serine, isoleucine, glutamine, or tryptophan, or arginine.

57. A variant of claim 46, wherein an alteration results in the amino acid at position 148 being alanine, glycine, or glutamic acid.

58. A variant of claim 46, wherein an alteration results in the amino acid at position 264 being alanine, asparagine, or leucine.

59. A variant of claim 46, wherein an alteration results in the amino acid at position 600 being tryptophan, phenylalanine, arginine, or asparagine.

60. A variant of claim 46, wherein an alteration results in the amino acids at positions 87–94 being IKYSGVNN (SEQ ID NO:11), and at positions 143–151 being GRAGTNPGF (SEQ ID NO:12), or at positions 143–145 being GRW.

61. A DNA construct encoding a cyclodextrin glycosyl transferase variant of claim 45.

62. A DNA construct encoding a cyclodextrin glycosyl transferase variant of claim 46.

* * * * *

UNITED STATES PATENT AND TRADEMARK OFFICE

CERTIFICATE OF CORRECTION

PATENT NO. : 6,004,790

DATED : December 21, 1999

INVENTOR(S) : Dijkhuizen et al.

It is certified that error appears in the above-identified patent and that said Letters Patent is hereby corrected as shown below:

Column 135, line 35: delete "substitations", insert --substitutions--

Column 135, line 52: delete "die", insert --the--

Column 137, line 10, delete "cyclodexrin", insert --cyclodextrin--

Column 139, line 42, delete "lichenifonnis", insert --licheniformis--

Signed and Sealed this

First Day of May, 2001

Attest:

NICHOLAS P. GODICI

Attesting Officer

Acting Director of the United States Patent and Trademark Office